(12) United States Patent
Svenstrup et al.

(10) Patent No.: US 11,608,342 B2
(45) Date of Patent: *Mar. 21, 2023

(54) PDE9 INHIBITORS WITH IMIDAZO TRIAZINONE BACKBONE AND IMIDAZO PYRAZINONE BACKBONE FOR TREATMENT OF PERIPHERAL DISEASES

(71) Applicant: H. LUNDBECK A/S, Valby (DK)

(72) Inventors: Niels Svenstrup, København V (DK); Kate Wen, Shanghai (CN); Yazhou Wang, Shanghai (CN)

(73) Assignee: H. Lundbeck A/S, Valby (DK)

( * ) Notice: Subject to any disclaimer, the term of this patent is extended or adjusted under 35 U.S.C. 154(b) by 0 days.

This patent is subject to a terminal disclaimer.

(21) Appl. No.: 17/115,108

(22) Filed: Dec. 8, 2020

(65) Prior Publication Data

US 2021/0094960 A1    Apr. 1, 2021

Related U.S. Application Data

(63) Continuation of application No. 16/673,709, filed on Nov. 4, 2019, now abandoned, which is a continuation of application No. 15/742,086, filed as application No. PCT/EP2016/065964 on Jul. 6, 2016, now Pat. No. 10,513,524.

(30) Foreign Application Priority Data

Jul. 7, 2015   (DK) .............................. PA201500393
Jul. 10, 2015  (DK) .............................. PA201500407
Apr. 7, 2016   (DK) .............................. PA101600209

(51) Int. Cl.
   *C07D 487/04*    (2006.01)
   *A61P 7/00*      (2006.01)
   *A61P 13/08*     (2006.01)

(52) U.S. Cl.
   CPC .............. *C07D 487/04* (2013.01); *A61P 7/00* (2018.01); *A61P 13/08* (2018.01)

(58) Field of Classification Search
   CPC .................................................. C07D 487/04
   USPC ....................................................... 514/250
   See application file for complete search history.

(56) References Cited

U.S. PATENT DOCUMENTS

| | | | |
|---|---|---|---|
| 3,578,687 A | 5/1971 | Larkin et al. |
| 3,819,561 A | 6/1974 | Bruenner |
| 3,917,660 A | 11/1975 | Sasaki et al. |
| 4,599,430 A | 7/1986 | Milberger et al. |
| 5,412,137 A | 5/1995 | Prashad et al. |
| 5,716,988 A | 2/1998 | Ibrahim et al. |
| 5,741,211 A | 4/1998 | Renirie et al. |
| 5,919,816 A | 7/1999 | Hausheer et al. |
| 6,187,747 B1 | 2/2001 | Singh et al. |
| 6,262,029 B1 | 7/2001 | Press et al. |
| 6,346,231 B1 | 2/2002 | Opheim |
| 6,362,178 B1 | 3/2002 | Niewohner et al. |
| 6,376,688 B1 | 4/2002 | Ferrante et al. |
| 6,407,075 B1 | 6/2002 | Scott et al. |
| 6,410,802 B1 | 6/2002 | Dasseux et al. |
| 6,531,150 B1 | 3/2003 | Sunohara et al. |
| 6,652,879 B2 | 11/2003 | Opheim |
| 6,924,309 B2 | 8/2005 | Ferrante et al. |
| 6,998,395 B2 | 2/2006 | Jackson et al. |
| 7,312,191 B2 | 12/2007 | Rose et al. |
| 7,326,421 B2 | 2/2008 | Brekke et al. |
| 7,452,907 B2 | 11/2008 | Cheng et al. |
| 7,709,468 B2 | 5/2010 | Calderwood et al. |
| 7,741,324 B2 | 6/2010 | Crew et al. |
| 7,776,916 B2 | 8/2010 | Freeman et al. |
| 7,977,315 B2 | 7/2011 | Rose et al. |
| 8,299,080 B2 | 10/2012 | Okada et al. |
| 8,309,526 B2 | 11/2012 | Freeman et al. |
| 8,324,277 B2 | 12/2012 | Freeman |
| 8,563,565 B2 | 10/2013 | Norimine et al. |
| 8,563,609 B2 | 10/2013 | Miller |
| 8,686,038 B2 | 4/2014 | Yang |
| 8,686,167 B2 | 4/2014 | Miller |
| 8,735,449 B2 | 5/2014 | Freeman |
| 8,933,255 B2 | 1/2015 | Miller |
| 8,937,194 B2 | 1/2015 | Miller |
| 9,006,473 B2 | 4/2015 | Freeman et al. |
| 9,066,902 B2 | 6/2015 | Freeman et al. |
| 9,186,408 B2 | 11/2015 | Freeman et al. |
| 9,192,600 B2 | 11/2015 | Yang |
| 9,271,952 B2 | 3/2016 | Cushing |
| 9,295,678 B2 | 3/2016 | Freeman et al. |
| 9,308,189 B2 | 4/2016 | Miller |
| 9,434,731 B2 | 9/2016 | Siegel et al. |

(Continued)

FOREIGN PATENT DOCUMENTS

AU    2011202664 B2    4/2012
CA    2296224 A1       7/2000

(Continued)

OTHER PUBLICATIONS

Abud-Mendoza et al., Treating severe systemic lupus erythematosus with rituximab. An open study. Reumatol. Clin. 5(4):147-152 (2009).
Adjei et al., A phase I trial of the farnesyl transferase inhibitor SCH66336: evidence for biological and clinical activity. Cancer Res. 60:1871-1877 (2000).
Akaike et al., Antagonistic action of imidazolineoxyl N-oxides against endothelium-derived relaxing factor/NO through a radical reaction. Biochem. 32:827-832 (1993).
Akinsheye et al., Fetal hemoglobin in sickle cell anemia. Blood 118(1):19-27 (2011).
Alber, Signaling mechanisms of the *Mycobacterium tuberculosis* receptor Ser/Tur protein kinases. Curr. Opin. Struct. Biol. 19(6):650-657 (2009).
Almeida et al., High expression of the cGMP-specific phosphodiesterase, PDE9A, in sickle cell disease (SCD) and the effects of its inhibition in erythroid cells and SCD neutrophils. British Journal of Haematology 142(5):836-44 (2008).

(Continued)

*Primary Examiner* — Kahsay Habte
(74) *Attorney, Agent, or Firm* — Cooley LLP; Matthew Pavao; Chen Chen

(57) ABSTRACT

The present invention relates to PDE9 inhibitors and their use for treatment of benign prostate hyperplasia and sickle cell disease.

8 Claims, 3 Drawing Sheets

(56) References Cited

U.S. PATENT DOCUMENTS

| | | |
|---|---|---|
| 9,434,733 B2 | 9/2016 | Svenstrup et al. |
| 9,522,156 B2 | 12/2016 | Freeman et al. |
| 9,533,992 B2 | 1/2017 | Svenstrup et al. |
| 9,585,855 B2 | 3/2017 | Yang |
| 9,643,970 B2 | 5/2017 | Svenstrup et al. |
| 9,700,534 B2 | 7/2017 | Freeman et al. |
| 9,725,453 B2 | 8/2017 | Bursavich et al. |
| 9,771,366 B2 | 9/2017 | Dunn et al. |
| 9,850,249 B2 | 12/2017 | Svenstrup et al. |
| 9,993,477 B2 | 6/2018 | Svenstrup et al. |
| 10,513,524 B2 * | 12/2019 | Svenstrup ............ C07D 487/04 |
| 11,370,795 B2 | 6/2022 | Svenstrup et al. |
| 2001/0037598 A1 | 11/2001 | Suppes et al. |
| 2002/0128510 A1 | 9/2002 | Durley et al. |
| 2003/0078299 A1 | 4/2003 | Ferrante et al. |
| 2004/0006248 A1 | 1/2004 | Paiocchi et al. |
| 2004/0020186 A1 | 2/2004 | Orlando et al. |
| 2004/0023989 A1 | 2/2004 | Fryburg et al. |
| 2004/0092590 A1 | 5/2004 | Arterburn et al. |
| 2004/0147599 A1 | 7/2004 | Gagnon et al. |
| 2004/0176451 A1 | 9/2004 | Tamai et al. |
| 2004/0220176 A1 | 11/2004 | Dickason et al. |
| 2004/0220186 A1 | 11/2004 | Bell et al. |
| 2004/0254240 A1 | 12/2004 | Ferrante et al. |
| 2005/0136103 A1 | 6/2005 | Ben-Sasson et al. |
| 2005/0232981 A1 | 10/2005 | Ben-Sasson |
| 2006/0018874 A1 | 1/2006 | Radhakrishnan et al. |
| 2006/0063953 A1 | 3/2006 | Maurizio et al. |
| 2006/0100278 A1 | 5/2006 | Cooper et al. |
| 2006/0241088 A1 | 10/2006 | Arterburn et al. |
| 2007/0099925 A1 | 5/2007 | Calderwood et al. |
| 2007/0232579 A1 | 10/2007 | Freeman et al. |
| 2007/0275893 A1 | 11/2007 | Quay |
| 2008/0096961 A1 | 4/2008 | Serhan et al. |
| 2008/0107729 A1 | 5/2008 | Amin et al. |
| 2008/0108697 A1 | 5/2008 | Ibrahim et al. |
| 2009/0030003 A1 | 1/2009 | Verhoest et al. |
| 2009/0074857 A1 | 3/2009 | Dror et al. |
| 2009/0220612 A1 | 9/2009 | Perera |
| 2009/0326070 A1 | 12/2009 | Freeman et al. |
| 2010/0166918 A1 | 7/2010 | Miller |
| 2010/0216884 A1 | 8/2010 | Freeman |
| 2010/0286257 A1 | 11/2010 | Perricone |
| 2010/0286271 A1 | 11/2010 | Perricone |
| 2010/0286272 A1 | 11/2010 | Perricone |
| 2010/0331268 A1 | 12/2010 | Freeman et al. |
| 2011/0082147 A1 | 4/2011 | Harbeson et al. |
| 2011/0082206 A1 | 4/2011 | Miller |
| 2011/0092594 A1 | 4/2011 | Yang |
| 2011/0196037 A1 | 8/2011 | Yang |
| 2011/0256247 A1 | 10/2011 | Miller |
| 2011/0280852 A1 | 11/2011 | Miller |
| 2011/0312909 A1 | 12/2011 | Ciomei et al. |
| 2011/0319325 A1 | 12/2011 | Miller |
| 2012/0136034 A1 | 5/2012 | Freeman et al. |
| 2012/0157458 A1 | 6/2012 | Ripka et al. |
| 2012/0295925 A1 | 11/2012 | Tung et al. |
| 2013/0005730 A1 | 1/2013 | Sun et al. |
| 2013/0039956 A1 | 2/2013 | Dietz |
| 2013/0059912 A1 | 3/2013 | Freeman |
| 2013/0101514 A1 | 4/2013 | Cushing |
| 2013/0143907 A1 | 6/2013 | Norimine et al. |
| 2013/0210917 A1 | 8/2013 | Freeman et al. |
| 2014/0024713 A1 | 1/2014 | Yang |
| 2014/0088081 A1 | 3/2014 | Claffey et al. |
| 2014/0243380 A1 | 8/2014 | Yang |
| 2014/0271844 A1 | 9/2014 | Miller |
| 2014/0308336 A1 | 10/2014 | Indolfi et al. |
| 2015/0018417 A1 | 1/2015 | Freeman et al. |
| 2015/0045348 A1 | 2/2015 | Svenstrup et al. |
| 2015/0051283 A1 | 2/2015 | Batthyany Dighiero et al. |
| 2015/0246059 A1 | 9/2015 | Freeman et al. |
| 2015/0274736 A1 | 10/2015 | Svenstrup et al. |
| 2016/0081961 A1 | 3/2016 | Cushing |
| 2016/0081962 A1 | 3/2016 | Miller et al. |
| 2016/0151318 A1 | 6/2016 | Yang |
| 2017/0081333 A1 | 3/2017 | Svenstrup et al. |
| 2017/0095437 A1 | 4/2017 | Jorkasky |
| 2017/0173018 A1 | 6/2017 | Svenstrup et al. |
| 2018/0092948 A1 | 4/2018 | Weiss et al. |
| 2018/0155345 A1 | 6/2018 | Rennie et al. |
| 2018/0194770 A1 | 7/2018 | Svenstrup et al. |
| 2019/0307754 A1 | 10/2019 | Svenstrup et al. |
| 2020/0062770 A1 | 2/2020 | Svenstrup et al. |
| 2020/0247750 A1 | 8/2020 | Nam et al. |
| 2021/0085684 A1 | 3/2021 | Svenstrup et al. |
| 2021/0107911 A1 | 4/2021 | Buttar et al. |
| 2021/0177845 A1 | 6/2021 | Calamai et al. |
| 2022/0023302 A1 | 1/2022 | Svenstrup et al. |

FOREIGN PATENT DOCUMENTS

| | | |
|---|---|---|
| CN | 1344268 A | 4/2002 |
| CN | 1575191 A | 2/2005 |
| CN | 101448829 A | 6/2009 |
| CN | 101557826 A | 10/2009 |
| CN | 101687876 A | 3/2010 |
| CN | 102099024 A | 6/2011 |
| CN | 102307464 A | 1/2012 |
| CN | 101687876 B | 12/2012 |
| CN | 103313988 A | 9/2013 |
| CN | 104093720 A | 10/2014 |
| CN | 104220060 A | 12/2014 |
| CN | 103313988 B | 6/2016 |
| CN | 107810187 A | 3/2018 |
| DE | 102012008730 A1 | 6/2013 |
| EP | 0911333 A1 | 4/1999 |
| EP | 1097706 A1 | 5/2001 |
| EP | 1407767 A1 | 4/2004 |
| EP | 1772149 A1 | 4/2007 |
| EP | 2123301 A1 | 11/2009 |
| EP | 2123801 A1 | 11/2009 |
| EP | 3481398 A1 | 5/2019 |
| GB | 587992 A | 5/1947 |
| GB | 1407932 A | 10/1975 |
| JP | S62132804 A | 6/1987 |
| JP | 2001520189 A | 10/2001 |
| JP | 2003509485 A | 3/2003 |
| JP | 2004509097 A | 3/2004 |
| JP | 2008520739 A | 6/2008 |
| JP | 2011525525 A | 9/2011 |
| WO | WO-9809621 A1 | 3/1998 |
| WO | WO-9924433 A1 | 5/1999 |
| WO | WO-0106983 A2 | 2/2001 |
| WO | WO-0121575 A1 | 3/2001 |
| WO | WO-0160778 A2 | 8/2001 |
| WO | WO-0178654 A2 | 10/2001 |
| WO | WO-0178719 A1 | 10/2001 |
| WO | WO-0179156 A1 | 10/2001 |
| WO | WO-0115673 A3 | 3/2002 |
| WO | WO-0222559 A2 | 3/2002 |
| WO | WO-02102364 A1 | 12/2002 |
| WO | WO-03031399 A1 | 4/2003 |
| WO | WO-03037432 A1 | 5/2003 |
| WO | WO-03037899 A1 | 5/2003 |
| WO | WO-03039533 A1 | 5/2003 |
| WO | WO-03093270 A1 | 11/2003 |
| WO | WO-2004096811 A1 | 11/2004 |
| WO | WO-2005041972 A1 | 5/2005 |
| WO | WO-2005073164 A1 | 8/2005 |
| WO | WO-2005110396 A2 | 11/2005 |
| WO | WO-2006055965 A2 | 5/2006 |
| WO | WO-2006086727 A2 | 8/2006 |
| WO | WO-2007137819 A1 | 12/2007 |
| WO | WO-2007140433 A2 | 12/2007 |
| WO | WO-2008008767 A2 | 1/2008 |
| WO | WO-2008011085 A1 | 1/2008 |
| WO | WO-2008103753 A2 | 8/2008 |
| WO | WO-2008139293 A1 | 11/2008 |
| WO | WO-2009017802 A1 | 2/2009 |
| WO | WO-2009038671 A2 | 3/2009 |
| WO | WO-2009129495 A1 | 10/2009 |
| WO | WO-2009134383 A2 | 11/2009 |
| WO | WO-2009149496 A1 | 12/2009 |

(56) References Cited

FOREIGN PATENT DOCUMENTS

| WO | WO-2009155439 A2 | 12/2009 |
|---|---|---|
| WO | WO-2010012777 A1 | 2/2010 |
| WO | WO-2010042877 A1 | 4/2010 |
| WO | WO-2010078504 A1 | 7/2010 |
| WO | WO-2010084438 A1 | 7/2010 |
| WO | WO-2010129763 A1 | 11/2010 |
| WO | WO-2010129777 A1 | 11/2010 |
| WO | WO-2011011882 A1 | 2/2011 |
| WO | WO-2011014261 A1 | 2/2011 |
| WO | WO-2011028820 A1 | 3/2011 |
| WO | WO-2011030351 A2 | 3/2011 |
| WO | WO-2011041639 A2 | 4/2011 |
| WO | WO-2011056126 A1 | 5/2011 |
| WO | WO-2011098746 A1 | 8/2011 |
| WO | WO-2012040230 A1 | 3/2012 |
| WO | WO-2012110441 A1 | 8/2012 |
| WO | WO-2013053690 A1 | 4/2013 |
| WO | WO-2013110768 A1 | 8/2013 |
| WO | WO-2013116765 A1 | 8/2013 |
| WO | WO-2013170069 A1 | 11/2013 |
| WO | WO-2014036555 A1 | 3/2014 |
| WO | WO-2015023557 A1 | 2/2015 |
| WO | WO-2015073527 A1 | 5/2015 |
| WO | WO-2015185499 A1 | 12/2015 |
| WO | WO-2017005786 A1 | 1/2017 |
| WO | WO-2018009424 A1 | 1/2018 |
| WO | WO-2018218104 A1 | 11/2018 |
| WO | WO-2019226944 A1 | 11/2019 |
| WO | WO-2020047311 A1 | 3/2020 |
| WO | WO-2020206336 A1 | 10/2020 |
| WO | WO-2020227399 A1 | 11/2020 |
| WO | WO-2022036111 A1 | 2/2022 |
| WO | WO-2022093852 A1 | 5/2022 |

OTHER PUBLICATIONS

Almeida et al.: Hydroxyurea and a cGMP-amplifying agent have immediate benefits on acute vaso-occlusive events in sickle cell disease mice. Blood. 120(14):2879-2888 (2012).
Alsultan et al., Genetic studies of fetal hemoglobin in the Arab-Indian haplotype sickle cell-β(0) thalassemia. American Journal of Hematology 88(6):531-532 (2013).
Altschul et al., Gapped BLAST and PSI-BLAST: a new generation of protein database search programs. Nucleic Acids Res. 25(17) 3389-3402 (1997).
Anand et al., Synthesis and evaluation of small libraries of triazolylmethoxy chaicones, flavanones and 2-aminopyrimidines as inhibitors of mycobacterial FAS-II and PknG. Biorganic & Medicinal Chem. 20(17):5150-5183 (2012).
Arbeeny, C. et al., Renoprotection by treatment with CXA-10, an Endogenous Nitro Fatty Acid. Poster, Nov. 5, 2015, 1 page (2015).
Arbeeny, C. et al., Renoprotection by treatment with CXA10, an endogenous nitro-fatty Acid. J. Am. Soc. Nephrol. 26:126A, Abstract THP0158 (2015).
Arnold et al., Nitric oxide activates guanylate cyclase and increases guanosine 3':5'-cyclic monophosphate levels in various tissue preparations. Proc. Natl. Acad. Sci. 74:3203-3207 (1977).
Artim et al., Nitro-oleic acid targets transient receptor potential (TRP) channels in capsaicin sensitive afferent nerves of rat urinary bladder. Expt. Neural. 232:90-99 (2011).
Asakura et al., Synthesis and biological evaluation of y-fluoro-,y-unsaturated acids. J of Flourine Chem. 127:800-808 (2006).
Aunapuu et al., Morphological changes in experimental postischemic rat kidney. A pilot study. Ann. Anat. 187(1):63-70 (2005).
Baker et al., Convergence of nitric oxide and lipid signaling: Anti-inflammatory nitro-fatty acids. Free Radic. Biol. Med. 46:989-1003. (2009).
Baker et al., Fatty acid transduction of nitric oxide Signaling. J Biol. Chem. 280(51):42464-42475 (2005).
Baker et al., Nitro-fatty acid reaction with glutathione and cysteine; kinetic analysis of thiol alkylation by a Michael addition reaction. J of Biol. Chem. 282(42):31085-31093 (2007).

Baker et al., Red cell membrane and plasma linoleic acid nitration products: Synthesis, clinical identification, and quantitation. Proc. Natl. Acad. Sci. 101(32):11577-11582 (2004).
Balazy et al., Vicinal nitrohydroxyeicosatrienoic acids: vasodilator lipids formed by reaction of nitrogen dioxide with arachidonic acid. J Pharmacol. Ex Ther. 299(2):611-619 (2001).
Balazy, Isomerization and Nitration of arachidonic acid by nitrogen dioxide. Advances in Mass Spectrometry 15:375-376 (2001).
Baldus et al., Endothelial transcytosis of myeloperoxidase confers specificity to vascular ECM proteins as targets of tyrosine nitration. J Clin. Invest. 108(12):1759-1770 (2001).
Baldus et al., Is NO news bad news in acute respiratory distress syndrome. Am. J Respir. Crit. Care Med. 163:308-310 (2001).
Ballini et al., Fast diastereoselective Baylis-Hillman reaction by nitroalkenes: synthesis of di-and triene derivatives. Tetrahedron 60:4995-4999 (2004).
Ballini et al., Nitroalkanes and ethyl glyoxalate as common precursors for the preparation of both 13- keto esters and a, 13-unsaturated esters. Tetrahedron Letters 45:7027-7029 (2004).
Ballini et al., (Z)-7-nitro-3-heptene as central intermediate for the synthesis of jasmone, methyl jasmonate and y-jasmolactone. Synthetic Communications 19(3-4):575-583 (1989).
Banker et al., Modern Pharmaceutics, Marcel Dekker, Inc. 1979, New York (TOC) (1979).
Bates et al., Nitroalkene fatty acids mediate activation of Nrf2/ARE-dependent and PPARy-dependent transcription by distinct signaling pathways and with significantly different potencies. Biochem. 50:7765-7773 (2011).
Bates et al., Noncatalytic interactions between glutathione s-transferases and nitroalkene fatty acids modulate nitroalkene-mediated activation of peroxisomal proliferator-activated receptory. Biochem. 48:4159-4169 (2009).
Batthyany et al., Reversible post-translational modification of proteins by nitrated fatty acids in vivo. J Biol. Chem. 281(29):20450-20463 (2006).
Baumer Iodostarin 'Roche' in the treatment of syphilis. Deutsche Medizinische Wochenschrifr 39:1361 (case abstract) (1 page) (1913).
Beckman et al., Apparent hydroxyl radical production by peroxynitrite: implications for endothelial injury from nitric oxide and superoxide. Proc. Natl. Acad. Sci. 87:1620-1624 (1990).
Bell-Parikh et al., Biosynthesis of 15-deoxy-A12 14-PGJ2 and the ligation of PPARy. J Clin. Invest. 112(6):945-955 (2003).
Bennett et al., Cecil Textbook of Medicine 1996, 20th Ed., 1, 1004-1010 (1996).
Berge, S.M. et al., (1977) "Pharmaceuticals Salts", J. Pharma. Sci. 66: 1-19.
Bervejillo et al., Estudio del potencial anti-aterogenico del AANO2 in vivo. Tesina del grado de la Licenciatura en Bioquiica, Facultad de Ciencias, UdelR Feb. 5-6, 2012, Fig. 2 (in Spanish with English summary) (2012).
Biegert et al., Sequence context-specific profiles for homology searching. PNAS 106(10):3770-3775. (2009).
Bjorn, Clues emerge about benefits of briefly blocking blood flow. Nature 15(2):132 (2009).
Blair et al., Bathophenanthrolinedisulphonic acid and bathocuproinedisulphonic acid, water soluble reagents for iron and copper. Taianta 7(3-4):163-174 (abstract) (1961).
Blakemore, The modified Julia olefination: alkene synthesis via the condensation of metallated heteroarylalkylsulfones with carbonyl compounds. J Chem. Soc. Perkin Trans. I. 23:2563-2585 (2002).
Blanco et al., 6-Methylnitroarachidonate: A novel esterified nitroalkene that potently inhibits platelet aggregation and exerts cGMP-mediated vascular relaxation. Free Radic. Biol. Med. 50:411-418 (2011).
Bligh et al., A rapid method of total lipid extraction and purification. Can. J Biochem. Physiol. 37(8):911-917 (1959).
Blockland, A. et al., (2006) "Improving Memory: A Role for Phosphodiesterases", Curr. Pharm. Des. 12(20):2511-2523.
Bloodsworth et al., Nitric oxide regulation of free radical- and enzyme-medicated lipid and lipoprotein oxidation. Arterioscler Thromb. Vasc. Biol. 20:1707-1715 (2000).

(56) References Cited

OTHER PUBLICATIONS

Boden et al., Free fatty acids in obesity and type 2 diabetes: defining their role in the development of insulin resistance and -cell dysfunction. Euro. J Clin. Invest. 32(Suppl. 3):14-23 (2002).
Bonacci et al., Electrophilic fatty acids regulate matrix metalloproteinase activity and expression. J Biolo. Chem. 286(18):16074-16081 (abstract) (2011).
Bonacci et al., Gas-phase fragmentation analysis of nitro-fatty acids. J Am. Soc. Mass Spec. 22:1534-1551 (2011).
Bonacci et al., Nitro-oleic acid improves insulin signaling via protein tyrosine phosphatase-lb inhibition. Free Radical Bio. Med. Elsevier Science, 45(Suppl. 1):SI54 (abstract) (2008).
Bonomi et al., Direct metal ion substitution at the [M(Scys)41 2 site of rubredoxin. J Biol. Inorg. Chem. 3(6):595-605 (1998).
Borniquel et al., Nitrated oleic acid up-regulates PPARy and attenuates experimental inflammatory bowel disease. Free Radic. Bio. Med. 49(4):499-505 (2010).
Boruwa et al., Catalytic asymmetric henry reaction. Tetrahedron: Asymmetry Report No. 90(17):3315-3326 (2006).
Breer, H. et al., (1990) "Rapid Kinetics of Second Messenger Formation in Olfactory Transduction" Nature 345 :6270):65-68.
Burdge, a-Linolenic acid metabolism in men and women: nutritional and biological ilmplications. Clin. Nutri. Metabol. Care 7:137-144 (2004).
Cannon, Burger's Medicinal Chemistry and Drug Discovery 1995, Fifth Edition, I: Principles and Practice, Chap. 19, John Wiley & Sons, Inc., 783-802 (1995).
Castro et al., Cytochrome c: a catalyst and target of nitrate-hydrogen peroxide-dependent protein nitration. Arch. Biochem. Biophys. 421:99-107 (2004).
Chawla, et al. Current Research & Information on Pharmaceutical Sciences (CRIPS), 5(1), 2004, 9-12.
Chawla et al., PPAR-y dependent and independent effects on macrophage-gene expression in lipid metabolism and inflammation. Nat. Med. 7(1):48-52 (2001).
Chen et al., Peroxisome proliferator-activated receptors and the cardiovascular system. Vitam. Harm. 66:157-188 (2003).
Chen et al., Synthesis and screening of novel vitamin E derivatives for anticancer functions. European J of Medicinal Chem. 58:72-83 (2012).
Chen et al., Troglitazone inhibits atherhosclerosis in apolipoprotein E-knockout mice: pleiotropic effects on CD36 expression and HDL. Arterioscler Thromb. Vasc. Biol. 21:372-377 (2001).
Chieffo, C. et al., Use of an obese population in phase I to evaluate the pharmacology of oral CXA-10, an endogenous nitro-fatty acid signaling agent. Poster, 4 pages (Sep. 26, 2016).
Christiansen, T. et al., Monocyte chemoattractant protein-1 is produced in isolated adipocytes, associated with adiposity and reduced after weight loss in morbid obese subjects. International Journal of Obesity 29:146-150 (2005).
Ückert [Ueckert] et al., Phosphodiesterase inhibitors in clinical urology. Expert Review in Clinical Pharmacology 6(3):323-332 (2013).
Ückert [Ueckert], S. et al., "Phosphodiesterase (PDE) inhibitors in the treatment of lower urinary tract dysfunction" (2011) Br. J. Clin. Pharmacol 72(2): 197-204.
Clapp et al., Oxygenation of monounsaturated fatty acids by soybean liposygenase-1: evidence for transient hydroperoxide formation. Biochem. 45:15884-15892 (2006).
Claudel et al., Reduction of atherosclerosis in apolipoprotein E knockout mice by activation of the retinoid X receptor. Proc. Natl. Acad. Sci. 98(5):2610-2615 (2001).
Coffey et al., Catalytic consumption of nitric oxide by 12/15-lipoxygenase: Inhibition of monocyte soluble guanylate cyclase activation. Proc. Natl. Acad. Sci. 98(14):8006-8011 (2001).
Cole et al., Deciphering the biology of *Mycobacterium tuberculosis* from the complete genome sequence. Nature 393:537-544 (1998).
Cole et al., Nitro-fatty acid inhibition of neointima formation after endoluminal vessel injury. Circ. Res. Nov. 6, 2009, 1-8; Suppl. Materials 1-6. (2009).
Coles et al., Nitrolinoleate inhibits platelet activation by attenuating calcium mobilization and inducing phosphorylation of vasodilator-stimulated phosphoprotein through elevation of cAMP. J Biol. Chem. 277(8):5832-5840 (2002).
Coles et al., Nitrolinoleate inhibits superoxide generation, degranulation, and integrin expression by human neutrophils. Novel antiinflammatory properties of nitric oxide-derived reactive species in vascular cells. Circ. Res. 91:375-381 (2002).
Collins et al., Troglitazone inhibits formation of early atherosclerotic lesions in diabetic and nondiabetic low density lipoprotein receptor-deficient mice. Arterioscler Thromb. Vasc. Biol. 21:365-371 (2001).
Conran, N. "Prospects for early investigational therapies for sickle cell disease" (2015) Expert Opin. Investig. Drugs 24(5):595-602.
Cooke, S.F. et al., (2006) "Plasticity in the Human Central Nervous System" Brain 129(7):1659-1673.
Cosby et al., Nitrite reduction to nitric oxide by deoxyhemoglobin vasodilates the human circulation. Nat. Med. 9(12):1498-1505 (2003).
Cowley et al., The *Mycobacterium tuberculosis* protein serine/threonine kinase PknG is linked to cellular glutamate/glutamine levels and is important for growth in vivo. Molecular Microbio. 52(6):1691-1702 (2004).
Cui et al., Nitrated fatty acids: endogenous anti-inflammatory signaling mediators. J Biol. Chem. 281(47):35686-35698 (2006).
Da Silva et al., Phosphodiesterase-9 (PDE9) inhibition with BAY 73-6691 increases corpus cavernosum relaxations mediated by nitric oxide-cyclic GMP pathway in mice. International Journal of Impotence Research 25(2):69-73 (2013).
Dang et al. (Hung), Anti-inflammatory constituents of the red alga gracilaria verrucosa and their synthetic analogues. J Nat. Prod. 71(2):232-240 (2008).
Dangi et al., Biogenic synthesis, purification, and chemical characterization of anti-inflammatory resolvins derived from docosapentaenoic acid (DPAn-6). J Biol. Chem. 284(22):14744-14759 (2009).
Davies et al., Oxidized alkyl phospholipids are specific, high affinity peroxisome proliferator-activated receptory ligands and agonists. J Biol. Chem. 276(19):16015-16023 (2001).
De Meijere et al., Metal-catalyzed cross-coupling reactions. Wiley-VCH Verlag GMbH & Co. 2004, Weinheim, vols. 1 and 2, XXII, ISBN-10: 3-527-30518-1 and ISBN-13: 978-3-527-30518-6 (TOC) (2004).
Defronzo et al., Insulin resistance: a multifaceted syndrome responsible for NIDDM, obesity, hypertension, dyslipidemia, and atherosclerotic cardiovascular disease. Diabetes Care 14(3):175-194 (1991).
Del Mar Grasa et al., Daily oral oleoyl-estrone gavage induces a dose-dependent loss of fat in Wistar rats. Obesity Res. 9(3):202-209 (2001).
Delerive et al., Oxidized phospholipids activated PPARa in a phospholipase A2-dependent manner. FEES Lett. 471:34-38 (2000).
Dembitsky et al., Natural halogenated fatty acids: their analogues and derivatives. Progress in Lipid Research 41(4):315-367 (2002).
Denicola et al., Diffusion of nitric oxide into low density lipoprotein. J Biol. Chem. 277(2):932-936 (2002).
Denicola et al., Diffusion of peroxynitrite across erythrocyte membranes. Proc. Natl. Acad. Sci. 95:3566-3571 (1998).
Desper et al., Getting a tree fast: neighbor joining, FastME, and distance-based methods. Curr. Protoc. Bioinformatics, Chap. 6, Unit 6.3 (2006).
Diabetic ketoacidosis in www.mayoclinic.org/diseases-conditions/diabetic-ketoacidosis/basics/treatment/con-20026470 (retrieved from the internet Jan. 21, 2016).
d'Ischia et al., Medium-dependent competitive pathways in the reactions of polyunsaturated fatty acids with nitric oxide in the presence of oxygen. Structural characterisation of nitration products and a theoretical insight. Tetrahedron 55:9297-9308 (1999).
d'Ischia, Oxygen-dependent nitration of ethyl linoleate with nitric oxide. Tetrahedron Lett. 37(32):5773-5774 (1996).
Dodge et al., Composition of phospholipids and of phospholipids fatty acids and aldehydes in human red cells. J Lipid Res. 8:667-675 (1967).

(56) References Cited

OTHER PUBLICATIONS

Doksorubitsin-Ebeve, Instruksiya po primeneniyu lekarstvennogo perparata dlya meditinskogo primeneniya, Retrieved from the Internet: Nov. 19, 2014, http://medi.ru/doc/f4509.htm.
Dorwald, Side Reactions in Organic Synthesis. Wiley-VCH, 1-16 (2005).
Duan et al., Nephrotoxicity of high- and low-osmolar contrast media: Protective role of forsinopril ortelmisartan in a rat model. J Central S. Univ. 32(5):812-818 (2007).
Duncton, M.A.J. et al. (2008) "Preparation of Aryloxetanes and Arylazetidines by Use of an Alkyl-Aryl Suzuki Coupling" Organic Letters 10(15):3259-3262.
Eardley, K.S. et al., The relationship between albuminuria, MCP-1/CCL2, and interstitial macrophages in chronic kidney disease. Kidney Int. 69:1189-1197 (2006).
Easton et al., Polyunsaturated nitroalkanes and nitro-substituted fatty acides. Synthesis 3:451-457 (2001).
Eberhardt et al., Prevalence of overweight and obesity among adults with Diagnosed Diabetes—United States, 1988-1994 and 1999-2002. CDC, Nov. 19, 2004; 53(45):1066-1068 (2004).
Eiserich et al., Myeloperoxidase, a leukocyte-derived vascular NO oxidase. Sci. 296:2391-2394 (2002).
Eiserich et al., Pathophysiology of nitric oxide and related species: free radical reactions and modification of biomolecules. Malec. Aspects Med. 19:221-357 (1998).
Escudier et al., Bevacizumab plus interferon alfa-2a for treatment of metastatic renal cell carcinoma: a randomized, double-blind phase III trial. The Lancet 370:2103-2111 (2007).
Eurasian Patent Application No. 202190460 Office Action received Jul. 16, 2021.
Evans et al., PPARs and the complex journey to obesity. Nat. Med. 10(4):1-7 (2004).
Ex Parte Sauerberg, Appeal 2015-007064, Decided Jan. 12, 2017.
Extended European Search Report dated Oct. 25, 2016 in Application No. 16185105.0, entitled PDE9I With Imidazo Pyrazinone Backbone.
Extended European Search Report dated Mar. 10, 2017 in European Application No. 17152165.1, entitled "PDE9I With Imidazo Triazinone Backbone".
Fazzari, M. et al., Generation and esterification of electrophilic fatty acid nitroalkenes in triacylglycerides. Free Radical Biology and Medicine 87:113-124 (2015).
Feelisch et al., Concomitant S-, N-, and heme-nitros(yl)ation in biological tissues and fluids: implications for the fate of NO in vivo. FASEB J 16:1775-1785 (2002).
Ferreira et al., Macrophage activation induces formation of the anti-inflammatory lipid cholesteryl-nitrolinoleate. Biochem. J. 417:223-234 (2009).
Ferry et al., Binding of prostaglandins to human PPARy: tool assessment and new natural ligands. Eur. J Pharmacol. 417:77-89 (2001).
Final Office Action for U.S. Appl. No. 14/962,170, filed Nov. 1, 2017, 8 Pages.
Finlayson-Pitts et al., A Fourier transform infrared spectrometry study of the reactions of phosphatidylcholines with gaseous N2 O5 and NO2. Toxicol. Appl. Pharmacol. 89:438-448 (1987).
Fisher, D.A et al., (1998) "Isolation and Characterization of PDE9A, a Novel Human cGMP-specific Phosphodiesterase" J_Boil_Chem_ 273(25):15559-15564.
Fiuza et al., From the characterization of the four serine/threonine protein kinases (PknA/B/G/L) of corynebacterium glutamicum toward the role of PknA and PknB in cell division. J Biol. Chem. 283(26):18099-18112 (2008).
Forman et al., 15-Deoxy-A 12 14- prostaglandin J2 is a ligand for the adipocyte determination factory PPAR gamma. Cell 83:803-812 (1995).
Freeman et al., Nitro-fatty acid formation and signaling. J of Biol. Chem. 283(23):15515-15519 (2008).
Freshney, Culture of Animal Cells. A Manual a/Basic Technique 1983, Alan R. Liss, Inc., New York, 1-6 (1983).
Fu et al., Oleylethanolamide regulates feeding and body weight through activation of the nuclear receptor PPAR-a. Nature 425:90-93 (2003).
Furstner et al., Total synthesis of epohelmin b and its analogues. Chem. Asian J 3:310-318 (2008).
Galle et al., Pulmonary hypertension and pulmonary arterial hypertension: a clarification is needed. Eur Respir J. 36(5):986-990 (2010).
Gallon et al., The identification of the allylic nitrite and nitro derivatives of methyl linoleate and methyl linolenate by negative chemical ionization mass spectroscopy. Lipids 28(2):125-133 (1993).
Gallon et al., The reaction of low levels of nitrogen dioxide with methyl linoleate in the presence and absence of oxygen. Lipids 29(3):171-176 (1994).
Garde, I., Complexa, Inc. Completes $13 Million Series B Financing to Further Advance Clinical Development of CXA-10. FierceBiotech, Jun. 4, 2014, pp. 1-2 (2014).
Gavin III et al., Reducing cardiovascular disease risk in patients with type 2 diabetes: a message from the National Diabetes Education Program. Am. Fam. Physician 68(8):1569-15674 (2003).
Geiger, S.S. et al., Chrono-immunology: progress and challenges in understanding links between the circadian and immune systems. Immunology 146(3):349-358 (2015).
Genders et al., cGMP phosphodiesterase inhibition improves the vascular and metabolic actions of insulin in skeletal muscle. Am J Physiol Endocrinol Metab. 301(2):E342-E350 (2011).
Gladwin et al., Role of circulating nitrite and S-nitrosohemoglobin in the regulation of regional blood flow in humans. Proc. Natl. Acad. Sci. 97(21):11482-11487 (2000).
Gladwin et al., S-nitrosohemoglobin is unstable in the reductive erythrocyte environment and lacks O2/NO linked allosteric function. J Biol. Chem. 277(31):27818-27828 (2002).
Gladwin et al., The emerging biology of the nitrite anion. Nat. Chem. Biol. 1(6):308-314 (2005).
Glauser et al., The inflammatory response and tissue damage. The example of renal scars following acute renal infection. Pediatric Nephrology 1(4):615-622 (Abstract from PubMed website Jan. 22, 2016) (1987).
Goodman & Gilman's The Pharmacological Basis a/Therapeutics, Ninth Edition 1996, McGraw-Hill Book Company, New York, Appendix II, 1707-1711 (TOC) (1996).
Goodman & Gilman's The Pharmacological Basis a/Therapeutics, Sixth Edition 1980, MacMillan Publishing Co., New York (TOC) (1980).
Goodman & Gilman's The Pharmacological Basis a/Therapeutics, Tenth Edition 2001, McGraw-Hill Book Company, New York (TOC) (2001).
Gorczynski et al., Evaluation of nitroalkenes as nitric oxide donors. Bioorg. Med. Chem. Lett. 17:2013-2017 (2007).
Gorczynski et al., Regio-and stereospecific synthesis and nitric oxide donor properties of (E)-9- and (E)-10-nitrooctadec-9-enoic acids. Org. Lett. 8(11):2305-2308 (2006).
Gregory et al., 5-HT3 Receptor antagonists for the prevention of chemotherapy-induced nausea and vomiting: a comparison of their pharmacology and clinical efficacy. Drugs 55(2):173-189 (1998).
Grisham, Myoglobin-catalyzed hydrogen peroxide dependent arachidonic acid peroxidation. Free Radic. Biol. Med. 1:227-232 (1985).
Groeger et al., Cyclooxygenase-2 generates anti-inflammatory mediators from omega-3 fatty acids. Nat. Chem. Bio. 6:433-441 (2010).
Groeger et al., Discovery, structural characterization and quantification of novel inflammatory-induced electrophilic fatty acid derivatives. Free Radical Bio. & Med. 45(1):S134 (2008).
Groeger et al., Signaling actions of electrophiles: anti-inflammatory therapeutic candidates. Malec. Interven. 10(1):39-50 (2010).
Guindon et al., A simple, fast, and accurate algorithm to estimate large phylogenies by maximum likelihood. Systematic Bio. 52(5):696-704 (2003).
Guindon et al., Estimating maximum likelihood phylogenies with PhyML. Methods in Molecular Bio. 537:113-137 (2009).
Guo et al., Atypical PKCI transduces electrophilic fatty acid signaling in pulmonary epithelial cells. Nitric Oxide 25:366-372 (2011).

(56) References Cited

OTHER PUBLICATIONS

Gutierrez et al., Nitric oxide regulation of superoxide-dependent lung Injury: oxidant-protective actions of endogenously produced and exogenously administered nitric oxide. Free Radic. Biol. Med. 21(1):43-52 (1996).
Hackam, et al., Translation of Research Evidence From Animals to Humans;JAMA, 296(14), 2006, 1731-1732.
Hartmann et al., A randomized trial comparing the nephrotoxicity of cisplatin/ifosfamide-based combination chemotherapy with or without amifostine in patients with solid tumors. Investigational New Drugs 18:281-289 (2000).
Hogg et al., Inhibition of low-density lipoprotein oxidation by nitric oxide potential role in atherogenesis. FEBS Lett. 334(2):170-174 (1993).
Hogg et al., Reactions of nitric oxide with nitronyl nitroxides and oxygen: prediction of nitrate formation by kinetic simulation. Free Radic. Res. 22(1):47-56 (1995).
Hogg, The biochemistry and physiology of S-nitrosothiols. Annu. Rev. Pharmacol. Toxicol. 42:585--600 (2002).
Ichikawa et al., Nitroalkenes suppress lipopolysaccharide-induced signal transducer and activator of transcription signaling in macrophages: a critical role of mitogen-activated protein kinase phosphatase 1. Endocrinology 149(8):4086-4094 (2008).
Ignarro et al., Endothelium-derived relaxing factor from pulmonary artery and vein possesses pharmacologic and chemical properties identical to those of nitric oxide radical. Circ. Res. 61:866-879 (1987).
Ignarro et al., Pharmacological evidence that endothelium-derived relaxing factor is nitric oxide: use of pyrogallol and superoxide dismutase to study endothelium-dependent and nitric oxide-elicited vascular smooth muscle relaxation. J Pharmacol. Exp. Ther. 244(1):181-189 (1988).
Iles et al., Fatty acid transduction of nitric oxide signaling: nitrolinoleic acid mediates protective effects through regulation of the ERK pathway. Free Radic. Biol. Med. 46:866-875 (2009).
International Application No. PCT/US2017/040160 International Search Report and Written Opinion dated Oct. 9, 2017.
International Preliminary Report on Patentability for PCT/US2009/0047825 dated Jan. 6, 2011.
International Preliminary Report on Patentability issued in corresponding PCT/US2012/051304, 1-8 (dated Mar. 6, 2014).
International Preliminary Report on Patentability issued in corresponding PCT/US2012/059722, 1-9 (dated Apr. 24, 2014).
International Search Report and Written Opinion dated Dec. 4, 2009, in corresponding PCT/US2009/002628.
International Search Report and Written Opinion dated Apr. 21, 2015 corresponding to PCT/US2014/065203.
International Search Report and Written Opinion dated Aug. 19, 2013 corresponding to PCT/US2012/059722.
International Search Report and Written Opinion dated Jul. 13, 2011 corresponding to PCT/US2010/051059.
International Search Report and Written Opinion dated Jun. 2, 2013 corresponding to PCT/US2013/024476.
International Search Report and Written Opinion dated Jun. 30, 2009 corresponding to PCT/US2009/041018.
International Search Report and Written Opinion dated Mar. 23, 2012 corresponding to PCT/US2011/04201.
International Search Report and Written Opinion dated Mar. 5, 2010 corresponding to PCT/US2009/047825.
International Search Report and Written Opinion dated Nov. 1, 2012 corresponding to PCT/US2012/051304.
International Search Report and Written Opinion dated Nov. 27, 2014 corresponding to PCT/US2014/047073.
International Search Report and Written Opinion dated Oct. 12, 2006 corresponding to International Patent Application No. PCT/US2005/014305.
International Search Report and Written Opinion dated Oct. 24, 2008 corresponding to International Patent Application No. PCT/US2008/009274.
International Search Report PCT/US2010/002141 dated Nov. 24, 2010.
Itoh et al., Synthesis of docosahexaenoic acid derivatives designed as novel PPARy agonists and antidiabetic agents. Bioorg.Med. Chem. 14:98-108 (2006).
Janero et al., Differential nitros(yl)ation of blood and tissue constituents during glycerol trinitrate biotransformation in vivo. PNAS 101(48):16958-16963 (2004).
Jasuja et al.: PDE-9 Inhibition Combined with Hydroxyurea Is Beneficial in Vaso-Occlusive Crisis in Mouse Model of Sickle Cell Disease. The American Society of Hematology; 124(21):2694 (2014).
Jeong et al., Fenofibrate prevents obesity and hypertriglyceridemia in low-density lipoprotein receptor-null mice. Metabolism 53(5):607-613 (2004).
Jimenez-Estrada et al., Allyic nitration of 3 -sitosterol and cholesterol acetate: preparation of 7-nitro derivatives. Steroid 62:500-503 (1997).
Jordan, V. C., "Tamoxifen: a most unlikely pioneering medicine" Nature Reviews: Drug Discovery, 2, 2003, 205.
Jourd'Heuil et al., The oxidative and nitrosative chemistry of the nitric oxide/superoxide reaction in the presence of bicarbonate. Arch. Biochem. Biophys. 365(1):92-100 (1999).
Junping et al., Pharmacokinetics and antitumor effects of vincristine carried microemulsions composed of PEG-lipid, oleic acid, vitamin E and cholesterol. Int. J Pharm. 251(1-2):13-21, Abstract (2003).
Kalliokoski, A. et al., Impact of OATP transporters on pharmacokinetics. British Journal of Pharmacology 158(3):693-705 (2009).
Kansanen et al., Nrf2-dependent and -independent responses to nitro-fatty acids in human endothelial cells: identification of heat shock response as the major pathway activated by nitro-oleic acid. J Biol. Chem. 284(48):33233-33241 [1-34] (2009).
Karp et al., Clinical and biologic activity of the farnesyltransferase inhibitor RI 15777 in adults with refractory and relapsed acute leukemias: a phase 1 clinical-laboratory correlative trial. Blood 97(11):3361-3369 (2001).
Katoh et al., Recent developments in the MAFFT multiple sequence alignment program. Briefings in Bioinformatics 9(4):286-298 (2008).
Kelley et al.: Fatty acid nitroalkenes ameliorate glucose intolerance and pulmonary hypertension in high-fat diet-induced obesity. Cardiovascular Research. 101(3):352-363 (2014).
Kelley et al., Nitro-oleic acid, a novel and irreversible inhibitor of xanthine oxidoreductase. J Biol. Chem. 283(52):36176-36184 (2008).
Khoo et al., Activation of vascular endothelial nitric oxide synthase and heme oxygenase-1 expression by electrophilic nitro-fatty acids. Free Radic. Bio. Med. 48:230-239 (2010).
Khoo et al., Electrophilic nitro-fatty acids: anti-inflammatory mediators in the vascular compartment. Curr. Opn. Pharml. 10:179-184 (2010).
Kim et al., Bisubstrate ketone analogues as serotonin N-acetyltransferase inhibitors. J Med. Chem. 44(15):2479-2485 (2001).
Kim et al., The effect of PPAR-y agonist on glucose metabolism and insulin sensitivity in non-obese type 2 diabetic rat models. Diabetes Jun. 1, 2006, American Diabetes Association 55: Suppl. 1:A483(2006).
Kissner et al., Formation and properties of peroxynitrite as studied by laser flash photolysis, high-pressure stopped-flow technique, and pulse radiolysis. Chem. Res. Toxicol. 10:1285-1292 (1997).
Kliewer et al. A prostaglandin J2 metabolite binds peroxisome proliferatory-activated receptor y and promotes adipocyte differentiation. Cell 83:813-819 (1995).
Kliewer et al., Fatty acids and eicosanoids regulate gene expression through direct interactions and peroxisome proliferator-activated receptors a and y Proc. Natl. Acad. Sci. 94:4318-4323 (1997).
Klinke et al.: Protective Effects of 10-nitro-oleic Acid in Hypoxia-Induced Murine Model of Pulmonary Hypertension. American Journal of Respiratory Dell and Molecular Biology. 51(1):155-162(2014).
Kobayshi, The reaction of nitrogen dioxide with lung surface components: the reaction with cis-9-octadecenoic acid. Chemosphere 12(9/10):1317-1325 (1983).
Koenitzer et al., Redox signaling in inflammation: interactions of endogenous electrophiles and mitochondria in cardiovascular disease. Ann. NY Acad. Sci. 1203:45-52 (2010).

(56) References Cited

OTHER PUBLICATIONS

Konig, J. et al., Transporters and drug-drug interactions: important determinants of drug disposition and effects. Pharmacological Review 65(3):944-66 (2013).

Kunin, Urinary tract infections in females. Clinical Infectious Diseases 18:1-10 (1994).

Lai et al., Reactions of dinitrogen pentoxide and nitrogen dioxide with 1-palmitoyl-2-oleoyl- sn-glycero-3-phosphocholine. Lipids 26(4):306-314. Abstract (1991).

Larfars et al., Activation of nitric oxide release and oxidative metabolism by leukotrienes B4, C4, and D4 in human polymorphonuclear leukocytes. Blood 93(4):1399-1405 (1999).

Lee et al., Peroxisome proliferators-activated receptor-yin macrophage lipid homeostasis. Trends Endocrinol. Metab. 13(8):331-335 (2002).

Lee et al., Rosiglitazone ameliorates cisplatin-induced renal injury in mice. Nephrol. Dial. Transplant. 21:2096-2105 (2006).

Levy et al., Lipid mediator class switching during acute inflammation: signals in resolution. Nat. Immunol. 2(7):612-619 (2001).

Li et al., Differential inhibition of macrophage foam-cell formation and atherosclerosis in mice by PPAR alpha, betta/delta, and gamma. J Clin. Invest. 114(11):1564-1576 (2004).

Li et al., Molecular recognition of nitrated fatty acids by PPAR gamma. Nat. Struct. Mol. Biol. 15(8):865-867 [1-3] (2008).

Li et al., PPARa ligand protects during cisplatin-induced acute renal failure by preventing inhibition of renal FAO and PDC activity. Am. J Physiol. Renal Physiol. 286:F572-F580 (2004).

Lim et al., Nitrolinoleate, a nitric oxide-derived mediator of cell function: synthesis, characterization, and vasomotor activity. Proc. Natl. Acad. Sci. 99(25):15941-15946 (2002).

Lima et al., Characterization of linoleic acid nitration in human blood plasma by mass spectrometry. Biochem. 41(34):10717-10722 (2002).

Lima et al., Cholesteryl nitrolinoleate, a nitrated lipid present in human blood plasma and lipoproteins. J Lipid Res. 44:1660-1666 (2003).

Lima et al., Nitrated lipids decompose to nitric oxide and lipid radicals and cause vasorelaxation. Free Radical Bio. Med., Elsevier Sciences 39(4):532-539 (2005).

Liu et al., Accelerated reaction of nitric oxide with O2 within the hydrophobic interior of biological membranes. Proc. Natl. Acad. Sci. 95:2175-2179 (1998).

Liu et al., Combined losartan and nitro-oleic acid remarkably improves diabetic nephrophaty in mice. Am. J Physiol. Renal Physiol. 305:F1555-F1562 (2013).

Liu et al., Nitrol-oleic acid protects the mouse kidney from ischemia and reperfusion injury. Am. J Physiol. Renal Physiol. 295(4):F942-F949 (2008).

Liu et al.: Nitro-oleic acid protects against adriamycin-induced nephropathy in mice. Am J Physiol Renal Physiol. 305(11):F1533-F1541 (2013).

Lopez et al., Second generation of a-tocopherol analogs-nitric oxide donors: synthesis, physiochemical, and biological characterization. Bioorg. Med. Chem. 15:6262- 6272 (2007).

Loytynoja et al., An algorithm for progressive multiple alignment of sequences with insertions. PNAS 102(30):10557-10562 (2005).

Lundberg et al., Nitrate and nitrite in biology, nutrition and therapeutics. Nat. Chem. Bio. 5(12):865-869 (2009).

Luzzio, The Henry reaction: recent examples. Tetrahedron 57:915-945 (2001).

Ma et al., Hydrohalogenation reaction of substituted 1,2-allenic carboxylic acids, esters, amides, nitriles, and diphenyl phosphine oxides. Synthesis (5):713-730 (2001).

Manini et al., Chemistry of nitrated lipids: remarkable instability of 9-nitrolinoleic acid in neutral aqueous medium and a novel nitronitrate ester product by concurrent autoxidation/nitric oxide-release pathways. J Org Chem. 73(19):7517-7525 (2008).

March, Effects of Structure on Reactivity. Advanced Organic Chemistry (1977 edition), McGraw-Hill Book Company, New York, 251-259 (1977).

Marnett et al., Regulation of prostaglandin biosynthesis by nitric oxide is revealed by targeted deletion of inducible nitric-oxide synthese. J Biol. Chem. 275(18):13427-13430 (2000).

Marshall et al., Nitrosation and oxidation in the regulation of gene expression. FASEB Journal 14:1889-1900 (2000).

Martini, S. et al., Integrative biology identifies shared transcriptional networks in CKD. Journal of the American Society of Nephrology 25:2559-2572 (2014).

Marx et al., Peroxisome proliferator-activated receptors and atherogenesis: regulators of gene expression in vascular cells. Circ. Res. 94(9):1168-1178 (2004).

McIntyre et al., Identification of an intracellular receptor for lysophosphatidic acid (LPA): LPA is a transcellular PPARy agonist. Proc. Natl. Acad. Sci. 100(1):131-136 (2003).

McLean, Iodostarin. Archives of Internal Medicine 10:509 (1912).

Mehats, C. et al., (2002) "Cyclic Nucleotide Phosphodiesterases and their Role in Endocrine Cell Signaling" Trends In Endocrinol. & Metab. 13:29-35.

Menendez et al., Effects of gama-linolenic acid and oleic acid on paclitaxel cytotoxicity in human breast cancer cells. European J of Cancer (Oxford, England: 1990) 37(3):402-213 (2001).

Messerschmidt et al., Handbook of Metalloproteins 2001, Hoboken, NJ, John Wiley & Sons, Inc. (abstract) (2001).

Metabolite definition at https://www.nlm.nih.gov/medlineplus/ency/article/002258.htm (retrieved from the internet Jan. 21, 2016).

Meyer et al., Uremia. New Engl. J Med. 357:1316-1325 (2007).

Miguel et al., Inhibition of phosphodiesterase 9A reduces cytokine-stimulated in vitro adhesion of neutrophils from sickle cell anemia individuals. Inflammation Research 60(7):633-42 (2011).

Minghetti, Cyclooxygenase-2 (COX-2) in inflammatory and degenerative brain diseases. J Neuropathol. Exp. Neural. 63(9):901-910 (2004).

Miranda et al., The Chemical Biology of nitric oxide, nitric oxide: Biology and Pathobiology 2000, Academic Press, San Diego, 41-55 (2000).

Mitschke et al., 9- and 10-Nitro-oleic acid do not interfere with the GC-MS quantitative determination of nitrite and nitrate in biological fluids when measured as their pentalfluorobenzyl derivatives. J Chromatography B. 85(1):287-291 (2007).

Montuschi et al., Isoprostanes: markers and mediators of oxidative stress. FASEB J. 18:1791-1800 (2004).

Morgan et al., Use of animal models of human disease for nonclinical safety assessment of novel pharmaceuticals. Toxicol. Pathol. 41(3):508-518 (2013).

Mukherjee et al., A selective peroxisome proliferator-activated receptor-gamma (PPARgamma) modulator blocks adipocyte differentiation but stimulates glucose uptake in 3T3-L1 adipocytes. Mol. Endocrinol. 14:1425-1433. (2000).

Nadtochiy et al. Mitochondrial nitroalkene formation and mild uncoupling in ischaemic preconditioning: implications for cardioprotection. Card. Res. Adv. Access 2008, 1-8 (2008).

Nadtochiy et al., Nitroalkenes confer acute cardioprotection via adenine nucleotide transloase I. J Biol. Chem. 287(5):3573-3580 (2012).

Nagano et al., Use of tacrolimus, a potent antifibrotic agent, in bleomycin-induced lung fibrosis. Eur. Respir. J. 27:460-469 (2006).

Nagasaki et al., Phosphodiesterase type 9 (PDE9) in the human lower urinary tract: an immunohistochemical study. BJU International 109(6):934-940 (2012).

Nagy et al., Oxidized LDL regulates macrophage gene expression through ligand activation of PPARy. Cell 93:229-240 (1998).

Napolitano et al., Acid-induced structural modifications of unsaturated fatty acids and phenolic olive oil constituents by nitrite ions: a chemical assessment. Chem. Res. Toxicol.17:1329-1337 (2004).

Napolitano et al., Acid-promoted reactions of ethyl linoleate with nitrite ions: formation and structural characterization of isomeric nitroalkene, nitrohydroxy, and novel 3-nitro-1,5-hexadiene and 1,5-Dinitro-1,3-pentadiene products. J Org. Chem. 65(16):4853-4860 (2000).

Napolitano et al., The acid-promoted reaction of ethyl linoleate with nitrite. New insights from 15N-labelling and peculiar reactivity of a model skipped diene. Tetrahedron 58:5061-5067 (2002).

(56) References Cited

OTHER PUBLICATIONS

Narayan et al., Serine threonine protein kinases of mycobacterial genus: phylogeny to function. Physiological Genomics 29:66-75 (2007).
Nathan, Nitric oxide as a secretory product of mammalian cells. FASEB J. 6:3051-3064 (1992).
Newman et al., Optimized thiol derivatizing reagent for the mass spectral analysis of distributed epoxy fatty acids. J Chromato. 925:223-240 (2011).
Niebisch et al., Corynebacterial protein kinase G controls 2-oxoglutarate dehydrogenase activity via the phosphorylation status of the Odhl protein. J Biol. Chem. 281(18):12300-12307 (2006).
NIH US National Library of Medicine, FIRSTx—A Study of Oral CXA-10 in Primary Focal Segmental Glomerusclerosis (FSGS). NCT03422510, Feb. 5, 2018, pp. 1-10 (2018).
Notredame et al., T-Coffee: A novel method for fast and accurate multiple sequence alignment. J Malec. Bio. 302:205-217 (2000).
Nott et al., An intramolecular switch regulates phosphoindependent FHA domain interactions in *Mycobacterium tuberculosis*. Sci. Signaling 2(63):ra 12 (2009).
O'Donnell et al., 15-Lipoxygenase catalytically consumes nitric oxide and impairs activation of guanylae cyclase. J Biol. Chem. 274(29):20083-20091 (1999).
O'Donnell et al., Catalytic consumption of nitric oxide by prostagladin H synthase-l regulates platelet function. J Biol. Chem. 275(49):38239-38244 (2000).
O'Donnell et al., Interactions between nitric oxide and lipid oxidation pathways: implications for vascular disease. Circ. Res. 88:12-21 (2001).
O'Donnell et al., Nitration of unsaturated fatty acids by nitric oxide-derived reactive nitrogen species peroxynitrite, nitrous acid, nitrogen dioxide, and nitronium ion. Chem. Res. Toxicol. 12(1):83-92 (1999).
O'Donnell et al., Nitric oxide inhibition of lipid peroxidation: kinetics of reaction with lipid peroxyl radicals and comparison with a-tocopherol. Biochem. 36(49):15216-15223 (1997).
O'Hare et al., Regulation of glutamate metabolism by protein kinases in mycobacteria. Mol. Microbio. 70(6):1408-1423 (2008).
Ono et al., A convenient procedure for the conversion of E-nitroalkenes to (Z)-nitroalkenes via erythro- -nitroselenides. J Chem. Soc., Chem Commun. 20:1550-1551 (1987).
Ortiz-Lombardia et al., Crystal structure of the catalytic domain of the PknB serine/threonine kinase from *Mycobacterium tuberculosis*. J Biol. Chem. 278(15):13094-13100 (2003).
Padmaja, The reaction of nitric oxide with organic peroxyl radicals. Biochem. Biophvs. Res. Commun. 195(2):539-544 (1993).
Park et al., Modulation of tumor necrosis factor-related apoptosis-inducing ligand- induced apoptosis by chemotherapy in thyroid cancer cell lines. Thyroid 13(12):1103-1110 (2003).
Pawliczak et al., 85-kDa cytosolic phospholipase A2 mediates peroxisome proliferator-activated receptory activation in human lung epithelial cells. J Biol. Chem. 277:33153-33163 (2002).
PCT International Search Report and Written Opinion for PCT/US16/55206, dated Dec. 23, 2016.
PCT/CN2012/070718 International Search Report and Written Opinion dated Sep. 13, 2012.
PCT/EP2012/069936 International Search Report and Written Opinion dated Nov. 14, 2012.
PCT/EP2013/051451 International Search Report and Written Opinion dated Feb. 26, 2013.
PCT/EP2016/065964 International Search Report and Written Opinion dated Aug. 11, 2016.
PCT/US2018/034566 International Preliminary Report on Patentability dated Nov. 26, 2019.
PCT/US2018/034566 International Search Report and Written Opinion dated Aug. 21, 2018.
PCT/US2019/033835 International Preliminary Report on Patentability dated Dec. 1, 2020.
PCT/US2019/033835 International Search Report and Written Opinion dated Aug. 9, 2019.
PCT/US2019/048898 International Preliminary Report on Patentability dated Mar. 2, 2021.
PCT/US2019/048898 International Search Report and Written Opinion dated Nov. 25, 2019.
PCT/US2020/026696 International Search Report and Written Opinion dated Jun. 30, 2020.
PCT/US2020/031659 International Search Report and Written Opinion dated Jul. 31, 2020.
PCT/US2021/045765 Invitation to Pay Additional Fees dated Oct. 26, 2021.
Pharma Medica 20(5):199-210 (2002) (in Japanese with brief English relevance).
Pryor et al., Reaction of nitrogen dioxide with alkenes and poly-unsaturated fatty acids: addition and hydrogen abstraction mechanisms. J Amer. Chem. Soc. 104:6685- 6692 (1982).
PubChem CID 71550282 https://pubchem.ncbi.nlm.nih.gov/compound/71550282 (2013).
Punchard et al., The Journal of Inflammation Editorial; The Journal of Inflammation September, BioMed Central, 1(1):1-4 (2004).
Quijano et al., Reaction of peroxynitrite with Mn-superoxide dismutase: role of the metal center in decomposition kinetics and nitration. J of Biol. Chem. 276(15):11631-11638 (2001).
Radi et al., Peroxynitrite oxidation of sulfhydryls: the cytotoxic potential of superoxide and nitric oxide. J Biol. Chem. 266(7):4244-4250 (1991).
Radi et al., Peroxynitrite reactions with carbon dioxide-bicarbonate. Methods Enzymol. 301(37):353-367 (1999).
Ranu et al., Highly selective reduction of conjugated nitroalkenes with zinc borohydride in DME. Tetrahedron Letters 32(29):3579-3582 (1991).
Rassaf et al., Concomitant presence of n-nitroso and s-nitroso proteins in human plasma. Free Radic. Biol. Med. 33(11):1590-1596 (2002).
Rassaf et al., NO adducts in mammalian red blood cells: too much or too little? Nat. Med. 9(5):481-482 (2003).
Reema et al.: PDE-9 Inhibition combined with hydroxyurea is beneficial in vaso-occlusive crisis in mouse model of sickle cell disease. Blood. 124(21):1-2 (2014).
Remington's Pharmaceutical Sciences 1990, 18th Ed. (TOC).
Rosen et al., PPARy: a nuclear regulator of metabolism, differentiation, and cell growth. J Biol. Chem. 276(1):37731-37734 (2001).
Rowe et al., Handbook of Pharma. Excipients 2006, 5th Ed., Great Britain: Pharmaceutical Press, American Pharmacists Association (2006).
Rubbo et al., Forum on nitric oxide: chemical events in toxicity. Nitric oxide regulation of tissue free radical injury. Chem. Res. Toxicol. 9(5):809-820 (1996).
Rubbo et al., Nitric oxide inhibition of lipoxygenase-dependent liposome and low-density lipoprotein oxidation: termination of radical chain propagation reactions and formation of nitrogen-containing oxidized lipid derivatives. Arch. Biochem. Biophys. 324(1):15-25 (1995).
Rubbo et al., Nitric oxide reaction with lipid peroxyl radicals spares a-tocopherol during lipid peroxidation. J Biol. Chem. 275(25):10812-10818 (2000).
Rubbo et al., Nitric oxide regulation of superoxide and peroxynitrite-dependent lipid peroxidation.J Biol. Chem. 269(42):26066-26075 (1994).
Rudnick et al., Contrast-induced nephropathy: How it develops, how to prevent it. Cleveland Clinic J Med. 73(1):75-87 (2006).
Rudolph et al., Cardiovascular consequences when nitric oxide and lipid signaling converge. Circ. Res. 105:511-522 (2009).
Rudolph et al., Endogenous generation and protective effects of nitro-fatty acids in murine model of focal cardiac ischaemia and reperfusion. Cardiov. Res. Advance Access 1-12 (2009).
Rudolph et al., Nitro-fatty acid metabolome: saturation, desaturation, -oxidation, and protein adduction. J Biol. Chem. 284(3):1461-1473 (2009).
Rudolph et al., Nitro-fatty acids reduce atherosclerosis in apolipoprotein e-deficient mice. Ather. Thromb. Vasc. Bio. 30:938-945 (2010).
Rudolph et al., Transduction of redox signaling by electrophile-protein reactions. Science Signaling. 2(90):re7 [1-13] (2009).

(56) References Cited

OTHER PUBLICATIONS

Ryan et al., Diabetes and the Mediterranean diet: a beneficial effect of oleic acid on insulin sensitivity, adipocyte glucose transport and endothelium-dependent vasoreactivity. Q. J Med. 93:85-91 (2000).
Saffer et al., Choosing drug therapy for patients with hyperlipidemia. Am. Fam. Physic. 61(11):3371-3382 (2000).
Sarver et al., Analysis of peptides and proteins containing nitrotyrosine by matrix-assisted laser desorption/ionization mass spectrometry. J Am. Soc. Mass Spectrom. 12(4):439-448 (2001).
Satyanarayana et al., Steroselective synthesis of diacids by the nickel cyanide and phase-transfer-catalyzed carbonylation of alkynols. Novel dependency of product stereochemistry and optimum stirring speed on the nature of the phase-transfer agent. Organometallics 10:804-807 (1991).
Saulnier-Blache et al., A simple and highly sensitive radioenzymatic assay for lysophosphatidic acid quantification. J Lipid Res. 2000, vol. 41, 1947-1951 (2000).
Scarpini et al., Treatment of Alzheimer's disease: current status and new perspectives. Lancet Neural. 2:539-547 (2003).
Scherr et al., Structural basis for the specific inhibition of protein kinase G, a virulence factor of mycobacterium tuberculosis. PNAS 104(29):12151-12156 (2007).
Schopfer et al., Covalent peroxisome proliferator-activated receptor gamma adduction by nitro- fatty acids: selective ligand activity and anti-diabetic signaling actions. J Biol. Chem. 285(16):12321-12333 (2010).
Schopfer et al., Detection and quantification of protein adduction by electrophilic fatty acids: mitochondrial generation of fatty acid nitroalkene derivatives. Free Radic. Biol. Med. 46:1250-1259 (2009).
Schopfer et al., Fatty acid transduction of nitric oxide signaling. Nitrolinoleic acid is a hydrophobically stabilized nitric oxide donor. J Biol. Chem. 280(19):19289-19297 (2005).
Schopfer et al., Nitrolinoleic acid: an endogenous peroxisome proliferator-activated receptor y ligand. Proc. Natl. Acad. Sci. 102(7):2340-2345 (2005).
Schopfer et al., NO-dependent protein nitration: a cell signaling event or an oxidative inflammatory response? Trends Biochem. Sci. 28:646-654 (2003).
Sculptoreanu et al., Nitro-oleic acid inhibits firing and activates TRPV-1 and TRPAI-mediated inward currents in dorsal root ganglion neurons from adult male rats. J Pharm. Expt. Thera. 333(3):883-895 (2010).
Serhan et al., Anti-inflammatory actions of neuroprotectin DI/protectin DI and its natural stereoisomers: assignments of dihydroxy-containing docosatrienes. J Immunology 176:1848-1859 (2006).
Setiadi et al., Vitamin E models. Conformational analysis and stereochemistry oftetralin, choman, thiochroman and selenochroman. J Molecular Structure (Theochem) 594:161-172 (2002).
Shaner et al., Designing herbicide tolerance based on metabolic alteration: the challenges and the future. In Pesticide Biotransformation in Plants and Microorganisms (Hall, J. et al.); ACS Symposium Series 2000, American Chemical Society; Washington DC, 353-374 (2000).
Sharpless et al., A mild procedure for the conversion of epoxides to allylic alcohols. The first organoselenium reagent. J Am. Chem. Soc. 95(8):2697-2699 (1973).
Sieker et al., Rubredoxin in crystalline state. Methods Enzymol. 243:203-216 (1994).
Simopoulos et al., Omega-3 fatty acids in inflammation and autoimmune diseases. J Amer. College of Nutrition 21(6):495-505 (2002).
Smith, Prostanoid biosynthesis and mechanisms of action. Am. Physiol. Soc. 263:F181-F191 (1992).
Snider et al., Oxidative and dehydrative cyclizations of nitroacetate esters with Mn (OAC). Tetrahedron 58(39):7821-7827 (2002).
Soding et al., HHsenser: exhaustive transitive profile search using HMM-HMM comparison. Nucleic Acids Res. 34:W374-378 (2006).
Strowig et al., Combination therapy using metformin orthiazolidinediones and insulin in the treatment of diabetes mellitus. Diabetes, Obesity, and Metabolism 7:633-641 (2005).
Subczynski et al., Permeability of nitric oxide through lipid bilayer membranes. Free Radic. Res. 24:343-349 (1996).
Szekely et al., A novel drug discovery concept for tuberculosis: inhibition of bacterial and host cell signaling. Immun. Letters 116(2):225-231 (2008).
Szoka et al., Comparative properties and methods of preparation of lipid vesicles (liposomes). Annual Review of Biophysics and Bioengineering 9:467-508 (1980).
Tang et al., Nitroalkenes induce rat aortic smooth muscle cell apoptosis via activation of caspase-dependent pathways. Biochem. Biophvs. Res. Commun. 397:239-244 (2010).
Thatcher et al., Nitrates and NO release: contemporary aspects in biological and medicinal chemistry. Free Radic. Biol. Med. 37(8)1122-1143 (2004).
Thomas et al., The biological lifetime of nitric oxide: implications for the perivascular dynamics of NO and O2. Proc. Natl. Acad. Sci. 98(1):355-360 (2001).
Tiwari et al., Key residues in mycobacterium tuberculosis protein kinase G play a role in regulating kinase activity and survival in the host. J Biol. Chem. 284(40):27467-27479 (2009).
Tontonoz et al., mPPARy2: tissue-specific regulator of an adipocyte enhancer. Genes Dev. 8(10):1224-1234 (1994).
Tontonoz et al., Stimulation of adipogenesis in fibroblasts by PPARy2, a lipid-activated transcription factor. Cell 79:1147-1156 (1994).
Toth, High-density lipoprotein and cardiovascular risk. Circulation 109:1809-1812 (2004).
Trostchansky et al., Nitrated fatty acids: mechanisms of formation, chemical characterization, and biological properties. Free Rad. Biol. Med. 44:1887-1896 (2008).
Tsikas et al., Nitro-fatty acids occur in human plasma in the picomolar range: a targeted nitro-lipidomics GC-MS/MS study. Lipids 44:855-865. (2009).
Tzameli et al., Regulated production of a peroxisome proliferatory-activated receptor- gamma ligand during an early phase of adipocyte differentiation in 3T3-LI adipocytes. J Biol. Chem. 279(34):36093-36102 (2004).
United States Office Action, U.S. Appl. No. 15/283,887, filed Feb. 8, 2019, 24 pages.
United States Office Action, U.S. Appl. No. 15/283,887, filed Jun. 14, 2018, 21 pages.
United States Office Action, U.S. Appl. No. 15/283,887, filed Nov. 16, 2017, 11 pages.
U.S. Appl. No. 16/315,365 Office Action dated Jul. 9, 2020.
U.S. Appl. No. 16/315,365 Restriction Requirement dated Oct. 7, 2019.
U.S. Appl. No. 16/615,347 Office Action dated Oct. 16, 2020.
U.S. Appl. No. 16/615,347 Office Action dated Sep. 2, 2021.
U.S. Appl. No. 16/673,709 Restriction Requirement dated Jun. 9, 2020.
Van Beilen et al., Rubredoxins involved in alkane oxidation. J Biol. Chem. 184(6):1722-1732 (2002).
van der Staay, J.F et al. (2008) "The Novel Selective PDE9 Inhibitor BAY 73-6691 Improved Learning and Memory in Rodents" Neuropharma 55(5):908-918.
Vasil'ev et al., The action of nitrogen dioxide upon erucic acid. Lomonosova 5:50-58 (English abstract) (1995).
Verhoest et al., 2009, "Identification of a Brain Penetrant PDE9A Inhibitor Utilizing Prospective Design and chemical Enablement as a Rapic Lead Optimization Strategy", Journal of Medicinal Chemistry, vol. 52, No. 24, pp. 7946-7949.
Vickers et al., IGF-1 treatment reduces hyperphagia, obesity, and hypertension in metabolic disorders induced by fetal programming. Endocrinol. 142(9):3964-3973 (2001).
Vidwans et al., Differential modulation of prostaglandin H synthase-2 by nitric oxide- related species in intact cells. Biochem. 40:11533-11542 (2001).
Villacorta et al., Nitro-linoleic acid inhibits vascular smooth muscle cell proliferation via the Keap1/Nrf2 signaling pathway. Am. J Physiol. Heart Circ. Physiol. 293(1):H770-H776 [1-9] (2007).
Villacorta et al., PPARy and its ligands: therapeutic implications in cardiovascular disease. Clin. Sci. 116:205-218 (2009).

(56) References Cited

OTHER PUBLICATIONS

Villacorta, L. et al., Electrophilic nitro-fatty acids inhibit vascular inflammation by disrupting LPS-dependent TLR4 signaling in lipid rafts. Cardiovascular Research 98(1):116-124 (2013).

Villarino et al., Proteomic identification of *M. tuberculosis* protein kinase substrates: PknB recruits GarA, a FHA domain-containing protein, through activation loop-mediated Interactions. J Mol. Bio. 350(5):953-963 (2005).

'Virtual Chembook' in www.elmhurst.edu/-chm/vchembook/55 lfattyacids.html (retrieved Dec. 12, 2012).

Von Knethen et al., Activation of peroxisome proliferator-activated receptory by nitric oxide in monocytes/macrophages down-regulates p47phox and attenuates the respiratory burst. J Immunol. 169:2619-2626 (2002).

Walburger et al., Protein kinase G from pathogenic mycobacteria promotes survival within macrophages. Sci. 304:1800-1804 (2004).

Wang et al., Constitutive activation of peroxisome proliferator-activated receptor-y suppresses pro-inflammatory adhesion molecules in human vascular endothelial cells. J Biol. Chem. 277(37):34176-34181 (2002).

Wang et al., Effects of endogenous PPAR agonist nitro-oleic acid on metabolic syndrome in obese Zucker rats. PPAR Res. Art. ID 601562, 1-7 (2010).

Wang et al., Nitro-oleic acid protects against endotoxin-induced endotoxemia and multiorgan injury in mice. Am. J Physiol. Renal Physiol. 298:F754-F762 (2010).

Wang, H. et al., Nitrooleic acid attenuates lipid metabolic disorders and liver steatosis in DOCA-salt hypertensive mice. PPAR Research 2015:480348 [1-9] (2015).

Weber et al., Fragmentation of bovine serum albumin by pepsin. 1. The origin of the acid expansion of the albumin molecule. J Biol. Chem. 239(5):1415-1423 (1964).

Wehenkel et al., Mycobacterial Ser/Tur protein kinases and phosphatases: physiological roles and therapeutic potential. Biochemica et Biophysica Acta 1784(1):193-202 (2008).

Woodcock, Synthesis of nitrolipids. All four possible diastereomers of nitrooleic acids: (E)-and (Z)-, 9- and 10-nitro-octadec-9-enoic acids. Organic Letters 2006, 8(18):3931-3934 (2006).

Wright et al., Fatty acid transduction of nitric oxide signaling: Nitrolinoleic acid potently activates endothelial heme oxygenase 1 expression. PNAS 103(11)4299-4304 (2006).

Wright et al., Human heme oxygenase-1 induction by nitro-linoleic acid is mediated by cyclic AMP, AP-1, and e-box response element interactions. Biochem. J. 422(2):353-361 DOI:BJ20090339 [1-31] (2009).

Wunder, F. et al., (2005) "Charachertization of the First Potent and Selective PDE9 Inhibitor Using a cGMP Reporter sell Line" Mol. Pharmacol_68(6):1775-1781.

Xu et al., Lysophosphatidic acid as a potential biomaker for ovarian and other gynecologic cancers. JAMA 280:719-723 (1998).

Zhang et al., Lysophosphatidic acid induces neointima formation through PPARgamma activation. J Ex Med. 199(6):763-774 (2004).

Zhang et al., Nitro-oleic acid inhibits angiotensin II-induced hypertension. Circ. Res. 107:540-548 (2010).

Zhang et al., Selective disruption of PPARgamma2 impairs the development of adipose tissue and insulin sensitivity. Proc. Natl. Acad. Sci. 101(29):10703-10708 (2004).

Zhou, M. et al., (1994) "Role of Guanylyl Cyclase and cGMP-dependent Protein Kinase in Long-Term Potentiation" Nature 36(6472):635-639.

EP19853434.9 Supplementary European Search Report dated May 2, 2022.

PCT/US2020/031659 International Preliminary Report on Patentability dated Nov. 18, 2021.

PCT/US2021/045765 International Search Report and Written Opinion dated Jan. 11, 2022.

PCT/US202/1056696 International Invitation to Pay Additional Fees dated Dec. 16, 2021.

PCT/US2021/1056696 International Search Report and Written Opinion dated Feb. 24, 2022.

\* cited by examiner

PDE9 INHIBITORS WITH IMIDAZO TRIAZINONE BACKBONE AND IMIDAZO PYRAZINONE BACKBONE FOR TREATMENT OF PERIPHERAL DISEASES

REFERENCED TO RELATED APPLICATIONS

This application is a continuation of U.S. application Ser. No. 16/673,709, filed Nov. 4, 2019, which is a continuation of U.S. application Ser. No. 15/742,086, filed Jan. 5, 2018, now U.S. Pat. No. 10,513,524, issued Dec. 24, 2019, which is a 35 U.S.C. § 371 U.S. National Stage Entry of International Application No. PCT/EP2016/065964, filed Jul. 6, 2016, which claims the benefit of priority of DK Provisional Patent Application No. PA201500393, filed Jul. 7, 2015, DK Provisional Patent Application No. PA201500407, filed Jul. 10, 2015, and DK Provisional Patent Application No. PA201600209, filed Apr. 7, 2016, the contents of each are herein incorporated by reference in their entireties.

FIELD OF THE INVENTION

The present invention relates to cyclic guanylate monophosphate (cGMP)-specific phosphodiesterase type 9 inhibitors (hereinafter referred to as PDE9 inhibitors) of the form 3H-imidazo[5,1-f][1,2,4]triazin-4-ones or 7H-imidazo[1,5-a]pyrazin-8-ones and their use as a medicament for treatment of peripheral diseases. Moreover the invention relates to a pharmaceutical composition comprising 3H-imidazo[5,1-f][1,2,4]triazin-4-ones and 7H-imidazo[1,5-a]pyrazin-8-ones.

BACKGROUND OF THE INVENTION

Phosphodiesterases (PDEs) are a family of enzymes degrading cyclic nucleotides and thereby regulating the cellular levels of second messengers throughout the entire body. PDEs represent attractive drug targets, as proven by a number of compounds that have been introduced to clinical testing and the market, respectively. PDEs are encoded by 21 genes that are functionally separated into 11 families differing with respect to kinetic properties, substrate selectivity, expression, localization pattern, activation, regulation factors and inhibitor sensitivity. The function of PDEs is the degradation of the cyclic nucleotide monophosphates cyclic Adenosine MonoPhosphate (cAMP) and/or Guanosine MonoPhosphate (cGMP), which are important intracellular mediators involved in numerous vital processes including the control of neurotransmission and smooth muscle contraction and relaxation.

PDE9 is cGMP specific (Km cAMP is >1000× for cGMP) and is hypothesized to be a key player in regulating cGMP levels as it has the lowest Km among the PDEs for this nucleotide. PDE9 is expressed throughout the brain at low levels with the potential for regulating basal cGMP.

In the periphery, PDE9 expression peaks in prostate, intestine, kidney and haematopoietic cells opening for the therapeutic potential in various peripheral indications.

Benign prostate hyperplasia (BPH) is one of the most prevalent conditions in the aging male population and represents a major health problem (Ueckert S et al., Expert Rev Clin Pharmacol. 2013 May; 6(3):323-32). BPH results in the formation of large nodules in the periurethral region of the prostate, which could lead to urinary tract obstruction. BPH is predominantly the result of a stromal proliferative process, and a significant component of prostatic enlargement results from smooth-muscle proliferation. The current pharmacological treatment of BPH includes α1 adrenergic blockers, 5-α-reductase inhibitors and more recently the PDE5 inhibitor tadalafil. PDE5 inhibitors are known to mediate smooth muscle relaxation via increased cGMP levels. The cGMP specific PDE9 is expressed at high levels in the prostate and PDE9 inhibition may thus offer potential antiproliferative benefits for BPH.

PDE9 is widely distributed in the urothelial epithelium of human lower urinary tract and PDE9 inhibition may be beneficial in lower urinary tract dysfunctional epithelium (LUDE) disease (Nagasaki et al., BJU Int. 2012 March; 109(6):934-40). Dysfunctional lower urinary tract epithelium can affect the bladder, urethra, labia or vaginal introitus in women, and the prostatic ducts and urethra in men (Parsons L C et al., 2002).

PDE9 expression has been shown in murine corpus cavernosum and chronic PDE9 inhibition was demonstrated to result in amplified NO-cGMP mediated cavernosal responses and thereby opening for potential benefit in erectile dysfunction (DaSilva et al., Int J Impot Res. 2013 March-April; 25(2):69-73). Currently approved treatment for erectile dysfunction is the class of PDE5 inhibitors, increasing cGMP in the smooth muscle cells lining the blood vessels supplying the corpus cavernosum of the penis.

cGMP PDE inhibition has been shown to enhance muscle microvascular blood flow and glucose uptake response to insulin (Genders et al., Am J Physiol Endocrinol Metab. 2011 August; 301(2):E342-50). The targeting of cGMP specific PDE9, which is expressed in muscle and blood vessels may provide a promising avenue for enhancing muscle insulin sensitivity and thereby be beneficial for the treatment of type 2 diabetes.

PDE9 inhibition may represent a novel and first line treatment for Sickle Cell Disease (SCD), a genetic disorder leading to vaso-occlusive processes responsible for much of the mortality in SCD patients. SCD disease results from a point mutation in the hemoglobin (HBB) gene producing abnormal sickle hemoglobin (HbS), which polymerizes and creates rigid and sticky sickled red blood cells. Sickled red blood cells result in chronic inflammation, elevated cell adhesion, oxidative stress, endothelial dysfunction culminating in vaso-occlusive processes.

There is to date no cure for SCD. Treatment options include blood transfusion and treatment with the anti-cancer agent hydroxyurea. Blood transfusions correct anemia by increasing the number of normal, non-sickled red blood cells in circulation. Regular transfusion therapy can help prevent recurring strokes in children at high risk. Hydroxyurea has been approved for the treatment of SCD and shown to reduce the frequency of painful crisis and hospitalization. The mechanism by which hydroxyurea is hypothesized to ameliorate the symptoms of SCD is two-fold; a) increase in non-sickled fetal hemoglobin production and b) decrease in cell adhesion. Specifically, hydroxyurea a) increases fetal non-sickled haemoglobin production via cGMP signalling, which has been shown to result in increased red blood cell survival and b) increases nitric oxide and cGMP levels, thereby decreasing adhesion and increasing survival. In summary, the evidence to date supports the notion that that both mechanisms by which hydroxyurea promotes benefits in SCD are mediated via increased cGMP.

PDE9 is expressed specifically in the human haematopoietic system including neutrophils, reticulocytes erythroid and erythroleukaemic cells. Furthermore, SCD patients exhibit a marked and significant increase in PDE9 expression in reticulocytes and neutrophils (Almeida et al., Br J Haematol. 2008 September; 142(5):836-44). Evidence additionally demonstrates a link between PDE9 and cell adhesion since PDE9 inhibition results in the reversal of the increased adhesive properties of SCD neutrophils (Miguel et al., Inflamm Res. 2011 July; 60(7):633-42). The mechanism by which PDE9 inhibition decreases cell adhesion has been shown to be mediated via increased cGMP and decreased endothelial adhesion molecule expression. Importantly, in an animal model of SCD, the PDE9 inhibitor mediated decrease in cell adhesion had the functional effect of increased cell survival. In addition to demonstrating effects on decreased cell adhesion comparable to hydroxyurea, PDE9 inhibition results in increased fetal non-sickled haemoglobin production. Finally, Almeida and colleagues demonstrated that treatment with hydroxyurea combined with PDE9 inhibition in a mouse model of SCD leads to added benefit of PDE9 inhibitor in amplifying the cGMP elevating effects of hydroxyurea (Almeida et al., Blood. 2012 Oct. 4; 120(14):2879-88). In conclusion, PDE9 inhibition can modulate both the expression of fetal haemoglobin production as well as decrease cell adhesion, both mechanisms key for the treatment of SCD.

WO 2013/053690 discloses PDE9 inhibitors with imidazopyrazinone backbone for the use as a medicament, such as in the treatment of patients suffering from cognitive impairments, in particular cognitive impairments that relate to neurodegenerative diseases such as cortical dementia (e.g. Alzheimer's disease) or subcortical dementia, e.g. AIDS related dementia.

WO 2013/110768 discloses PDE9 inhibitors with imidazotriazinone backbone for the use as a medicament, such as in the treatment of patients suffering from cognitive impairments, in particular cognitive impairments that relate to neurodegenerative diseases such as cortical dementia (e.g. Alzheimer's disease) or subcortical dementia, e.g. AIDS related dementia.

WO 2012/040230 discloses PDE9 inhibitors with imidazotriazinone backbone for the use as a medicament in the treatment of PDE9 associated diseases, including CNS and neurodegenerative disorders.

WO 2008/139293 and WO 2010/084438 both disclose amino-heterocyclic compounds that are PDE9 inhibitors and their use in treating neurodegenerative and cognitive disorders.

SUMMARY OF THE INVENTION

There is a constant need for improved treatment of the peripheral diseases benign prostate hyperplasia (BPH), urinary tract dysfunctional epithelium disease, erectile dysfunction, type 2 diabetes and sickle cell disease (SCD) and for that purpose the use of PDE9 inhibitors may be very useful. Since PDE9 is expressed throughout the brain at with the potential basal cGMP and thus signalling cascades shown to regulate synaptic transmission, it is evidently important that PDE9 inhibitors for the treatment of peripheral diseases have a low blood brain barrier penetration (BBB penetration) to avoid potential centrally-mediated side effects.

The present invention provides novel PDE9 inhibitors that have been shown to have a low blood brain barrier penetration and thus may be particularly useful for the treatment of peripheral diseases such as benign prostate hyperplasia (BPH), urinary tract dysfunctional epithelium disease, erectile dysfunction, type 2 diabetes and sickle cell disease (SCD). Further, the PDE9 inhibitors of the present invention are significantly stronger PDE9 inhibitors than PDE1 inhibitors which is important as PDE1 is expressed in heart and testes and inhibition of these PDE1 isoforms is thought to be a potential cause of cardiovascular and reproductive side effects.

The following compounds are encompassed by the invention:

P1

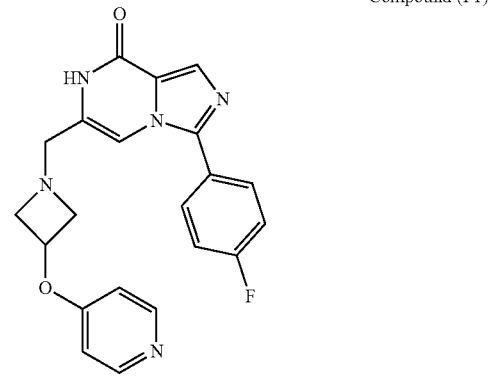

Compound (P1)

P2

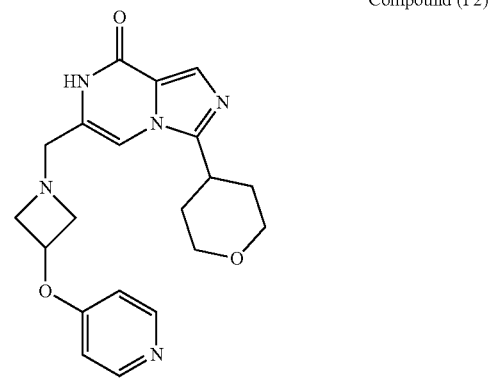

Compound (P2)

P3 (racemate)

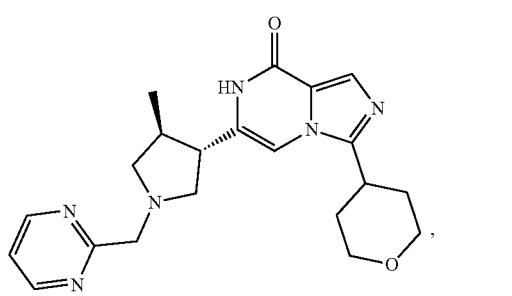

Compound (P3)

racemate and enantiomerically pure variants of compound P3.

P4

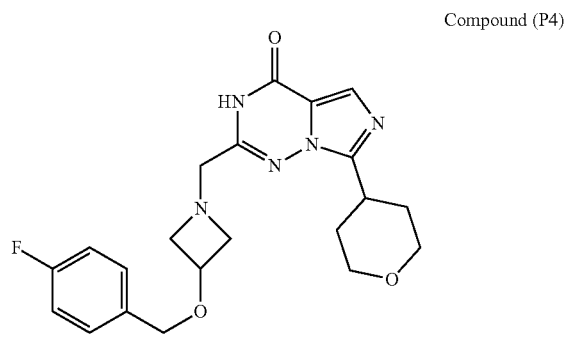

Compound (P4)

A further aspect of the invention is directed to synthesis of P1, P2, P3 and P4. A still further aspect of the invention is directed to the enantioselective synthesis of compound P3 comprising the conversion of the intermediate compound rac-35 to (S,S)-35.

DETAILED DESCRIPTION OF THE INVENTION

Embodiments of the Invention

Figure 1:
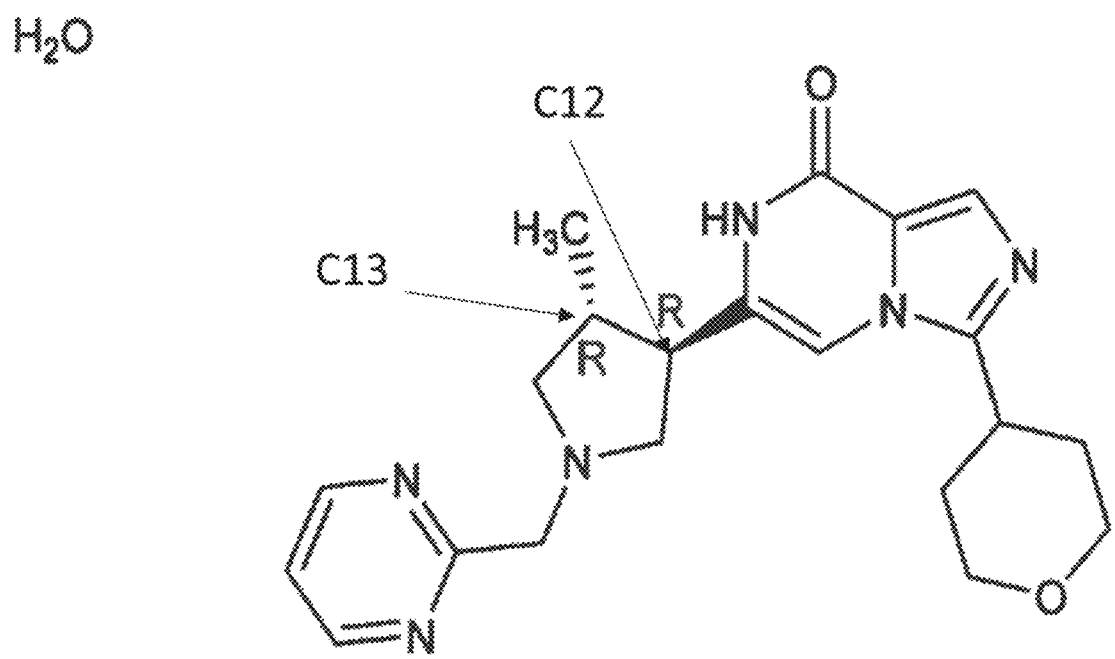
FIG. 1 shows the absolute stereochemistry of Compound P3 enantiomer 2 monohydrate.
Figure 2A:
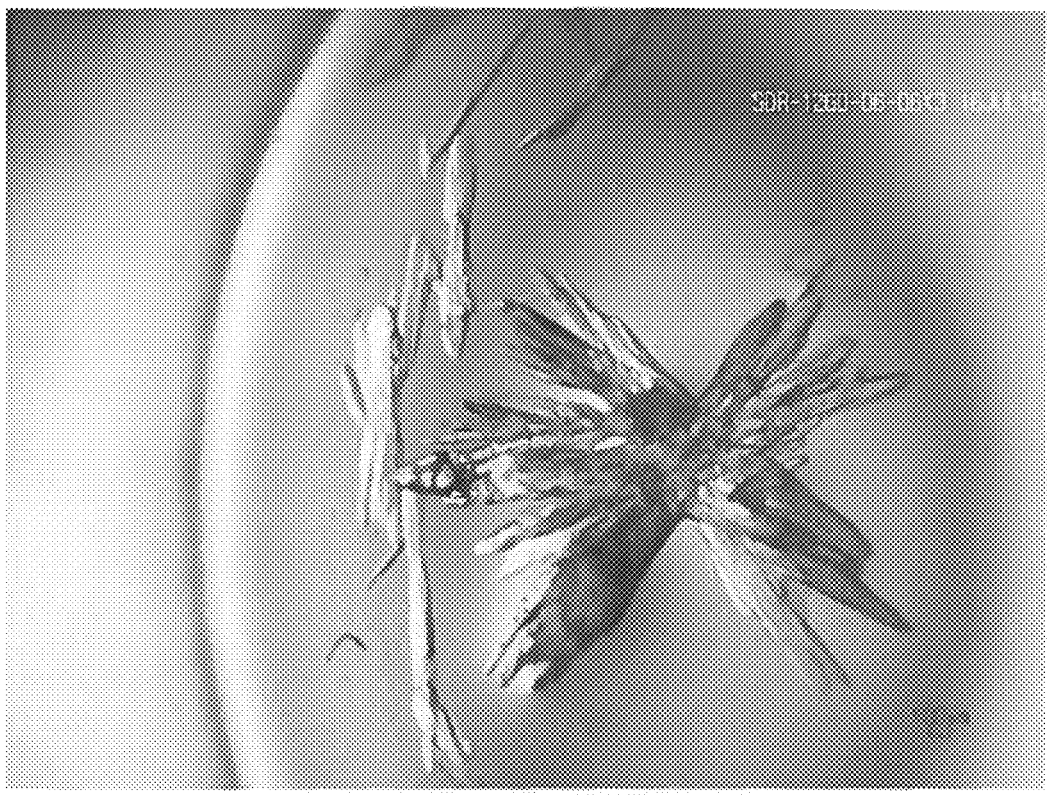
FIG. 2A-2B are an optical micrograph of the crystalline batch (FIG. 2A) and the crystal used for the data collection (FIG. 2B).
Figure 2B:
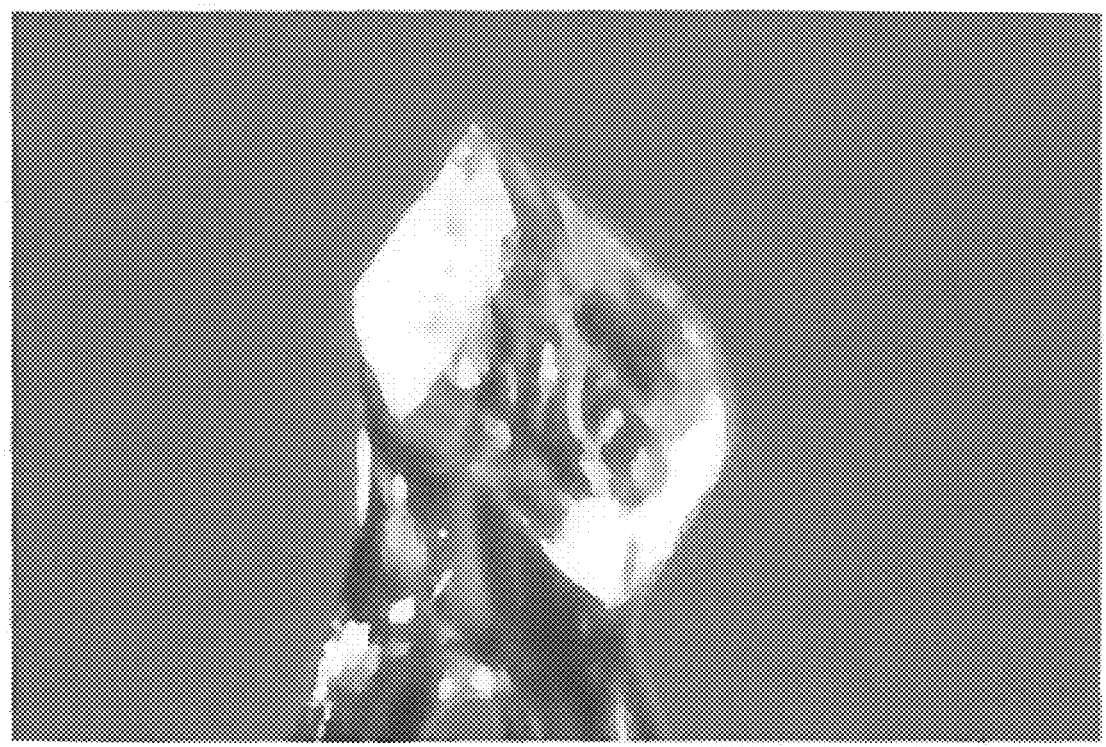

The following notation is applied: an embodiment of the invention is identified as Ei, where i is an integer indicating the number of the embodiment. An embodiment Ei' specifying a specific embodiment a previously listed embodiment Ei is identified as Ei'(Ei), e.g. E2(E1) means "in an embodiment E2 of embodiment E1".

Where an embodiment is a combination of two embodiments the notation is similarly Ei"(Ei and Ei'), e.g. E3(E2 and E1) means "in an embodiment E3 of any of embodiments E2 and E1"

Where an embodiment is a combination of more than two embodiments the notation is similarly Ei'"(Ei, Ei' and Ei"), e.g. E4(E1, E2 and E3) means "in an embodiment E4 of any of embodiments E1, E2 and E3"

In a first embodiment E1 the present invention relates to compounds having the following structure

P1

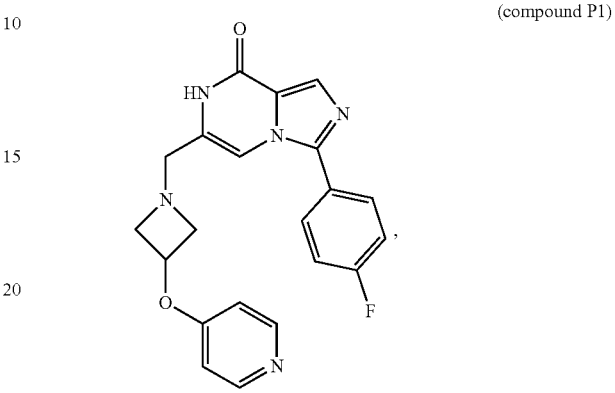

(compound P1)

P2

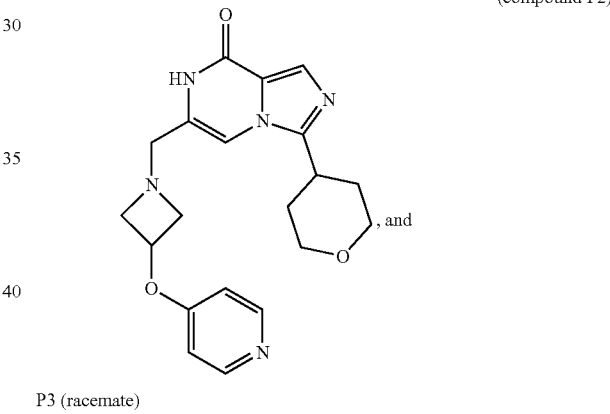

(compound P2)

P3 (racemate)

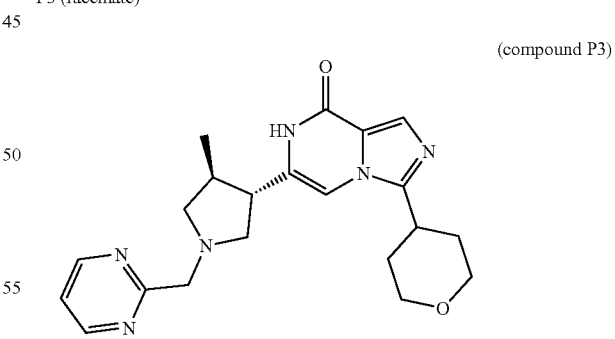

(compound P3)

in racemic form and in enantiomerically enriched or pure form.

In an embodiment E2(E1) the enantiomerically pure variant of compound P3 is the first eluding compound when the racemic mixture of P3 is separated by Chiral HPLC (Column: Chiralpak IA, 250×4.6 mm×5 um; mobile phase Hex/EtOH/DEA=70:30:0.2) with a flow rate of 1.0 m/min (P3 enantiomer 1).

E3(E1 and E2): A compound of any of E1 and E2 for the use as a medicament.

E4: A compound of any of E1 and E2 or the compound P4

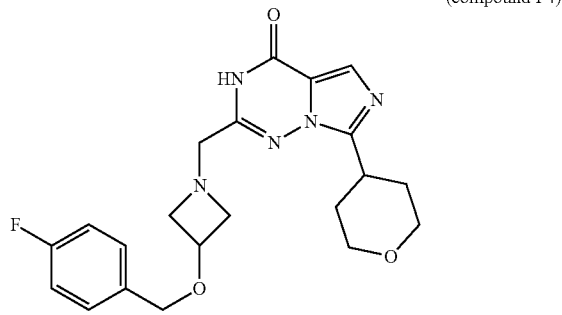

(compound P4)

for use in the treatment of benign prostate hyperplasia or sickle cell disease.

E5: A pharmaceutical composition comprising a therapeutically effective amount of any of the compounds of E1 and E2 or the compound P4, and one or more pharmaceutically acceptable carriers, diluents or excipients.

E6(E5): The pharmaceutical is for the treatment of benign prostate hyperplasia or sickle cell disease.

E7: Use of the compound P4 or any of the compounds of E1 and E2 for the manufacture of a medicament for the treatment of benign prostate hyperplasia or sickle cell disease.

E8: A method of treating a subject suffering from benign prostate hyperplasia or sickle cell disease comprising administering a therapeutically effective amount of a compound P4 or any of the compounds of E1 and E2 to a subject in need thereof E9: A compound selected from the group consisting of 3-(4-fluorophenyl)-6-((3-(pyridin-4-yloxy)azetidin-1-yl)methyl)imidazo[1,5-a]pyrazin-8(7H)-one (P1), 6-[3-(pyridin-3-yloxy)-azetidin-1-ylmethyl]-3-(tetrahydro-pyran-4-yl)-7H-imidazo[1,5-a]pyrazin-8-one (P2), (3S,4S)-6-(4-methyl-1-pyrimidin-2-ylmethyl-pyrrolidin-3-yl)-3-(tetrahydro-pyran-4-yl)-7H-imidazo[1,5-a]pyrazin-8-one (P3, enantiomer 1), and (3R,4R)-6-(4-methyl-1-pyrimidin-2-ylmethyl-pyrrolidin-3-yl)-3-(tetrahydro-pyran-4-yl)-7H-imidazo[1,5-a]pyrazin-8-one (P3, enantiomer 2).

E10(E9) The compound (3S,4S)-6-(4-methyl-1-pyrimidin-2-ylmethyl-pyrrolidin-3-yl)-3-(tetrahydro-pyran-4-yl)-7H-imidazo[1,5-a]pyrazin-8-one (P3, enantiomer 1).

E11(E9) The compound (3R,4R)-6-(4-methyl-1-pyrimidin-2-ylmethyl-pyrrolidin-3-yl)-3-(tetrahydro-pyran-4-yl)-7H-imidazo[1,5-a]pyrazin-8-one (P3, enantiomer 2).

E12 (E9, E10 and E11) A compound of any of E9 to E11 for the use as a medicament.

E13: A compound selected from the group consisting of 3-(4-fluorophenyl)-6-((3-(pyridin-4-yloxy)azetidin-1-yl)methyl)imidazo[1,5-a]pyrazin-8(7H)-one (P1), 6-[3-(pyridin-3-yloxy)-azetidin-1-ylmethyl]-3-(tetrahydro-pyran-4-yl)-7H-imidazo[1,5-a]pyrazin-8-one (P2), (3S,4S)-6-(4-methyl-1-pyrimidin-2-ylmethyl-pyrrolidin-3-yl)-3-(tetrahydro-pyran-4-yl)-7H-imidazo[1,5-a]pyrazin-8-one (P3, enantiomer 1), (3R,4R)-6-(4-methyl-1-pyrimidin-2-ylmethyl-pyrrolidin-3-yl)-3-(tetrahydro-pyran-4-yl)-7H-imidazo[1,5-a]pyrazin-8-one (P3, enantiomer 2) and 2-[3-(4-fluoro-phenoxy)-azetidin-1-ylmethyl]-7-(tetrahydro-pyran-4-yl)-3H-imidazo[5,1-f][1,2,4]triazin-4-one (P4) for use in the treatment of benign prostate hyperplasia or sickle cell disease.

E14: A pharmaceutical composition comprising a therapeutically effective amount of any of the compounds 3-(4-fluorophenyl)-6-((3-(pyridin-4-yloxy)azetidin-1-yl)methyl)imidazo[1,5-a]pyrazin-8(7H)-one (P1), 6-[3-(pyridin-3-yloxy)-azetidin-1-ylmethyl]-3-(tetrahydro-pyran-4-yl)-7H-imidazo[1,5-a]pyrazin-8-one (P2), (3S,4S)-6-(4-methyl-1-pyrimidin-2-ylmethyl-pyrrolidin-3-yl)-3-(tetrahydro-pyran-4-yl)-7H-imidazo[1,5-a]pyrazin-8-one (P3, enantiomer 1), (3R,4R)-6-(4-methyl-1-pyrimidin-2-ylmethyl-pyrrolidin-3-yl)-3-(tetrahydro-pyran-4-yl)-7H-imidazo[1,5-a]pyrazin-8-one (P3, enantiomer 2) and 2-[3-(4-fluoro-phenoxy)-azetidin-1-ylmethyl]-7-(tetrahydro-pyran-4-yl)-3H-imidazo[5,1-f][1,2,4]triazin-4-one (P4), and one or more pharmaceutically acceptable carriers, diluents or excipients E15(E14): The pharmaceutical is for the treatment of benign prostate hyperplasia or sickle cell disease.

E16: Use of any of the compounds 3-(4-fluorophenyl)-6-((3-(pyridin-4-yloxy)azetidin-1-yl)methyl)imidazo[1,5-a]pyrazin-8(7H)-one (P1), 6-[3-(pyridin-3-yloxy)-azetidin-1-ylmethyl]-3-(tetrahydro-pyran-4-yl)-7H-imidazo[1,5-a]pyrazin-8-one (P2), (3S,4S)-6-(4-methyl-1-pyrimidin-2-ylmethyl-pyrrolidin-3-yl)-3-(tetrahydro-pyran-4-yl)-7H-imidazo[1,5-a]pyrazin-8-one (P3, enantiomer 1), (3R,4R)-6-(4-methyl-1-pyrimidin-2-ylmethyl-pyrrolidin-3-yl)-3-(tetrahydro-pyran-4-yl)-7H-imidazo[1,5-a]pyrazin-8-one (P3, enantiomer 2) and 2-[3-(4-fluoro-phenoxy)-azetidin-1-ylmethyl]-7-(tetrahydro-pyran-4-yl)-3H-imidazo[5,1-f][1,2,4]triazin-4-one (P4) for the manufacture of a medicament for the treatment of benign prostate hyperplasia or sickle cell disease.

E17: A method of treating a subject suffering from benign prostate hyperplasia or sickle cell disease comprising administering a therapeutically effective amount of any of the compounds 3-(4-fluorophenyl)-6-((3-(pyridin-4-yloxy)azetidin-1-yl)methyl)imidazo[1,5-a]pyrazin-8(7H)-one (P1), 6-[3-(Pyridin-3-yloxy)-azetidin-1-ylmethyl]-3-(tetrahydro-pyran-4-yl)-7H-imidazo[1,5-a]pyrazin-8-one (P2), (3S,4S)-6-(4-methyl-1-pyrimidin-2-ylmethyl-pyrrolidin-3-yl)-3-(tetrahydro-pyran-4-yl)-7H-imidazo[1,5-a]pyrazin-8-one (P3, enantiomer 1), (3R,4R)-6-(4-methyl-1-pyrimidin-2-ylmethyl-pyrrolidin-3-yl)-3-(tetrahydro-pyran-4-yl)-7H-imidazo[1,5-a]pyrazin-8-one (P3, enantiomer 2) and 2-[3-(4-fluoro-phenoxy)-azetidin-1-ylmethyl]-7-(tetrahydro-pyran-4-yl)-3H-imidazo[5,1-f][1,2,4]triazin-4-one (P4) to a subject in need thereof.

PDE9 Inhibitors

In the context of the present invention a compound is considered to be a PDE9 inhibitor if the amount required to reach the $IC_{50}$ level of any of the three PDE9 isoforms is 10 micro molar or less, preferably less than 9 micro molar, such as 8 micro molar or less, such as 7 micro molar or less, such as 6 micro molar or less, such as 5 micro molar or less, such as 4 micro molar or less, such as 3 micro molar or less, more preferably 2 micro molar or less, such as 1 micro molar or less, in particular 500 nM or less. In preferred embodiments the required amount of PDE9 inhibitor required to reach the $IC_{50}$ level of PDE9 is 400 nM or less, such as 300 nM or less, 200 nM or less, 100 nM or less, or even 80 nM or less, such as 50 nM or less, for example 25 nM or less.

Throughout this application the notations $IC_{50}$ and IC50 are used interchangeably.

Isomeric Forms

Where compounds of the present invention contain one or more chiral centers reference to any of the compounds will, unless otherwise specified, cover the enantiomerically or diastereomerically pure compound as well as mixtures of the enantiomers or diastereomers in any ratio.

Pharmaceutically Acceptable Salts

The present invention also comprises salts of the compounds, typically, pharmaceutically acceptable salts. Such salts include pharmaceutically acceptable acid addition salts. Acid addition salts include salts of inorganic acids as well as organic acids.

Representative examples of suitable inorganic acids include hydrochloric, hydrobromic, hydroiodic, phosphoric, sulfuric, sulfamic, nitric acids and the like. Representative examples of suitable organic acids include formic, acetic, trichloroacetic, trifluoroacetic, propionic, benzoic, cinnamic, citric, fumaric, glycolic, itaconic, lactic, methanesulfonic, maleic, malic, malonic, mandelic, oxalic, picric, pyruvic, salicylic, succinic, methane sulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, theophylline acetic acids, as well as the 8-halotheophyllines, for example 8-bromotheophylline and the like. Further examples of pharmaceutically acceptable inorganic or organic acid addition salts include the pharmaceutically acceptable salts listed in Berge, S. M. et al., J. Pharm. Sci. 1977, 66, 2, the contents of which are hereby incorporated by reference.

Furthermore, the compounds of this invention may exist in unsolvated as well as in solvated forms with pharmaceutically acceptable solvents such as water, ethanol and the like. In general, the solvated forms are considered equivalent to the unsolvated forms for the purposes of this invention.

Pharmaceutical Composition

The present invention further provides a pharmaceutical composition comprising a therapeutically effective amount of any of the compounds of the present invention and a pharmaceutically acceptable carrier or diluent. The present invention also provides a pharmaceutical composition comprising a therapeutically effective amount of one of the specific compounds disclosed in the Experimental Section herein and a pharmaceutically acceptable carrier or diluent.

The compounds of the invention may be administered alone or in combination with pharmaceutically acceptable carriers, diluents or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 22nd Edition, Gennaro, Ed., Mack Publishing Co., Easton, Pa., 2013.

The pharmaceutical compositions may be specifically formulated for administration by any suitable route such as oral, rectal, nasal, pulmonary, topical (including buccal and sublingual), transdermal, intracisternal, intraperitoneal, vaginal and parenteral (including subcutaneous, intramuscular, intrathecal, intravenous and intradermal) routes. It will be appreciated that the route will depend on the general condition and age of the subject to be treated, the nature of the condition to be treated and the active ingredient.

Pharmaceutical compositions for oral administration include solid dosage forms such as capsules, tablets, dragees, pills, lozenges, powders and granules. Where appropriate, the compositions may be prepared with coatings such as enteric coatings or they may be formulated so as to provide controlled release of the active ingredient such as sustained or prolonged release according to methods well known in the art. Liquid dosage forms for oral administration include solutions, emulsions, suspensions, syrups and elixirs.

Pharmaceutical compositions for parenteral administration include sterile aqueous and nonaqueous injectable solutions, dispersions, suspensions or emulsions as well as sterile powders to be reconstituted in sterile injectable solutions or dispersions prior to use. Other suitable administration forms include, but are not limited to, suppositories, sprays, ointments, creams, gels, inhalants, dermal patches and implants.

Typical oral dosages range from about 0.001 to about 100 mg/kg body weight per day. Typical oral dosages also range from about 0.01 to about 50 mg/kg body weight per day. Typical oral dosages further range from about 0.05 to about 10 mg/kg body weight per day. Oral dosages are usually administered in one or more dosages, typically, one to three dosages per day. The exact dosage will depend upon the frequency and mode of administration, the gender, age, weight and general condition of the subject treated, the nature and severity of the condition treated and any concomitant diseases to be treated and other factors evident to those skilled in the art.

The formulations may also be presented in a unit dosage form by methods known to those skilled in the art. For illustrative purposes, a typical unit dosage form for oral administration may contain from about 0.01 to about 1000 mg, from about 0.05 to about 500 mg, or from about 0.5 mg to about 200 mg.

For parenteral routes such as intravenous, intrathecal, intramuscular and similar administration, typical doses are in the order of half the dose employed for oral administration.

The present invention also provides a process for making a pharmaceutical composition comprising admixing a therapeutically effective amount of a compound of the present invention and at least one pharmaceutically acceptable carrier or diluent. In an embodiment, of the present invention, the compound utilized in the aforementioned process is one of the specific compounds disclosed in the Experimental Section herein.

The compounds of this invention are generally utilized as the free substance or as a pharmaceutically acceptable salt thereof. Such salts are prepared in a conventional manner by treating a solution or suspension of a compound of the present invention with a molar equivalent of a pharmaceutically acceptable acid. Representative examples of suitable organic and inorganic acids are described above.

For parenteral administration, solutions of the compounds of the present invention in sterile aqueous solution, aqueous propylene glycol, aqueous vitamin E or sesame or peanut oil may be employed. Such aqueous solutions should be suitably buffered if necessary and the liquid diluent first rendered isotonic with sufficient saline or glucose. The aqueous solutions are particularly suitable for intravenous, intramuscular, subcutaneous and intraperitoneal administration. The compounds of the present invention may be readily incorporated into known sterile aqueous media using standard techniques known to those skilled in the art.

Suitable pharmaceutical carriers include inert solid diluents or fillers, sterile aqueous solutions and various organic solvents. Examples of solid carriers include lactose, terra alba, sucrose, cyclodextrin, talc, gelatin, agar, pectin, acacia, magnesium stearate, stearic acid and lower alkyl ethers of cellulose. Examples of liquid carriers include, but are not limited to, syrup, peanut oil, olive oil, phospholipids, fatty acids, fatty acid amines, polyoxyethylene and water. Similarly, the carrier or diluent may include any sustained release material known in the art, such as glyceryl monostearate or glyceryl distearate, alone or mixed with a wax. The pharmaceutical compositions formed by combining the compounds of the present invention and a pharmaceutically acceptable carrier are then readily administered in a variety of dosage forms suitable for the disclosed routes of administration. The formulations may conveniently be presented in unit dosage form by methods known in the art of pharmacy.

Formulations of the present invention suitable for oral administration may be presented as discrete units such as capsules or tablets, each containing a predetermined amount of the active ingredient, and optionally a suitable excipient. Furthermore, the orally available formulations may be in the form of a powder or granules, a solution or suspension in an aqueous or non-aqueous liquid, or an oil-in-water or water-in-oil liquid emulsion.

If a solid carrier is used for oral administration, the preparation may be tabletted, placed in a hard gelatine capsule in powder or pellet form or it may be in the form of a troche or lozenge. The amount of solid carrier will vary widely but will range from about 25 mg to about 1 g per dosage unit. If a liquid carrier is used, the preparation may be in the form of a syrup, emulsion, soft gelatine capsule or sterile injectable liquid such as an aqueous or non-aqueous liquid suspension or solution.

The pharmaceutical compositions of the invention may be prepared by conventional methods in the art. For example, tablets may be prepared by mixing the active ingredient with ordinary adjuvants and/or diluents and subsequently compressing the mixture in a conventional tabletting machine prepare tablets. Examples of adjuvants or diluents comprise: corn starch, potato starch, talcum, magnesium stearate, gelatin, lactose, gums, and the like. Any other adjuvants or additives usually used for such purposes such as colorings, flavorings, preservatives etc. may be used provided that they are compatible with the active ingredients.

Compounds of the Invention

Table 1 lists compounds of the invention and the corresponding IC50 values (nM) determined as described in the section "PDE9 inhibition assay". Further, the concentration of compounds in plasma and brain, determined as described in the section "Blood Brain Barrier penetration", are listed. Each of the compounds constitutes an individual embodiment of the present invention:

TABLE 1

Compounds of the invention, IC50 values and plasma/brain concentration

| Compound | PDE9 IC50 (nM) | PDE1 IC50 (nM) | Plasma concentration after 30 minutes and 120 minutes (ng/mL) | Brain concentration after 30 minutes and 120 minutes (ng/mL) | Brain/Plasma ratio after 30 minutes and 120 minutes |
|---|---|---|---|---|---|
| Compound (P1) | 42 | 45090 | 30 min.: 719<br>120 min.: 86 | 30 min.: 42<br>120 min.: 7 | 0.06<br>0.08 |
| Compound (P2) | 36 | 5283 | 30 min.: 715<br>120 min.: 11 | Below detection limit | Not calculated (brain concentration below limit of detection) |
| Compound (P3, enantiomer 1) | 49 | 3000 | 30 min.: 1620<br>120 min.: 226 | 30 min.: 67<br>120 mm.: 7 | 0.04<br>0.03 |
| Compound (P4) | 10 | 1009 | 30 min.: 3380<br>120 min. 352 | 30 min.: 125<br>120 min.: 15 | 0.04<br>0.04 |
| 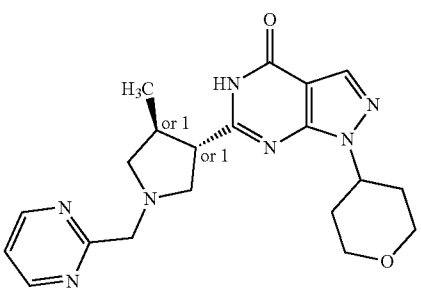 [SMILES: C[C@@H]1CN(Cc2ncccn2)C[C@H]1c1nc2c(cnn2C2CCOCC2)c(=O)[nH]1]<br>Reference compound disclosed in WO2008/139293 | 70 | 2500 | 30 min.: 1230<br>120 min.: 529 | 30 min.: 500<br>120 min.: 215 | 0.41<br>0.41 |

EXAMPLES

Example 1. Synthesis of the Compounds

The compounds of the present invention may be synthesized as described below.

Overview Schemes:

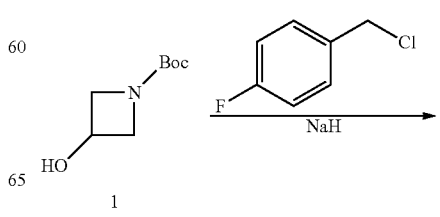

1

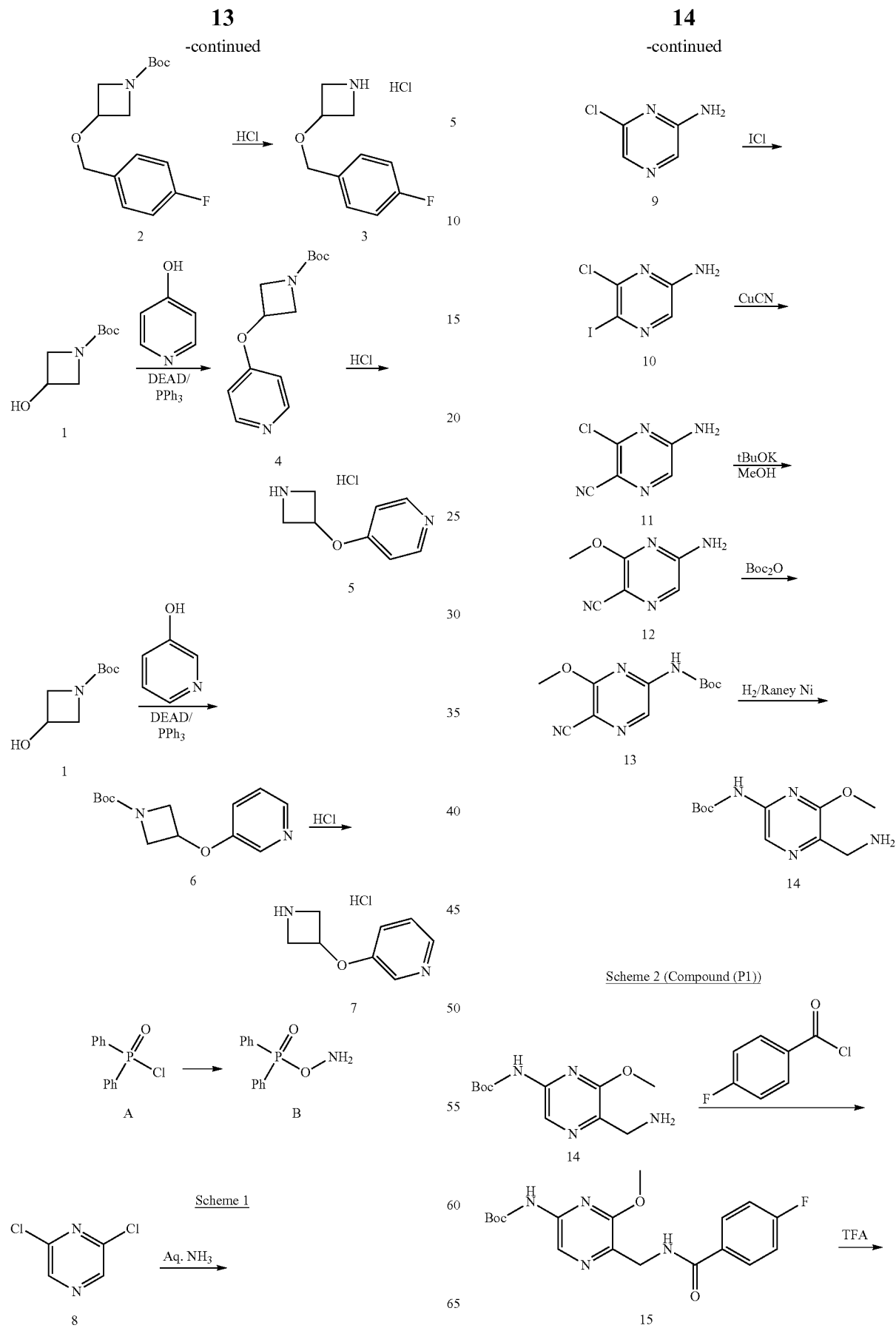

-continued
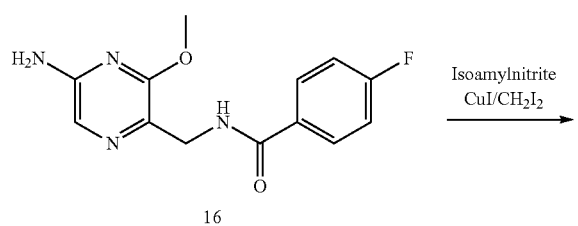
16
Isoamylnitrite
CuI/CH₂I₂
→
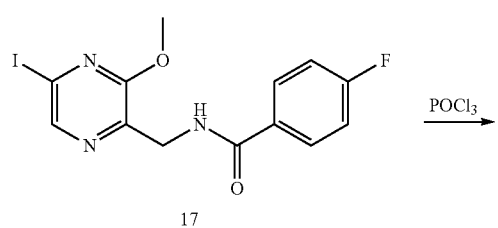
17
POCl₃
→
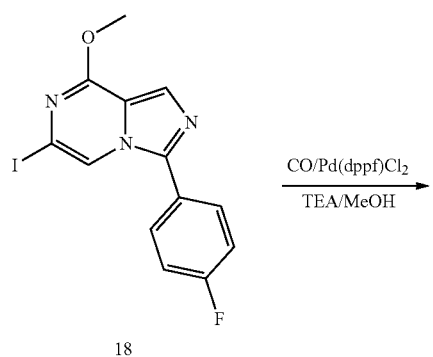
18
CO/Pd(dppf)Cl₂
TEA/MeOH
→
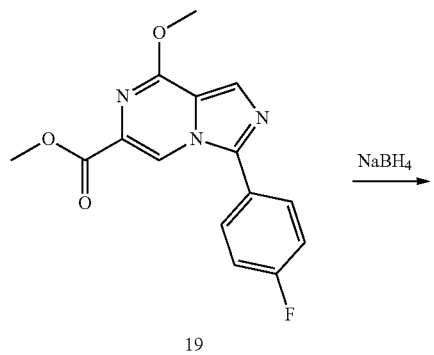
19
NaBH₄
→
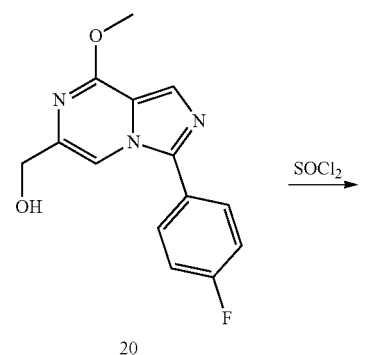
20
SOCl₂
→
-continued
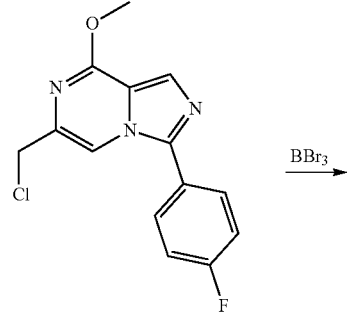
21
BBr₃
→
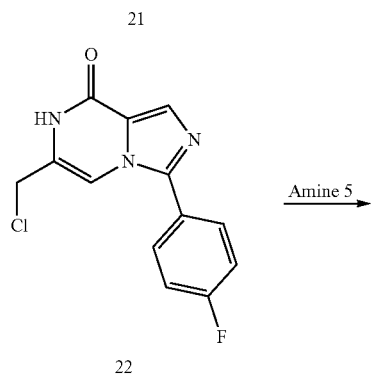
22
Amine 5
→
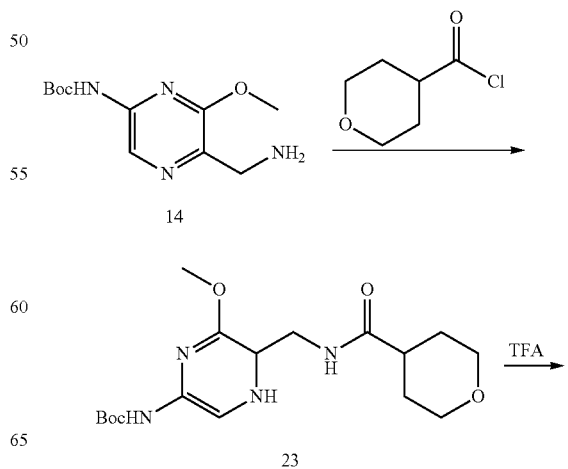
P1
Scheme 3 (Compound (P2))

-continued
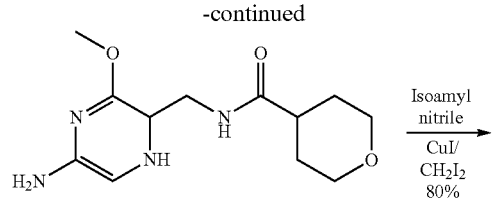
24
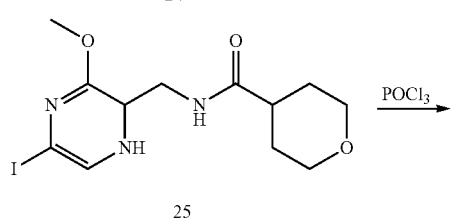
25
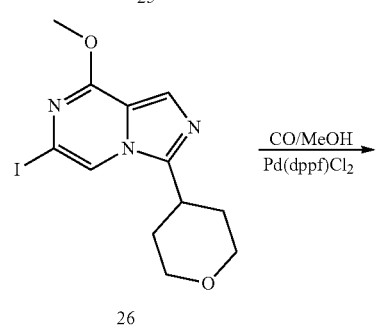
26
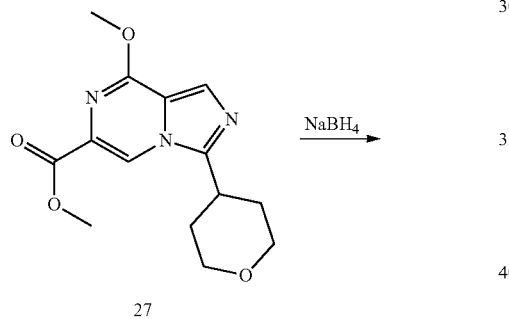
27
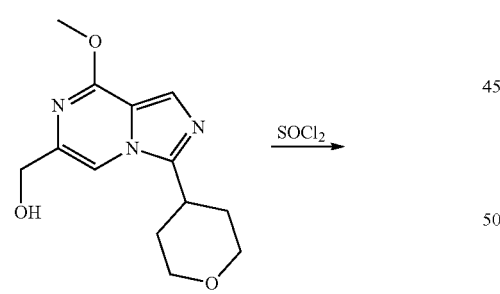
28
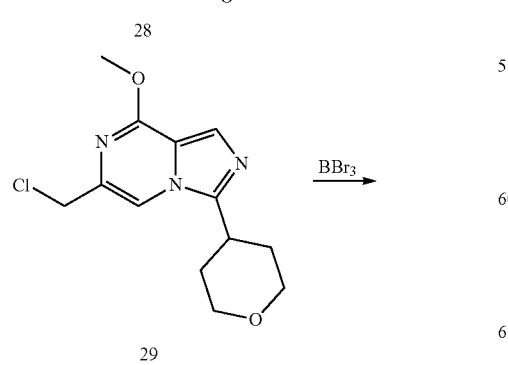
29
-continued
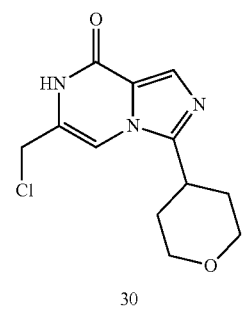
30
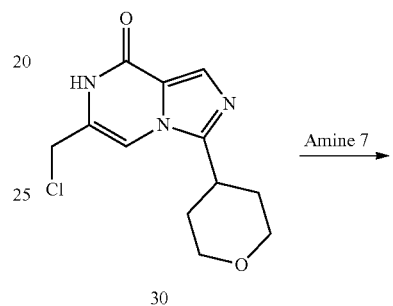
30
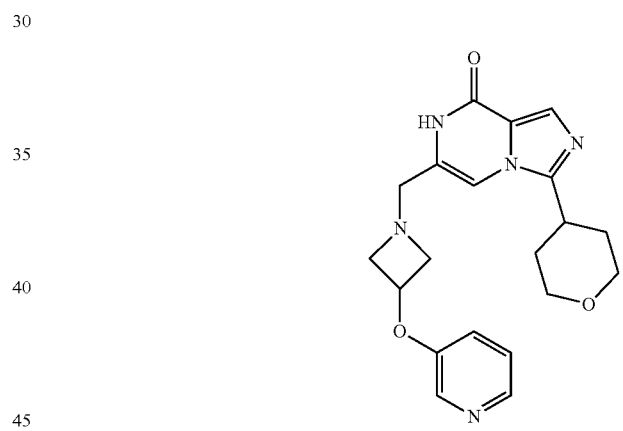
P2
Scheme 4 (Compound (P3))
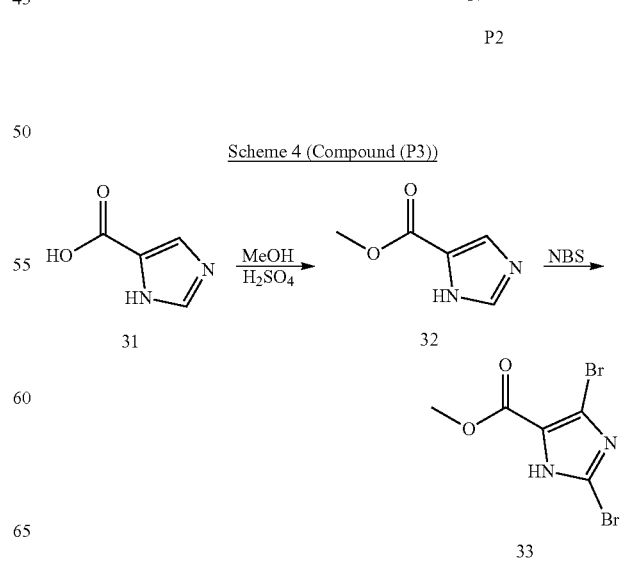

-continued
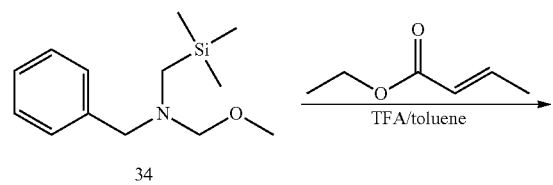
34
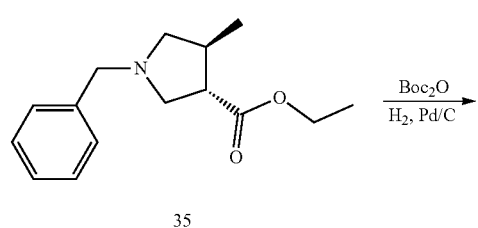
35
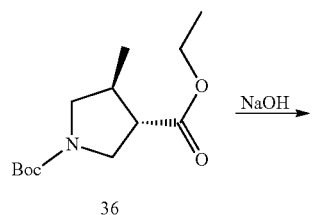
36
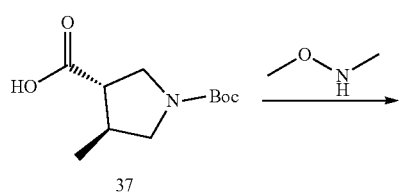
37
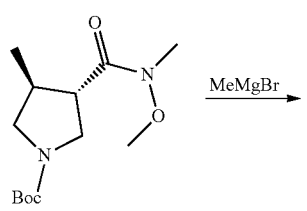
38
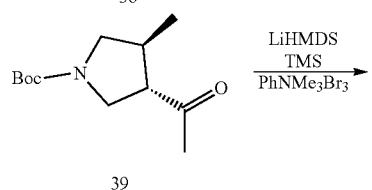
39
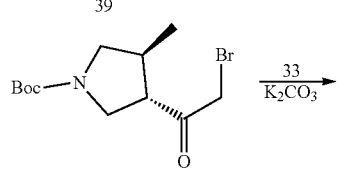
40
-continued
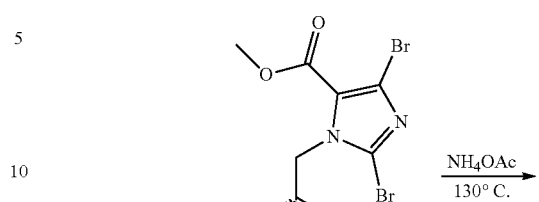
41
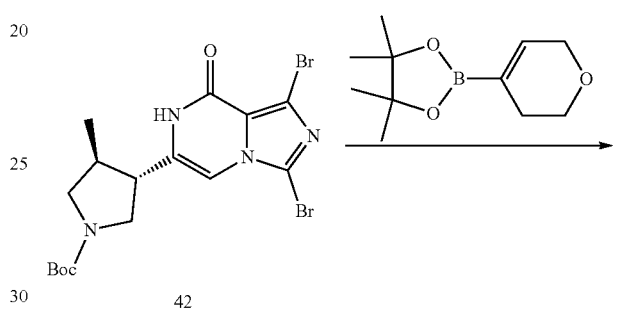
42
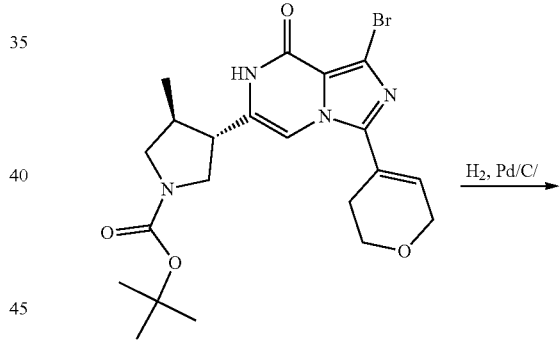
43
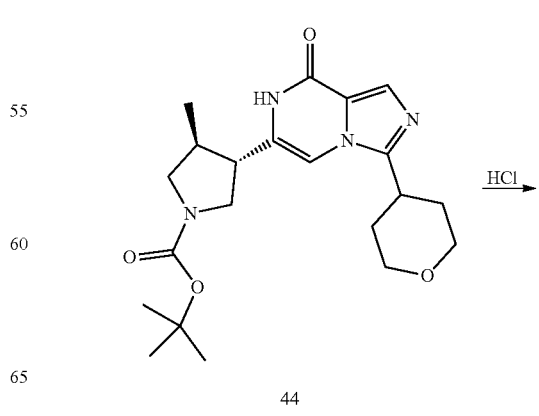
44

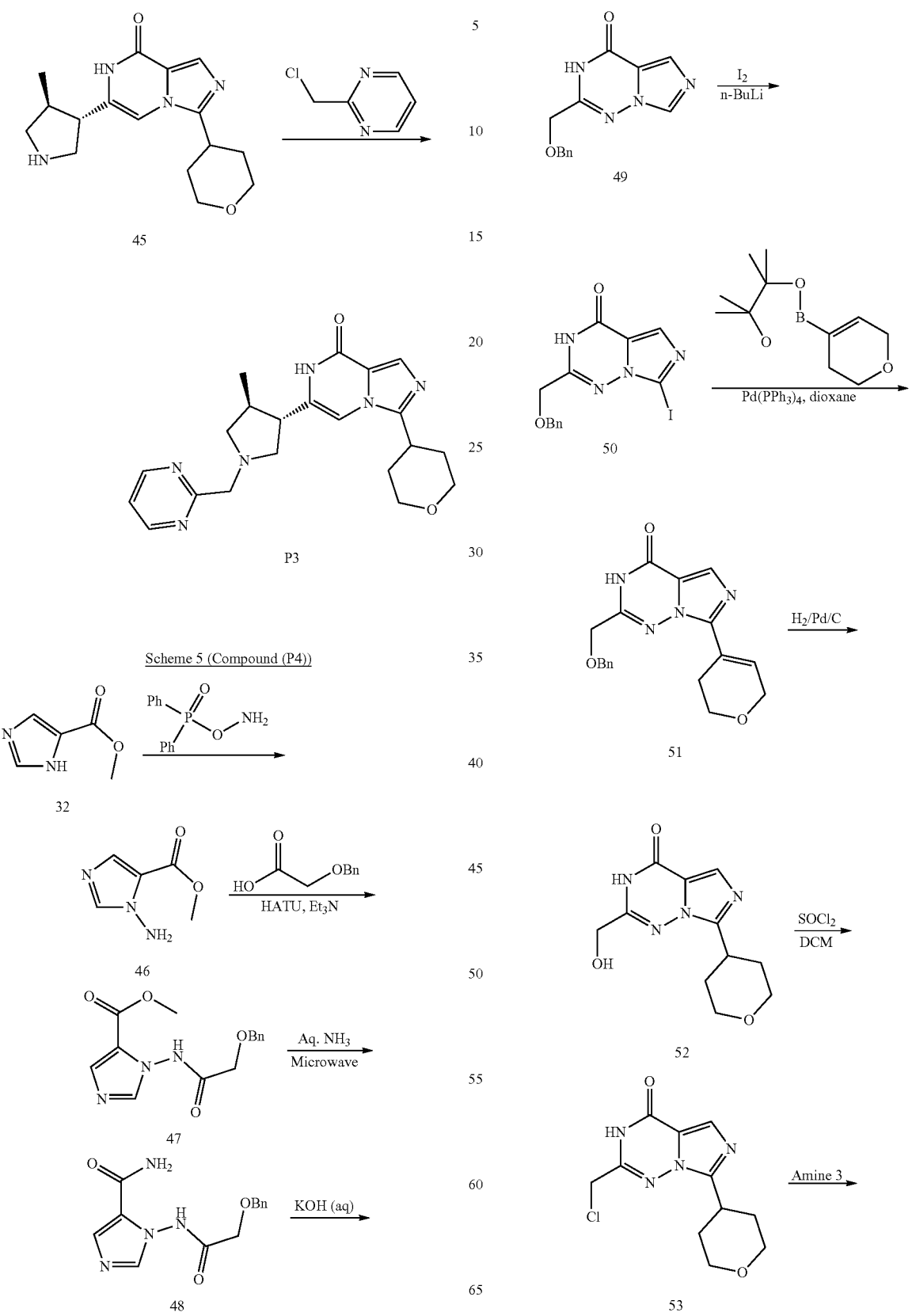

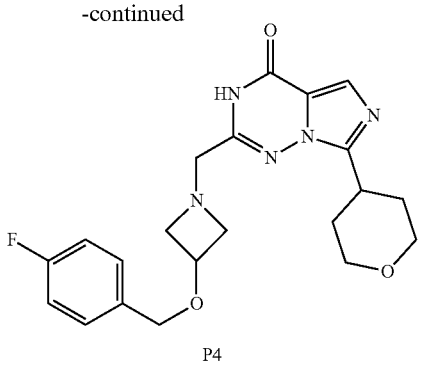

P4

Synthetic Procedures:
List of Abbreviations
aq aqueous
NBS N-bromosuccinimide
Boc tert-Butoxycarbonyl
° C. degrees Celsius
CDI N,N-carbonyl dimidazole
$\delta_H$ chemical shift in parts per million downfield from tetramethylsilane
DCM dichloromethane
DEAD diethyl azodicarboxylate
Dppf bis(diphenylphosphino)ferrocene
DIPEA N,N-diisopropylethylamine
DMF N,N-dimethylformamide
eq equivalent
ESI electrospray ionization
Et ethyl
EtOAc ethyl acetate
g gram(s)
HPLC high-performance liquid chromatography
h hours
Hz hertz
J coupling constant (in NMR spectrometry)
LCMS liquid chromatography mass spectrometry
LiHMDS Lithium bis(trimethylsilyl)amide
μ micro
m multiplet (spectral); meter(s); milli
$M^+$ parent molecular ion
Me methyl
MeCN acetonitrile
MeOH methanol
MHz megahertz
min minute(s)
mL milliliter
MS mass spectrometry
MTBE Methyl-tert-butyl ether
N normal (equivalents per liter)
NaOH sodium hydroxide
NBS N-Bromosuccinimide
nm nanometer(s)
NMR nuclear magnetic resonance
PE petroleum ether bp: 60~90° C.
rt room temperature
s singlet (spectral)
t triplet (spectral)
T temperature
TEA triethylamine
TFA trifluoroacetic acid
THF tetrahydrofuran
TLC thin layer chromatography
TMS tetramethylsilane
TMS-Cl trimethylsilyl chloride
Tol toluene General Experimental Methods $^1$H NMR spectra were recorded on Bruker Avance III 400 MHz and Bruker Fourier 300 MHz and TMS was used as an internal standard.

LCMS was taken on a quadrupole Mass Spectrometer on Agilent LC/MSD 1200 Series (Column: ODS 2000 (50×4.6 mm, 5 μm) operating in ES (+) or (−) ionization mode; T=30° C.; flow rate=1.5 mL/min; detected wavelength: 214 nm.

Synthesis of 6-Chloro-pyrazin-2-ylamine (9)

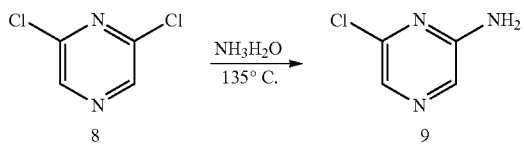

A solution of compound 8 (450.0 g, 3.02 mol) in conc. aq. $NH_3$ (3.0 L) was stirred at 135° C. overnight in a 10 L sealed pressure vessel. TLC and LC/MS showed complete conversion of the starting material. The reaction mixture was cooled to room temperature and filtered to afford a white solid. The solid was washed with water (200 mL×3), and then dried to afford compound 9 (312 g, 80% yield) as a solid.

$^1$HNMR (400 MHz, DMSO-d6): δ 7.82 (s, 1H), 7.12 (s, 1H), 6.93 (s, 2H). MS Calcd.: 129 MS Found: 130 ([M+H]$^+$).

Synthesis of 6-Chloro-5-iodo-pyrazin-2-ylamine (10)

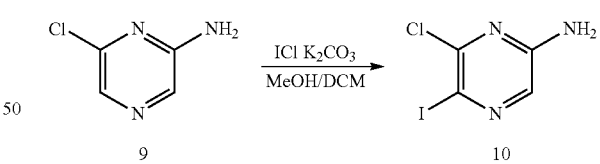

To a mixture of compound 9 (312.0 g, 2.4 mol) and $K_2CO_3$ (664.0 g, 4.8 mol) in MeOH (1.0 L) was dropwise added ICl (704.0 g, 4.3 mol in 1.0 L of DCM) over 2 hours at 0° C. Then the reaction mixture was stirred at room temperature overnight. The reaction was quenched with $Na_2SO_3$ aqueous solution (2M, 1.5 L). The mixture was extracted with DCM (1.0 L×3). The combined organic phases were dried over anhydrous $Na_2SO_4$, filtered and concentrated. The crude product was purified by column chromatography on silica gel (PE/EA=10/1 to 4/1) to afford compound 10 (460 g, 75% yield) as a solid.

$^1$HNMR (400 MHz, DMSO-d6): δ 7.68 (s, 1H), 7.07 (s, 2H). MS Calcd.: 255 MS Found: 256 ([M+H]$^+$).

Synthesis of 5-Amino-3-chloro-pyrazine-2-carbonitrile (11)

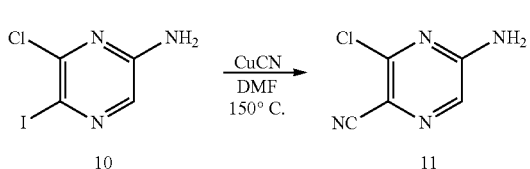

A mixture of compound 10 (460.0 g, 1.8 mol) and CuCN (177.0 g, 1.98 mol) in DMF (2.0 L) was stirred on an oil bath at 150° C. for 2 hours. LC/MS showed full conversion of the starting martial. The reaction mixture was cooled to room temperature and poured into EtOAc (1.5 L). To the resulting mixture was slowly added conc. aq. $NH_3$ (1.0 L), and it was then extracted with EtOAc (1.0 L×2). The combined organic phases were washed with $H_2O$ (1.5 L×5) and brine (1.5 L) and dried over anhydrous $Na_2SO_4$. The organic phase was filtered and concentrated to afford compound 11 (232 g, 84% yield) as solid.

$^1$HNMR (400 MHz, DMSO-d6): δ 8.12 (s, 2H), 7.88 (s, 1H). MS Calcd.: 154; MS Found: 155 ([M+H]$^+$).

Synthesis of 5-Amino-3-methoxy-pyrazine-2-carbonitrile (12)

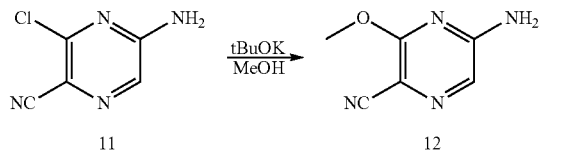

Potassium tert-butoxide (168.0 g, 1.5 mol) was added in portions into methanol (1.5 L) in a round-bottom flask. The suspension was refluxed for one hour. Then compound 11 (232.0 g, 1.5 mol) was added under an $N_2$ atmosphere. The resulting suspension was refluxed for 1.5 hours. After cooling to room temperature the reaction mixture was concentrated in vacuum and diluted with water (2.0 L), then extracted with EtOAc (2.0 L×5). The combined organic phases were dried with $Na_2SO_4$, filtered and concentrated to afford 12 (170 g, 75% yield) as a solid.

$^1$HNMR (300 MHz, DMSO-d6): δ 7.69 (s, 2H), 7.51 (s, 1H), 3.89 (s, 3H). MS Calcd.: 150; MS Found: 151 ([M+H]$^+$).

Synthesis of (5-Cyano-6-methoxy-pyrazin-2-yl)-carbamic acid tert-butyl ester (13)

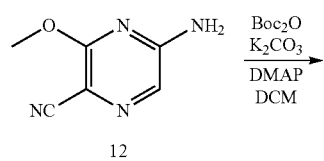

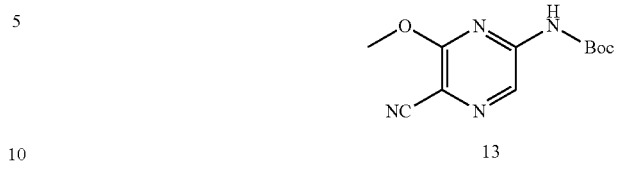

4-Dimethylaminopyridine (1.0 g, 0.01 mol) was added into a mixture of compound 12 (120.0 g, 0.8 mol) in DCM (1.5 L) at room temperature. Then di-tert-butyl dicarbonate (327 g, 1.5 mol) in DCM (1.0 L) was added dropwise at 10-20° C. for 2 hours. Then the reaction was stirred at room temperature overnight. The suspension dissolved and the reaction solution was diluted with 2 L of water. The DCM phase was separated and dried with sodium sulfate, filtered and concentrated in vacuum. The residue was purified by column chromatography on silica gel (PE/EtOAc=10:1) to afford 13 (150 g, 75% yield).

$^1$HNMR (300 MHz, DMSO-d6): δ 10.78 (s, 1H), 8.70 (s, 1H), 3.97 (s, 3H), 1.49 (s, 9H). MS Calcd.: 250; MS Found: 251 ([M+H]$^+$).

Synthesis of (5-Aminomethyl-6-methoxy-pyrazin-2-yl)-carbamic acid tert-butyl ester (14)

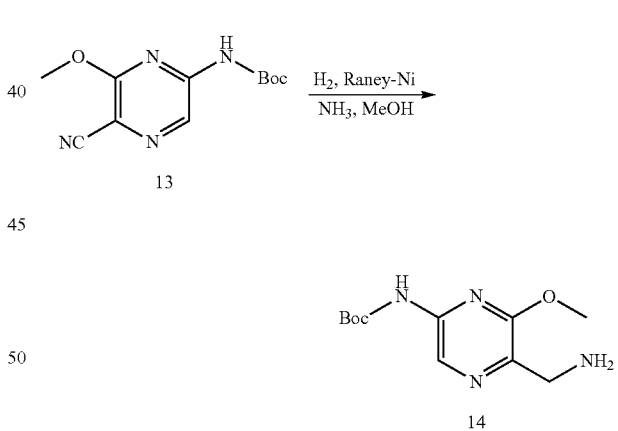

Raney Ni (10.0 g) was added into a mixture of compound 13 (30.0 g, 120 mmol) in concentrated $NH_3$ in MeOH (500 mL) at room temperature. The suspension was stirred at room temperature under 1 atm $H_2$ overnight. The reaction mixture was diluted with a mixture of DCM/MeOH (1:1). The reaction mixture was filtered and the filtrate was concentrated in vacuum. The residue was triturated with PE/EtOAc=2/1 to afford 14 (23 g, 75% yield) as a solid.

$^1$HNMR (300 MHz, DMSO-d6): δ 8.46 (s, 1H), 3.87 (s, 3H), 3.70 (s, 2H), 3.17 (s, 3H), 1.47 (s, 9H). MS Calcd.: 254; MS Found: 255 ([M+H]$^+$).

Synthesis of 5-[(4-Fluoro-benzoylamino)-methyl]-6-methoxy-pyrazin-2-yl-carbamic acid tert-butyl ester (15)

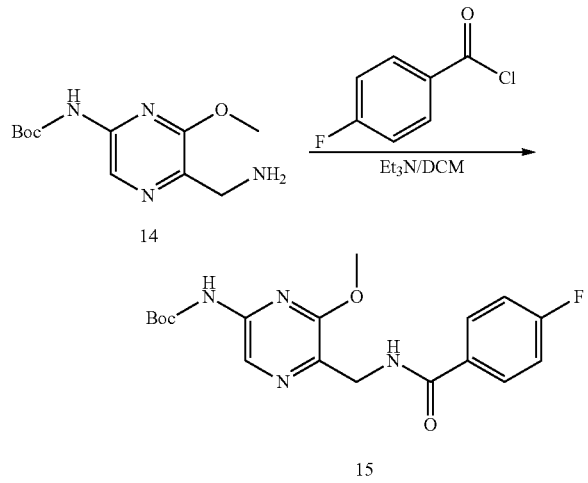

To a solution of compound 14 (4.52 g, 17.86 mmol) in DCM (200 mL) was added TEA (5.41 g, 58.53 mmol), then 4-fluorobenzoyl chloride (3.4 g, 21.42 mmol) was added dropwise. The resulting reaction mixture was stirred at room temperature for 2 hours. TLC detected the reaction was complete. The reaction was quenched with water (100 mL). The organic phase was separated and the aqueous phase was extracted with DCM (200 mL×2). The combined organic phases were dried over anhydrous MgSO$_4$, filtered and concentrated in vacuum. The residue was purified by column chromatography on silica gel to afford 15 (5.77 g, 85.9% yield) as a solid.

$^1$HNMR (400 MHz, DMSO-d6): δ 9.89 (s, 1H), 8.81 (t, J=5.6 Hz, 1H), 8.46 (s, 1H), 7.94 (m, 2H), 7.29 (m, 2H), 4.49 (d, J=5.6 Hz, 2H), 3.90 (s, 3H), 1.47 (s, 9H). MS Calcd.: 376; MS Found: 377 ([M+H]$^+$).

Synthesis of N-(5-Amino-3-methoxy-pyrazin-2-ylmethyl)-4-fluoro-benzamide (16)

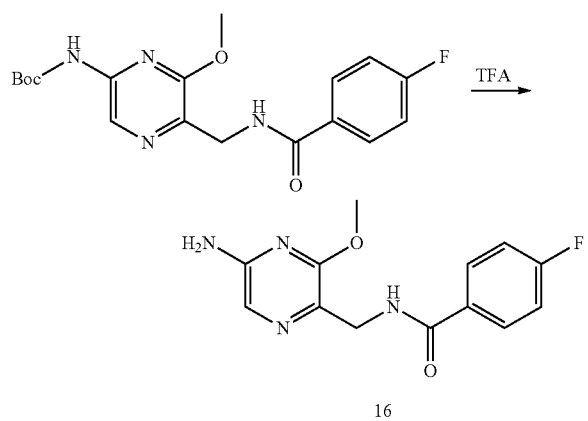

Compound 15 (5.77 g, 15.33 mmol) was dissolved in DCM (25 mL). TFA (25 mL) was added. The reaction was stirred at room temperature overnight. TLC detected the reaction was complete. The solvent was removed. The residue was diluted with DCM (100 mL) and saturated NaHCO$_3$ aqueous solution (100 mL). The organic phase was separated and the aqueous phase was extracted with DCM (100 mL×2). The combined organic phases were dried over anhydrous MgSO$_4$, filtered and concentrated in vacuum. The residue was purified by column chromatography on silica gel (eluted with PE/EtOAc=6:1 to 1:1) to afford 16 (3.9 g, 92.2% yield) as a solid.

$^1$HNMR (300 MHz, CDCl$_3$): δ 7.90-7.85 (m, 2H), 7.46 (s, 1H), 7.40 (t, J=6.0 Hz, 1H), 7.11 (m, 2H), 4.60 (d, J=6.0 Hz, 2H), 4.37 (s, 2H), 3.93 (s, 3H). MS Calcd.: 276; MS Found: 277 ([M+H]$^+$).

Synthesis of 4-Fluoro-N-(5-iodo-3-methoxy-pyrazin-2-ylmethyl)-benzamide (17)

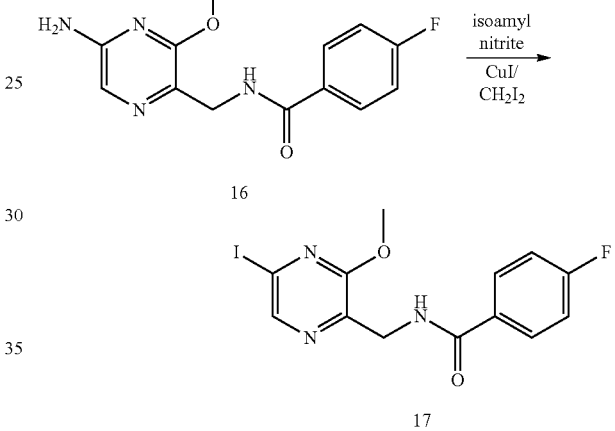

Compound 16 (3.9 g, 14.1 mmol) was dissolved in anhydrous THF (100 mL). CuI (2.7 g, 14.1 mmol), then isoamyl nitrite (4.9 g, 42.3 mmol) and CH$_2$I$_2$ (3.8 g, 14.1 mmol) were added under N$_2$ gas atmosphere. The reaction mixture was heated at 75° C. for 3 hours. Then the reaction was cooled to room temperature and filtered. The filtrate was concentrated in vacuum. The residue was purified by column chromatography on silica gel (eluted with PE/EtOAc 5:1) to afford 17 (2.0 g, 37% yield) as a solid.

$^1$HNMR (400 MHz, CDCl$_3$): δ 8.34 (s, 1H), 7.88 (m, 2H), 7.36 (t, J=4.4 Hz, 1H), 7.14 (m, 2H), 4.66 (d, J=4.4 Hz, 2H), 4.04 (s, 3H). MS Calcd.: 387; MS Found: 388 ([M+H]$^+$).

Synthesis of 3-(4-Fluoro-phenyl)-6-iodo-8-methoxy-imidazo[1,5-a]pyrazine (18)

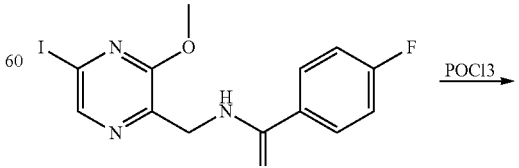

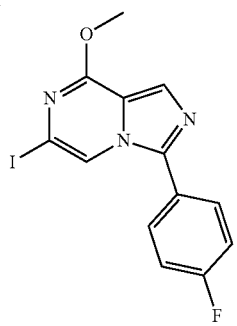

18

Compound 17 (1.6 g, 4.13 mmol) was suspended in MeCNCH₃CN (50 mL). POCl₃ (6.3 g, 41.3 mmol) and TEA (1.25 g, 12.39 mmol) was added under $N_2$ gas atmosphere and the reaction mixture was heated at 85° C. for 6 hours. The solvent was removed under reduced pressure. The residue was diluted with DCM (100 mL) and ice-water (30 mL). Then saturated $Na_2CO_3$ aqueous solution (100 mL) was added. The organic phase was separated and the aqueous phase was extracted with DCM (100 mL×2). The combined organic phases were dried, filtered and concentrated in vacuum. The residue was purified by column chromatography on silica gel (eluted with PE/EtOAc=20:1 to 3:1) to afford 18 (1.5 g, 97.8% yield) as a solid.

¹HNMR (300 MHz, CDCl₃): δ 8.01 (s, 1H), 7.82 (s, 1H), 7.77-7.72 (m, 2H), 7.28-7.23 (m, 2H), 4.11 (s, 3H). MS Calcd.: 369; MS Found: 370 ([M+H]⁺).

Synthesis of 3-(4-Fluoro-phenyl)-8-methoxy-imidazo[1,5-a]pyrazine-6-carboxylic acid methyl ester (19)

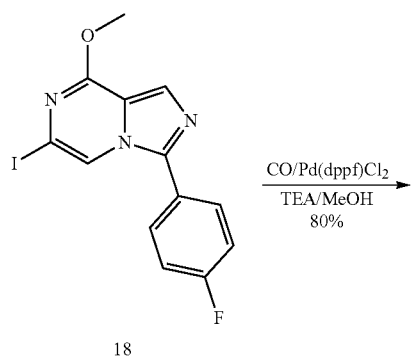

To a mixture solution of 18 (4.11 g, 11.13 mmol), CuI (640 mg, 3.34 mmol) and Pd(dppf)₂Cl₂ (930 mg, 1.11 mmol) in MeOH (100 mL) was added TEA (14 mL). The reaction mixture was heated to 85° C. under a CO atmosphere (3.0 MPa) for 16 hours. The reaction mixture was allowed to cool to room temperature and concentrated in vacuo to get the crude product. The residue was purified by column chromatography on silica gel (eluted with PE/EtOAc=1:1) to afford 19 (2.3 g, 75% yield) as a solid.

¹H NMR (400 MHz, CDCl₃): δ 8.59 (s, 1H), 7.87 (s, 1H), 7.78 (m, 2H), 7.28 (m, 2H), 4.21 (s, 3H), 3.96 (s, 3H). MS Calcd.: 301; MS Found: 302 ([M+H]⁺).

Synthesis of [3-(4-Fluoro-phenyl)-8-methoxy-imidazo[1,5-a]pyrazin-6-yl]-methanol (20)

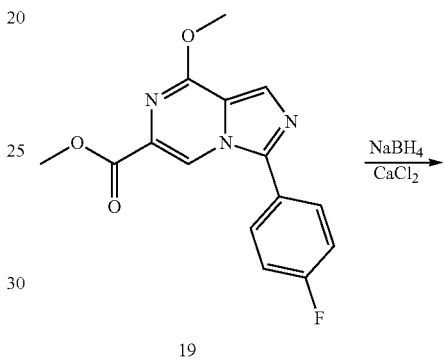

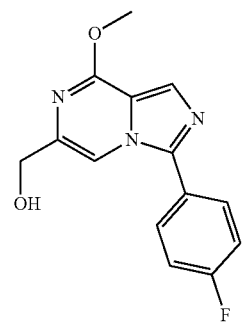

A mixture of powered anhydrous CaCl₂ (4.23 g, 38.15 mmol) and NaBH₄ (2.86 g, 76.3 mmol) in THF (100 mL) was stirred at room temperature for 1 hour. A solution of compound 19 (2.3 g, 7.63 mmol) in THF (25 mL) was added and then MeOH (25 mL) was added. The reaction mixture was stirred at room temperature for 1.5 hours. The mixture reaction was quenched with water (50 mL). After removing the organic solvent under reduced pressure, the resulting solution was dissolved in EtOAc (200 mL) and water (50 mL). The separated aqueous phase was extracted with EtOAc (3×100 mL). Then the combined organic phases were concentrated under reduced pressure. The residue was purified by column chromatography on silica gel (eluted with PE/EtOAc=2:1) to afford the desired product compound 20 (1.93, 93% yield) as a solid.

¹H NMR (400 MHz, CDCl₃): δ 7.81 (s, 1H), 7.79-7.74 (m, 3H), 7.25-7.22 (m, 2H), 4.56 (d, J=4.4 Hz, 2H), 4.11 (s, 3H), 2.41 (t, J=4.4 Hz, 1H). MS Calcd.: 273; MS Found: 274 ([M+H]⁺).

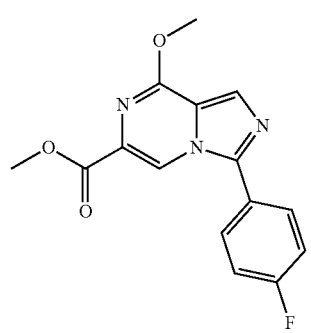

Synthesis of 6-Chloromethyl-3-(4-fluoro-phenyl)-8-methoxy-imidazo[1,5-a]pyrazine (21)

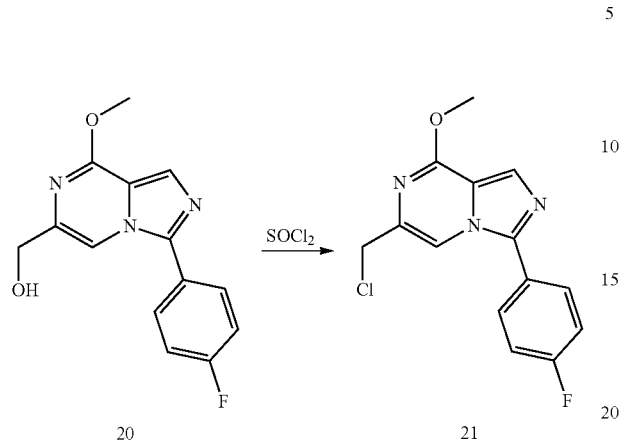

To a solution of 20 (1.88 g, 6.88 mmol) in dichloromethane (100 mL) was added dropwise thionyl chloride (4.5 mL) while cooling on an ice-water bath. After the addition, the mixture was stirred for another 2 hours. The reaction mixture was quenched with ice-water, washed with brine (20 mL), dried over $Na_2SO_4$ and concentrated in vacuo to afford 21 (2.01 g, 100% yield) as a solid.

$^1$H NMR (400 MHz, $CDCl_3$): δ 7.87 (s, 1H), 7.83-7.79 (m, 3H), 7.30-7.27 (m, 2H), 4.50 (s, 2H), 4.12 (s, 3H). MS Calcd.: 291; MS Found: 292 ([M+H]$^+$).

Synthesis of 6-Chloromethyl-3-(4-fluoro-phenyl)-7H-imidazo[1,5-a]pyrazin-8-one (22)

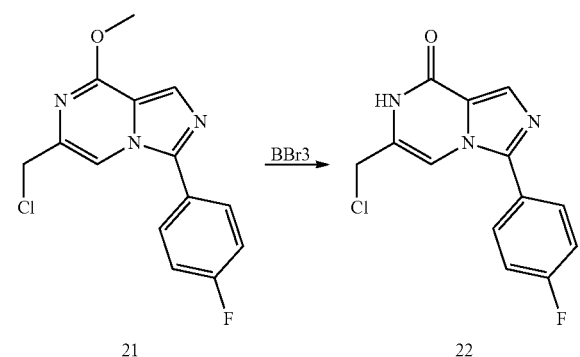

To a solution of 21 (1.87 g, 6.41 mmol) in MeOH (50 mL) was added 6N aqueous HCl and the resulting solution was stirred at 70° C. for one hour. The mixture was concentrated to afford the product 22 (1.60 g, 90% yield) as a white solid.

$^1$H NMR (300 MHz, DMSO-d6): δ 11.29 (s, 1H), 8.07 (s, 1H), 7.83-7.87 (m, 2H), 7.74 (s, 1H), 7.46-7.50 (m, 2H), 4.59 (s, 2H). MS Calcd.: 277; MS Found: 278 ([M+H]$^+$).

Synthesis of 4-(Azetidin-3-yloxy)-pyridine hydrochloride salt (5)

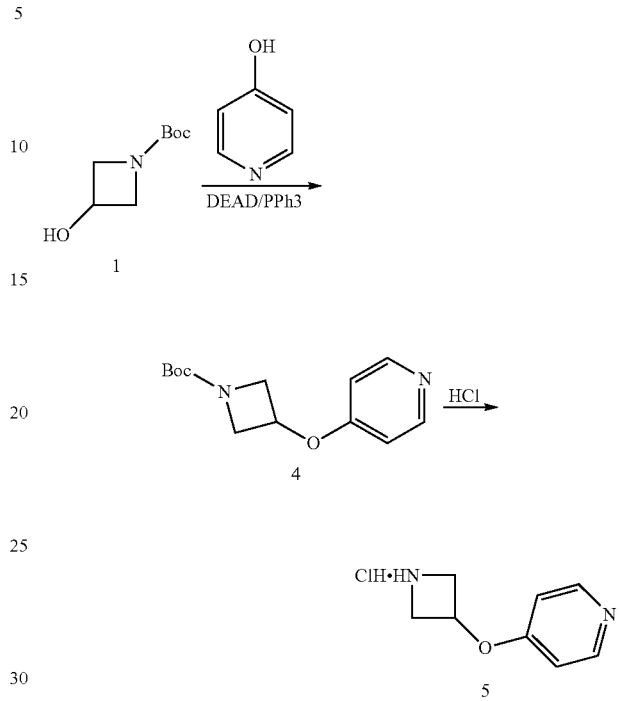

To a solution of tert-butyl 3-hydroxyazetidine-1-carboxylate 1 (4.55 g, 26.3 mmol) in THF (100 mL) was added pyridin-4-ol (2.0 g, 21.0 mmol), $PPh_3$ (6.89 g, 26.3 mmol) and DEAD (4.57 g, 26.3 mmol). The resulting reaction mixture was stirred at 70° C. overnight. TLC indicated that the reaction was complete. The reaction mixture was concentrated in vacuum. The resulting oil was dissolved in 1.0 M aqueous HCl solution (20 mL) and extracted with DCM (50 mL×3), The combined organic phases were washed with HCl (aq) solution (0.5 M, 150 mL). The aqueous fractions were combined and basified to pH≈12 using NaOH (1.0 M) and extracted with DCM (100 mL×3). The combined organic phases were dried over anhydrous $Na_2SO_4$, filtered and concentrated in vacuum. The residue was purified by column chromatography on silica gel to afford to afford 4 (2.81 g, 53% yield) as a solid.

$^1$HNMR (400 MHz, DMSO-d6): δ 8.41 (d, J=6.0 Hz, 2H), 6.88 (d, J=6.0 Hz, 2H), 5.07-5.09 (m, 1H), 4.32-4.33 (m, 2H), 3.80-3.82 (m, 2H), 1.39 (s, 9H). MS Calcd.: 250; MS Found: 251 ([M+H]$^+$).

To a solution of 4 (2.81 g, 11.2 mmol) in $Et_2O$ (100 mL) was added HCl in $Et_2O$ (20 mL). The resulting reaction mixture was stirred at room temperature overnight. TLC indicated that the reaction was complete. The reaction mixture was filtered and the solid was dried to afford 5 (1.82 g, 87% yield).

$^1$HNMR (300 MHz, DMSO-d6): δ 9.58 (s, 2H), 8.77-8.79 (m, 2H), 7.48-7.49 (m, 2H), 5.40-5.45 (m, 1H), 4.49-4.51 (m, 2H), 4.07-4.11 (m, 2H). MS Calcd.: 150; MS Found: 151 ([M+H]$^+$).

Synthesis of 3-(4-fluorophenyl)-6-((3-(pyridin-4-yloxy)azetidin-1-yl)methyl)imidazo[1,5-a]pyrazin-8(7H)-one (P1)

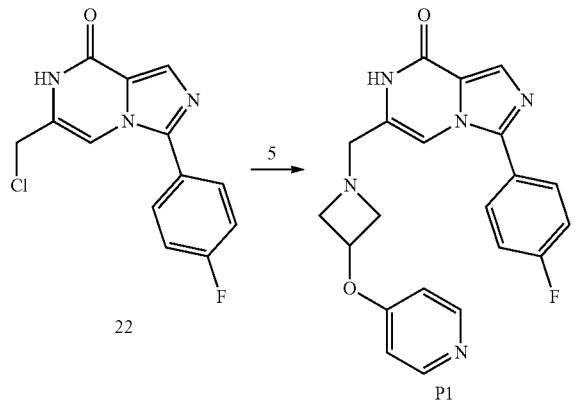

To a mixture of compound 22 (1.5 g, 5.4 mmol) and 5 (1.31 g, 7.0 mmol) in MeCN (100 mL) was added DIPEA (6.96 g, 5.4 mmol). The reaction mixture was heated and refluxed overnight. The solvent was removed in vacuum. The residue was purified by flash column chromatography on reverse phase silica gel (eluted by 5%-95% MeCN in water) to afford desired product P1 (1.28 g, 62% yield) as a solid.
¹H NMR (400 MHz, DMSO-d6): δ 10.7 (s, 1H), 8.37 (d, J=6.0 Hz, 2H), 7.85 (s, 1H), 7.85-7.82 (m, 2H), 7.42 (m, 2H), 7.34 (s, 1H), 6.86 (d, J=6.0 Hz, 2H), 4.93 (m, 1H), 3.88-3.77 (m, 2H), 3.42 (s, 2H), 3.18-3.14 (m, 2H). MS Calcd.: 391; MS Found: 392 ([M+H]⁺).

Synthesis of (6-Methoxy-5-{[(tetrahydro-pyran-4-carbonyl)-amino]-methyl}-pyrazin-2-yl)-carbamic acid tert-butyl ester (23)

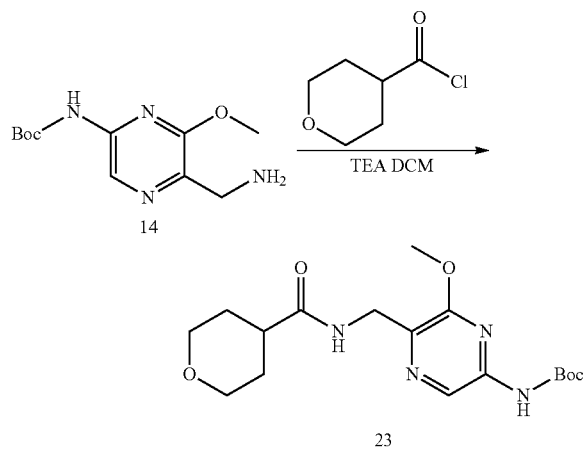

To a solution of compound 14 (28.4 g, 0.11 mol) in DCM (200 mL) was added TEA (49 mL, 0.34 mol), then tetrahydropyran-4-carbonyl chloride (17.5 g, 0.13 mol) was added dropwise. The resulting reaction mixture was stirred at room temperature overnight. TLC indicated that the reaction was complete. The reaction was quenched with water (100 mL). The organic phase was separated and the aqueous phase was extracted with DCM (200 mL×2). The combined organic phases were dried over anhydrous Na₂SO₄, filtered and concentrated in vacuum. The residue was purified by column chromatography on silica gel (PE/EA=5/1 to 1/3) to afford 23 (31 g, 75% yield) as a solid.
¹H NMR (DMSO-d6, 400 MHz): δ 9.89 (s, 1H), 8.47 (s, 1H), 8.10-8.07 (t, J=5.2 Hz, 1H), 4.29-4.28 (d, J=5.2 Hz, 2H), 3.87 (s, 3H), 3.85-3.82 (m, 2H), 3.32-3.25 (m, 2H), 2.45-2.43 (m, 1H), 1.60-1.55 (m, 4H), 1.48 (s, 9H). MS Calcd.: 366; MS Found: 367 ([M+H]⁺).

Synthesis of Tetrahydro-pyran-4-carboxylic acid (5-amino-3-methoxy-pyrazin-2-ylmethyl)-amide (24)

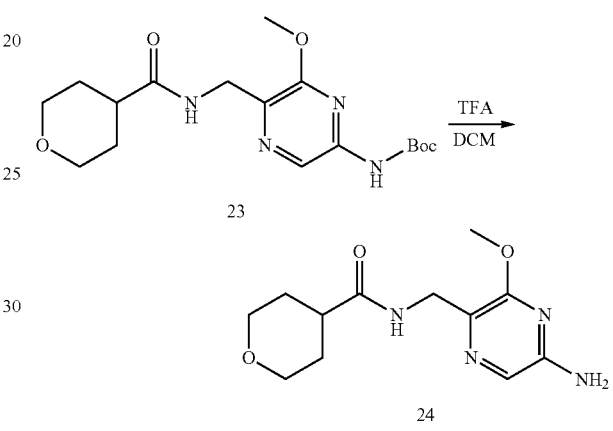

Compound 23 (19.0 g, 0.08 mol) was dissolved in DCM (100 mL). TFA (100 mL) was added. The reaction was stirred at room temperature overnight. TLC indicated that the reaction was complete. The solvent was removed. The residue was diluted with DCM (100 mL) and saturated NaHCO₃ aqueous solution (100 mL). The aqueous phase was extracted with DCM (100 mL×2). The combined organic phases were dried over anhydrous Na₂SO₄, filtered and concentrated in vacuum. The residue was purified by column chromatography on silica gel (PE/EA=6/1 to 1/1) to afford 24 (19 g, 85% yield) as a solid.
¹H NMR (DMSO-d6, 400 MHz): δ 7.87 (t, J=4.8 Hz, 1H), 7.36 (s, 1H), 6.26 (br. s, 2H), 4.16 (d, J=4.8 Hz, 2H), 3.86-3.82 (m, 2H), 3.80 (s, 3H), 3.30-3.24 (m, 2H), 2.41 (m, 1H), 1.59-1.54 (m, 4H). MS Calcd.: 266; MS Found: 267 ([M+H]⁺).

Synthesis of Tetrahydropyran-4-carboxylic acid (5-iodo-3-methoxy-pyrazin-2-ylmethyl)-amide (25)

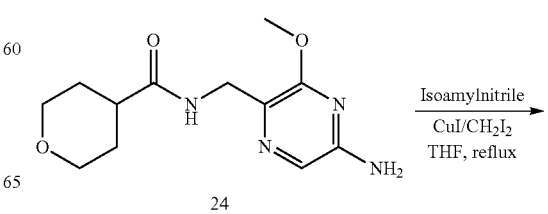

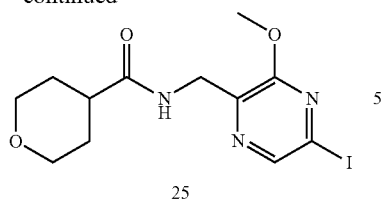

25

To a mixture of compound 24 (15.5 g, 58.4 mmol), CH$_2$I$_2$ (23.5, 87.6 mmol) and isoamyl nitrite (23.9 g, 204 mmol) in THF (600 mL) was added CuI (11.3 g, 39.6 mmol) under an N$_2$ atmosphere. The reaction mixture was stirred at 80° C. for 7 hours. The precipitate was filtered. The filtrate was concentrated and purified by column chromatography (MeOH/DCM=1/20) to get crude product, then purified by flash column chromatography on reverse phase silica gel (eluted by 5%-95% MeCN in water) to afford desired product compound 25 (4.5 g, 20% yield) as a solid.

$^1$HNMR (DMSO-d6, 300 MHz): δ 8.41 (s, 1H), 8.16 (t, J=5.4 Hz, 1H), 4.28 (d, J=5.4 Hz, 2H), 3.92 (s, 3H), 3.87-3.81 (m, 2H), 3.30-3.24 (m, 2H), 2.49 (m, 1H), 1.60-1.56 (m, 4H). MS Calcd.: 377 MS Found: 378 ([M+H]$^+$).

Synthesis of 6-Iodo-8-methoxy-3-(tetrahydro-pyran-4-yl)-imidazo[1,5-a]pyrazine (26)

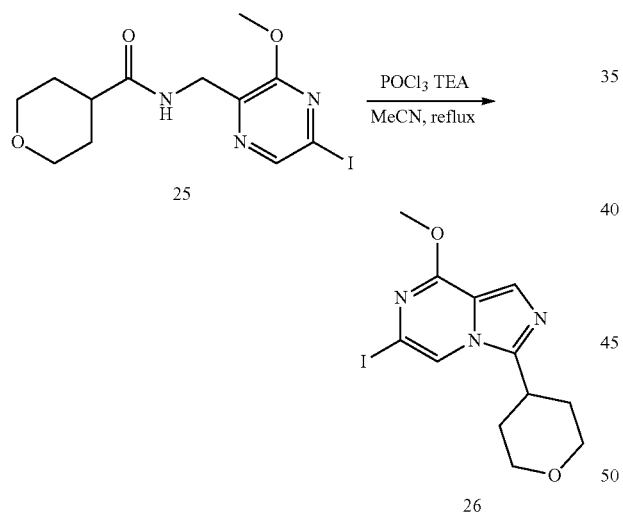

To a solution of compound 25 (4.5 g, 16.9 mmol) in MeCN (100 mL) was added POCl$_3$ (18 g, 118 mmol). The reaction was stirred at reflux overnight under an N$_2$ atmosphere. The solvent was removed under reduced pressure. The residue was treated with ice water (30 mL) and DCM (150 mL). The pH was adjusted to 7~8 by saturated Na$_2$CO$_3$ solution. The separated aqueous phase was extracted with DCM (100 mL×4). The combined organic phases were concentrated under reduced pressure to afford desired 26 (4.2 g, 99% yield) as a solid.

$^1$HNMR (DMSO-d6, 400 MHz): δ 8.46 (s, 1H), 7.64 (s, 1H), 3.98 (s, 3H), 3.94 (m, 2H), 3.53-3.47 (m, 3H), 1.81-1.77 (m, 4H). MS Calcd.: 359; MS Found: 360 ([M+H]$^+$).

Synthesis of 8-Methoxy-3-(tetrahydro-pyran-4-yl)-imidazo[1,5-a]pyrazine-6-carboxylic acid methyl ester (27)

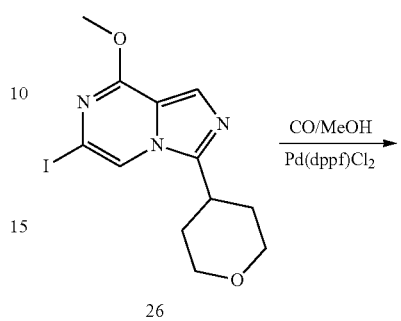

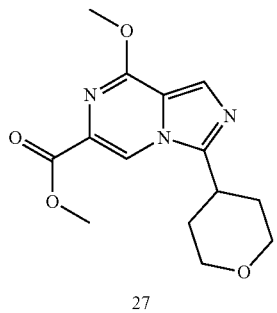

To a suspension of compound 26 (4.2 g, 11.7 mmol) in MeOH (100 mL) was added CuI (0.7 g, 3.0 mmol), Pd(dppf)$_2$Cl$_2$ (1.0 g, 1.17 mmol) and TEA (16 mL). The reaction mixture was stirred on an oil bath set at 85° C. for 16 hours under a CO atmosphere (3 MPa). The precipitate was filtered and the filtrate was evaporated under reduced pressure. The residue was purified by column chromatography (eluted by EtOAc/PE=2/1 to MeOH/DCM=1/20) to afford desired 27 (2.7 g, 80% yield) as a solid.

$^1$H NMR (CDCl$_3$, 400 MHz): δ 8.32 (s, 1H), 7.70 (s, 1H), 4.17 (s, 3H), 4.14 (m, 2H), 3.98 (s, 3H), 3.66-3.60 (m, 2H), 3.31-3.26 (m, 1H), 2.17-2.13 (m, 2H), 1.93 (m, 2H). MS Calcd.: 291; MS Found: 292 ([M+H]$^+$).

Synthesis of [8-Methoxy-3-(tetrahydro-pyran-4-yl)-imidazo[1,5-a]pyrazin-6-yl]-methanol (28)

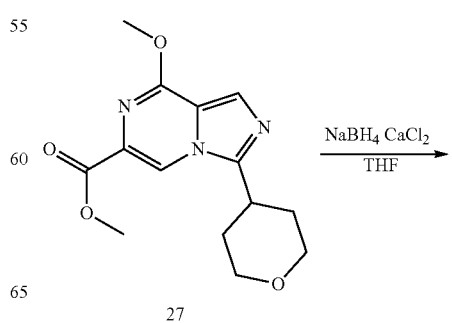

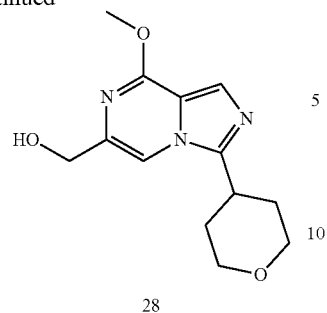

A mixture of powered anhydrous CaCl$_2$(2.4 g, 21.5 mmol) and NaBH$_4$(1.6 g, 42.9 mmol) was stirred in THF (100 mL) for 1 hour at rt. A solution of compound 27 (2.4 g, 4.29 mmol) in THF (25 mL) was added and then MeOH (25 mL) was added. The reaction mixture was stirred at room temperature for 1.5 hours. The mixture reaction was quenched with water (50 mL). After removing the organic solvent under reduced pressure, the residue was partitioned between EtOAc (200 mL) and water (50 mL). The separated aqueous phase was extracted with EtOAc (100×3 mL). Then the combined organic phases were concentrated under reduced pressure. The residue was purified by column chromatography on silica gel (eluted by DCM/MeOH=100/1 to 30/1) to afford the desired product compound 28 as a solid (1.87, 80% yield).

$^1$H NMR (CDCl$_3$, 400 MHz): δ 7.65 (s, 1H), 7.43 (s, 1H), 4.58 (s, 2H), 4.13 (d, J=12.0 Hz, 2H), 4.07 (s, 3H), 3.60 (dd, J=10.4 Hz, 10.8 Hz, 2H), 3.24-3.17 (m, 1H), 2.60 (m, 1H), 2.18-2.06 (m, 2H), 1.90 (d, J=12.8 Hz, 2H). MS Calcd.: 263; MS Found: 264 ([M+H]$^+$).

Synthesis of 6-Chloromethyl-3-(tetrahydropyran-4-yl)-7H-imidazo[1,5-a]pyrazin-8-one (30)

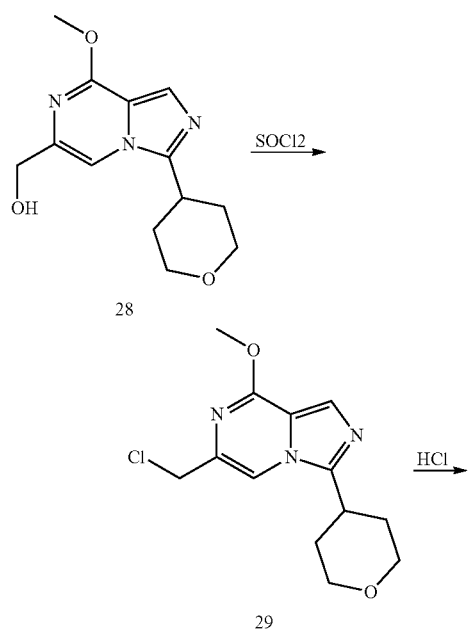

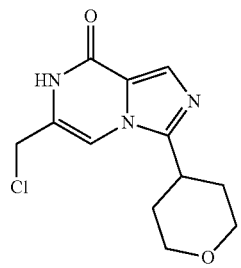

To a solution of compound 28 (1.9 g, 7.11 mmol) in DCM (100 mL) was added SOCl$_2$ (5 mL) at 0° C., then the reaction mixture was stirred at room temperature for 5 hours. TLC and LC-MS showed that the starting martial had been consumed. Then the mixture solution was concentrated and the residue was dissolved in HCl (aq.) solution (6N, 20 mL). The mixture reaction was stirred at room temperature for 10 minutes. The reaction mixture was then concentrated under reduced pressure to afford the desired product compound 29 (1.90 g, 95% yield) as a solid.

$^1$H NMR (DMSO-d6, 300 MHz): δ 11.49 (s, 1H), 8.28 (s, 1H), 8.00 (s, 1H), 4.55 (s, 2H), 3.97 (dd, J=2.4 Hz, 2.8 Hz, 2H), 3.53-3.43 (m, 3H), 1.95-1.81 (m, 4H). MS Calcd.: 267 MS Found: 268 ([M+H]$^+$).

Synthesis of 3-(azetidin-3-yloxy)-pyridine hydrochloride (7)

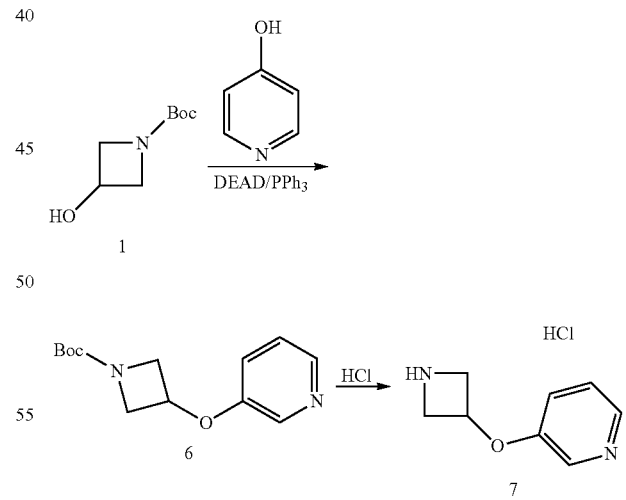

Compound 7 was prepared by a similar procedure to the one employed for the preparation of amine 5.

Analytical data for 7: $^1$HNMR ((DMSO-d6, 400 MHz): δ 9.73 (br d, 2H), 8.55 (d, J=2.4 Hz, 2H), 8.47 (d, J=4.4 Hz, 2H), 7.88-7.75 (m, 2H), 5.28 (t, J=5.6 Hz, 1H), 4.50-4.43 (m, 2H), 4.08-4.00 (m, 2H). MS Calcd.: 150, MS Found: 151 ([M+H]$^+$).

Synthesis of 6-[3-(pyridin-3-yloxy)-azetidin-1-ylm-ethyl]-3-(tetrahydropyran-4-yl)-7H-imidazo[1,5-a]pyrazin-8-one (P2)

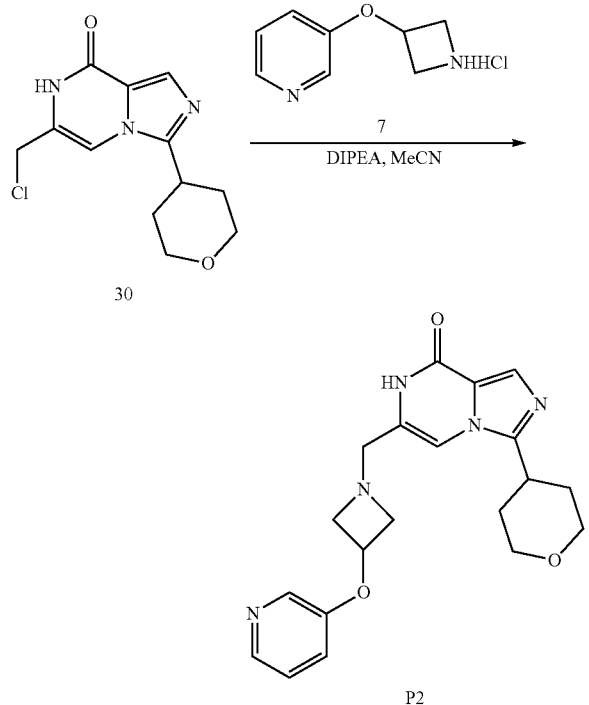

To a mixture of compound 30 (550 mg, 2.05 mmol) and 7 (500 mg, 2.67 mmol) in MeCN (200 mL) was added DIPEA (2.7 g, 20.5 mmol). The reaction mixture was refluxed overnight. The solvent was removed in vacuum. The crude product was purified by flash column chromatography on reverse phase silica gel (eluted by 5%-95% MeCN in water) to afford desired product P2 (360 mg, 46% yield) as a solid.

$^1$H NMR (CDCl$_3$, 300 MHz): δ 8.26 (d, J=4.0 Hz 1H), 8.22 (s, 1H), 8.20 (d, J=2.8 Hz, 1H), 7.91 (s, 1H), 7.24-7.21 (m, 1H), 7.07 (d, J=2.8 Hz, 1H), 6.79 (s, 1H), 4.86 (m, 1H), 4.13 (m, 2H), 3.89 (t, J=7.6 Hz, 2H), 3.57 (m, 2H), 3.50 (s, 2H), 3.28 (dd, J=2.4 Hz, 6.8 Hz, 2H), 3.10-30.6 (m, 1H), 2.14-2.08 (m, 2H), 1.87 (m, 2H). MS Calcd.: 381; MS Found: 382 ([M+H]$^+$).

Synthesis of 3H-imidazole-4-carboxylic acid methyl ester (32)

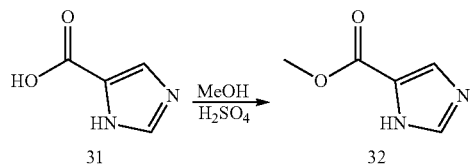

To a solution of compound 31 (25 g, 0.22 mol) in MeOH (300 mL) was added H$_2$SO$_4$ (24 mL). The mixture was stirred at reflux for 18 hours. Then pH of the reaction solution was adjusted to ~7. The reaction mixture was concentrated in vacuo. The residue was dissolved in 100 ml of MeOH and stirred at room temperature for 15 minutes. The mixture solution was filtered and the filtrate was concentrated to afford the crude 32 (28 g, 100% yield) as a solid, which was used for next step without further purification.

$^1$H NMR (400 MHz, DMSO-d6): δ 7.80 (s, 2H), 3.57 (s, 3H).

Synthesis of 3H-imidazole-4-carboxylic acid methyl ester (33)

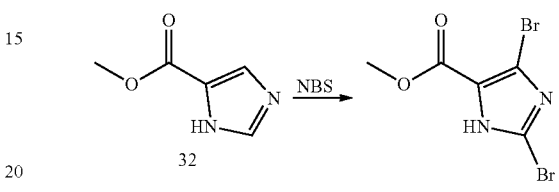

To a solution of compound 32 (22 g, 0.18 mol) in MeCN (500 mL) was added NBS (66 g, 0.37 mol). The mixture was stirred at 70° C. for 4 hours. The reaction mixture was concentrated in vacuo. The crude product was purified by column chromatography on silica gel (eluting with PE/EtOAc=5:1 to 1:1) to afford compound 33 (20 g, 40% yield) as a solid.

$^1$H NMR (400 MHz, DMSO-d6): δ 14.35 (br, 1H), 3.81 (s, 3H).

Synthesis of racemic trans-1-benzyl-4-methyl-pyrrolidine-3-carboxylic acid ethyl ester (35)

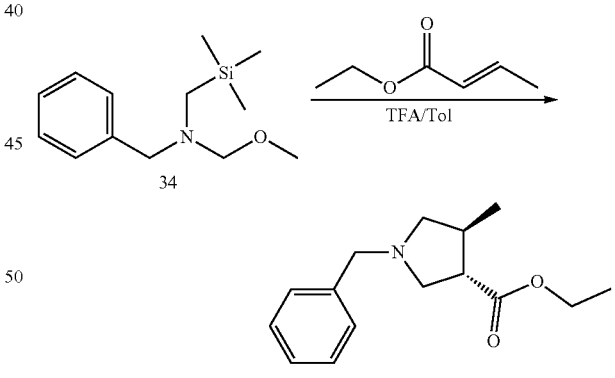

To a solution of 34 (69 g, 0.29 mol) in toluene was added but-2-enoic acid ethyl ester (50 g, 0.44 mol) and TFA (25 mL, 0.32 mol). The resulting solution was stirred at 50° C. under N$_2$ overnight. To the reaction mixture was added saturated aqueousNaHCO$_3$ solution (300 mL), and the aqueous phase was extracted with EtOAc (500 mL×3). The combined organic layers were washed with brine (300 mL), dried over Na$_2$SO$_4$, filtered and concentrated in vacuo. The crude product was purified by flash chromatography (PE/EA=20:1 to 6:1) to afford the desired racemic trans product 35 (41 g, 57% yield) as an oil.

Synthesis of (S,S)-trans-1-benzyl-4-methyl-pyrrolidine-3-carboxylic acid ethyl ester (S,S)-(35)

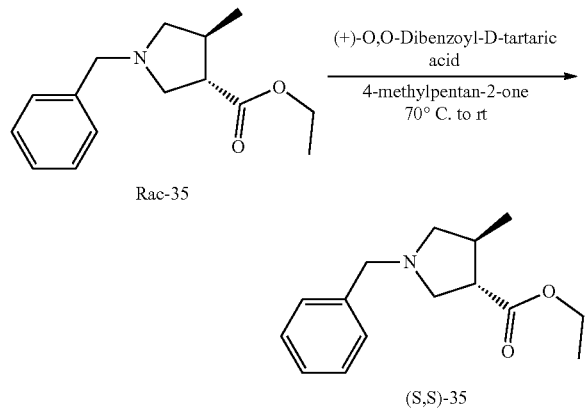

To a solution of Rac-35 (37 g, 0.15 mol) in 4-methyl-2-pentanone was added (−)-dibenzoyl-L-tartaric acid (34.78 g, 0.65 eq.) and the resulting reaction mixture was heated to 72° C. for 1 hr after which it was allowed to cool to RT where it was maintained for 4 hrs. The resulting solid was filtered off and the filtrate was washed with conc. aq. sodium carbonate (55 mL). The aqueous phase was extracted with 4-methyl-2-pentanone (15 mL) and the combined organic phases were washed with brine (40 mL). The organic phase was then treated with (+)-dibenzoyl-D-tartaric acid (32.16 g) and heated to 72° C. for 1 hr. The reaction mixture was cooled to RT and maintained at this temperature for 4 hrs. The solid was filtered off and dried on the filter. The solid was then recrystallized by adding a mixture of MTBE-MeOH (2:1, 270 mL), heating to 70° C. for 1 hr and allowing the product to precipitate at RT for 4 hrs. The resulting solid was filtered off, washed with MTBE and dried. Two more recrystallization following the same procedure afforded the pure product as a (+)-dibenzoyl-D-tartaric acid salt (>98% ee with based on the isolated free base).

The free base was liberated by the following procedure: the filtered solid was partitioned between MTBE (250 mL) and conc. aq. sodium carbonate (250 mL) and the aqueous phase was extracted with MTBE (125 mL). The combined organic phases were washed with water (250 mL) and brine (50 mL) and evaporated to give the product as a clear oil (13.79 g, 0.056 mol) as a clear oil.

Synthesis of racemic trans-4-methyl-pyrrolidine-1,3-dicarboxylic acid 1-tert-butyl ester 3-methyl ester rac-(36)

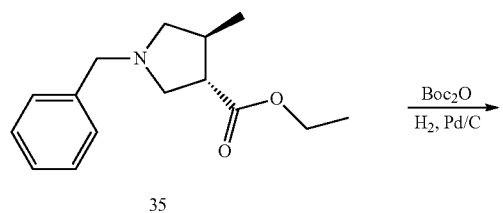

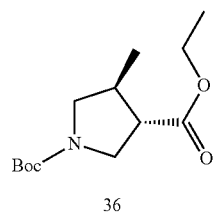

To a solution of 35 (41 g, 0.17 mol) and Boc₂O (43 g, 0.20 mol) in EtOH (500 mL) was added Pd/C (5%, 10.0 g). The reaction mixture was stirred at 50° C. for 48 hours under an atmosphere of H₂ (50 Psi). The reaction mixture was filtered and concentrated in vacuo. The crude product was purified by flash chromatography (PE/EA=20/1) to afford the desired racemic trans 36 (20 g, 46% yield) as an oil.

Synthesis of (S,S)-trans-4-methyl-pyrrolidine-1,3-dicarboxylic acid 1-tert-butyl ester (S,S)-(37) via (S,S)-trans-4-methyl-pyrrolidine-1,3-dicarboxylic acid 1-tert-butyl ester 3-methyl ester (S,S)-(36)

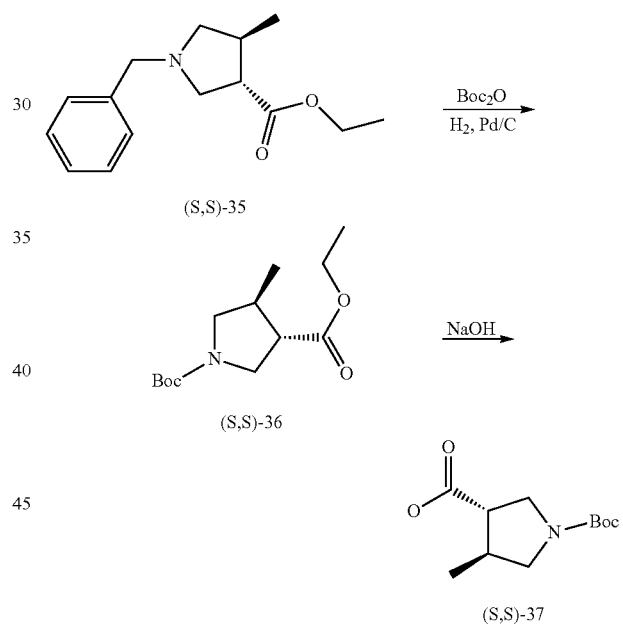

A solution of (S,S)-35 (12.80 g, 51.8 mmol) and Boc₂O (13.57 g, 1.2 eq) in EtOH (150 mL) was placed in an autoclave under N₂-protective atmosphere and Pd/C (5%, 2.56 g) was added. The reaction mixture was hydrogenated with stirring at 45-50° C. at 15-20 Bar H₂ pressure until no more hydrogen was absorbed (48 hrs). The reaction mixture was cooled to RT and filtered, and the filter was washed with EtOH (50 mL). The filtrate was evaporated at <45° C. to about 25 mL. Water (10 mL) and NaOH solution (2 mL) was added and the resulting reaction mixture was stirred at RT for 2 hrs (GC analysis showed complete disappearance of the starting material at this point). Water (125 mL) was added and the resulting mixture was extracted with MTBE (2×50 mL). The aqueous phase was treated with 2N HCl solution to achieve a pH value of 3-4 (ca. 25 mL) and the resulting solution was extracted with MTBE (2×150 mL).

The combined organic extracts were washed with brine (50 mL) and evaporated to about 20 mL. n-Heptane (40 mL) was added and the resulting reaction mixture was left at 0° C. for 2 hrs after which the solid was filtered off and dried to give the product (S,S)-37 as a solid (9.48 g, 41.7 mmol). The ee at this step was determined to 97.5%. This material had identical NMR and LC/MS properties to rac-37 described below.

Synthesis of (S,S)-trans-4-methyl-pyrrolidine-1,3-dicarboxylic acid 1-tert-butyl ester (S,S)-(37) via (S,S)-trans-4-methyl-pyrrolidine-1,3-dicarboxylic acid 1-tert-butyl ester 3-methyl ester (S,S)-(36)

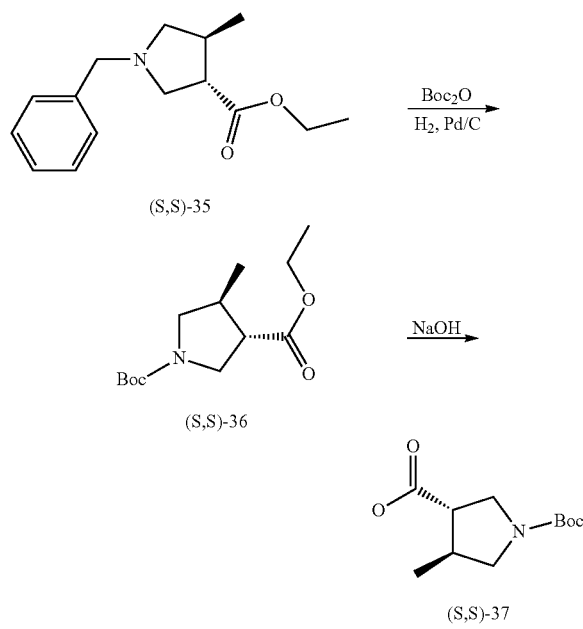

A solution of (S,S)-35 (12.80 g, 51.8 mmol) and Boc₂O (13.57 g, 1.2 eq) in EtOH (150 mL) was placed in an autoclave under N₂-protective atmosphere and Pd/C (5%, 2.56 g) was added. The reaction mixture was hydrogenated with stirring at 45-50° C. at 15-20 Bar H₂ pressure until no more hydrogen was absorbed (48 hrs). The reaction mixture was cooled to RT and filtered, and the filter was washed with EtOH (50 mL). The filtrate was evaporated at <45° C. to about 25 mL. Water (10 mL) and NaOH solution (2 mL) was added and the resulting reaction mixture was stirred at RT for 2 hrs (GC analysis showed complete disappearance of the starting material at this point). Water (125 mL) was added and the resulting mixture was extracted with MTBE (2×50 mL). The aqueous phase was treated with 2N HCl solution to achieve a pH value of 3-4 (ca. 25 mL) and the resulting solution was extracted with MTBE (2×150 mL). The combined organic extracts were washed with brine (50 mL) and evaporated to about 20 mL. n-Heptane (40 mL) was added and the resulting reaction mixture was left at 0° C. for 2 hrs after which the solid was filtered off and dried to give the product (S,S)-37 as a solid (9.48 g, 41.7 mmol). The ee at this step was determined to 97.5%. This material had identical NMR and LC/MS properties to rac-37 described below.

Synthesis of racemic trans-4-methyl-pyrrolidine-1,3-dicarboxylic acid 1-tert-butyl ester (37)

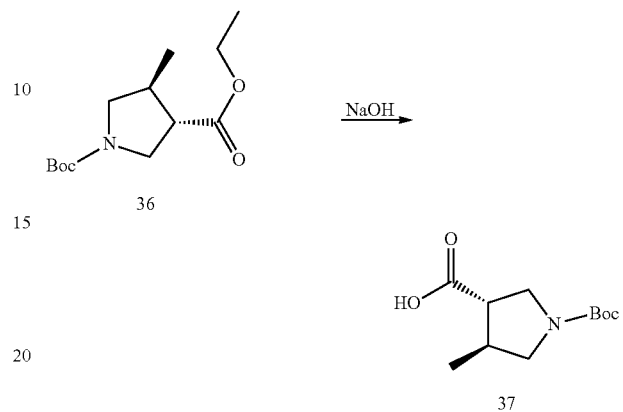

A solution of compound 36 (10.0 g, 39.1 mmol), NaOH (3.10 g, 78.2 mmol) in methanol/H₂O (50/5 mL) was stirred at room temperature for 2 hours. The reaction mixture was concentrated and extracted with EA (150 mL). The aqueous phase was acidified by 2 M HCl at 0° C. to pH ~5 and extracted with EtOAc (150 mL×3). The combined organic layers were washed with brine, dried and concentrated to afford compound 37 (8.0 g, 90%) as an oil.

$^1$H NMR (400 MHz, DMSO-d6): δ 12.43 (s, 1H), 3.55-3.51 (m, 2H), 3.47-3.27 (m, 1H), 2.85-2.78 (m, 1H), 2.63-2.57 (m, 1H), 2.34-2.28 (m, 1H), 1.55 (s, 9H), 1.03 (d, J=4.8 Hz, 3H).

Synthesis of (S,S)-trans-3-acetyl-4-methyl-pyrrolidine-1-carboxylic acid tert-butyl ester (S,S)-(39) via (S,S)-trans-3-(methoxy-methyl-carbamoyl)-4-methyl-pyrrolidine-1-carboxylic acid tert-butyl ester (S,S)-(38)

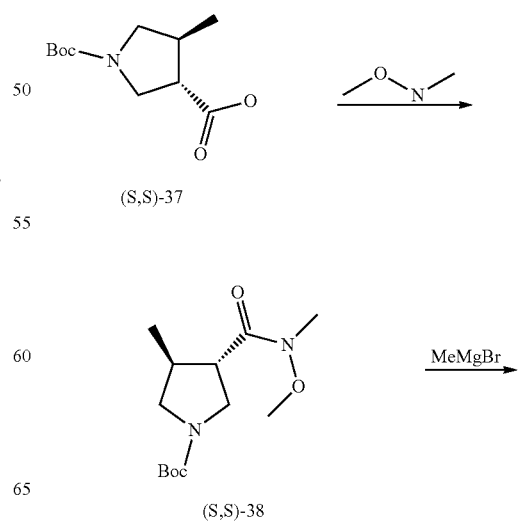

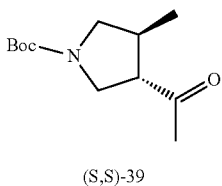

(S,S)-39

To a solution of (S,S)-37 (5.0 g, 22.0 mmol) in DCM (50 mL) was added CDI (4.25 g, 1.2 eq) over 10 mins while keeping the temperature below 5° C. throughout. The reaction mixture was stirred for 1 hr after which N,O-dimethylhydroxylamine hydrochloride (3.0 g, 1.4 eq) was added in small portions over about 10 mins keeping the temperature below 5° C. The reaction was then allowed to warm to room temperature and stirred for 12 hrs at which the starting material had been fully consumed. Water (50 mL) was added, the phases were separated and the aq phase was extracted with DCM (35 mL). The combined organic phases were washed with water (50 mL) and concentrated to about 5 mL. THF (20 mL) was added and the resulting solution was evaporated to dryness and dried in high vacuum. Dry THF (50 mL) was added, the solution was cooled to 0° C. and MeMgCl (3 M, 11.35 mL, 1.5 eq) was added dropwise under an $N_2$ atmosphere over 30 mins making sure to maintain the temperature below 5° C. The reaction mixture was then heated to RT and stirred for 2 hrs (at this point the Weinreb amide had been completely converted). Saturated aq. ammonium chloride (50 mL) was added dropwise below 25° C. to quench the reaction and the resulting reaction mixture was extracted with EtOAc (2×50 mL), and the combined organic extracts were washed with brine (50 mL) and evaporated to about 5 mL. THF (25 mL) was added and the resulting solution was evaporated to dryness in vacuo to give the product (S,S)-39 as an oil (4.91 g, 21.6 mmol) in about 98% ee. All spectral properties were identical to those of rac-39.

Synthesis of racemic trans-3-(methoxy-methyl-carbamoyl)-4-methyl-pyrrolidine-1-carboxylic acid tert-butyl ester (38)

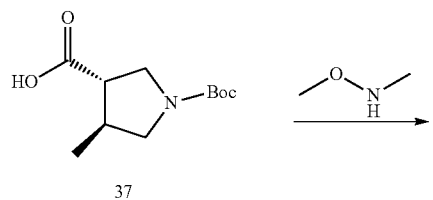

37

To a solution of 37 (8.0 g, 34.9 mmol) and O,N-dimethylhydroxylamine (4.0 g, 41.9 mmol) in DCM (50 mL) was added CDI (6.8 g, 41.9 mmol). The mixture reaction was stirred at 20° C. for 18 hours. To the mixture solution was added water (100 mL) and extracted with DCM (100 mL×3). The combined organic layers were washed with brine (30 mL), dried and concentrated in vacuo. The crude product was purified by flash chromatography (PE/EtOAc=20/1) to afford racemic trans 38 (8.0 g, 84% yield) as an oil.

$^1$H NMR (400 MHz, DMSO-d6): δ 3.68 (s, 3H), 3.60-3.48 (m, 2H), 3.20-3.05 (m, 5H), 2.84-2.73 (m, 1H), 2.40-2.32 (m, 1H), 1.39 (s, 9H), 0.96 (d, J=4.8 Hz, 3H).

Synthesis of racemic trans-3-acetyl-4-methyl-pyrrolidine-1-carboxylic acid tert-butyl ester (39)

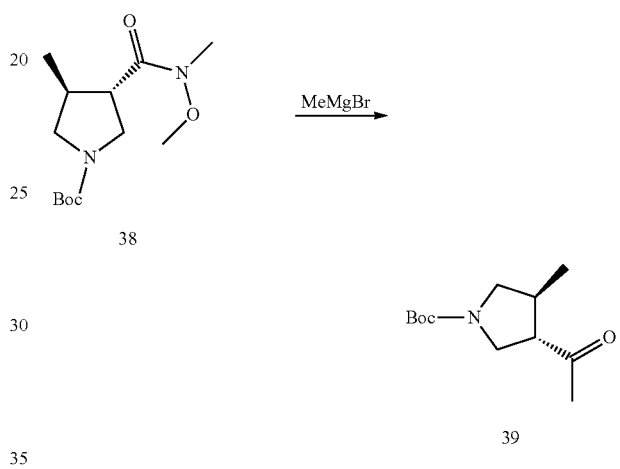

To a solution of 38 (8.0 g, 29.4 mmol) in THF (60 mL) was added MeMgBr (3.0 M, 13 mL, 38.2 mmol) at 0° C. The reaction mixture was stirred at room temperature for 2 hours. The mixture reaction was quenched with saturated NH$_4$Cl aqueous solution (200 mL) and extracted with EtOAc (300 mL×3). The combined organic layers were washed with brine, dried and concentrated in vacuo. The crude product was purified by flash chromatography (PE/EtOAc=10/1) to afford the desired racemic trans 39 (6.0 g, 94% yield) as an oil.

$^1$H NMR (400 MHz, DMSO-d6): δ 3.66-3.51 (m, 1H), 3.49-3.39 (m, 1H), 3.34-3.24 (m, 1H), 2.88-2.79 (m, 2H), 2.34-2.30 (m, 1H), 2.15 (s, 3H), 1.36 (s, 9H), 1.02-1.00 (m, 3H).

Synthesis racemic trans-3-(2-bromo-acetyl)-4-methyl-pyrrolidine-1-carboxylic acid tert-butyl ester (40)

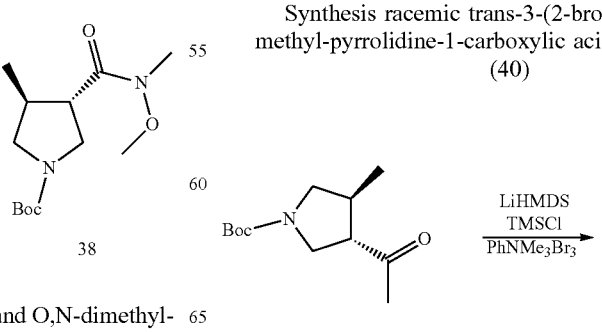

39

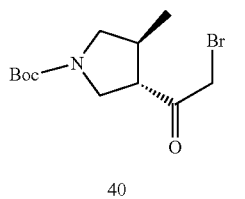

40

A solution of LiHMDS (1M in THF, 40 mL, 40 mmol) was added to the solution of 39 (6.0 g, 26.4 mmol) in THF (100 mL) under an N₂ atmosphere at −78° C. The reaction mixture was stirred at this temperature for one hour. Then TMSCl (10 mL, 26.4 mmol) was added dropwise at −78° C. and the reaction temperature was raised to 0° C. After one hour, PhMe₃NBr₃ (11.0 g, 29.1 mmol) was added at 0° C. The mixture reaction was stirred for another an hour, then stirred at room temperature overnight. The reaction was quenched with water (200 mL) and extracted with EtOAc (250 mL×3). The combined organic layers were washed with brine, dried and concentrated in vacuo. The crude product was purified by flash chromatography (PE/EtOAc=10/1) to afford the desired racemic trans 40 (4.5 g, 56% yield) as an oil.

¹H NMR (400 MHz, CDCl₃): δ 4.05 (s, 2H), 3.69-3.50 (m, 2H), 3.36-3.30 (m, 1H), 3.04-2.86 (m, 2H), 2.51-2.43 (m, 1H), 1.39 (s, 9H), 1.10-1.05 (m, 3H).

Synthesis (S,S)-trans-3-(2-bromo-acetyl)-4-methyl-pyrrolidine-1-carboxylic acid tert-butyl ester (S,S)-(40)

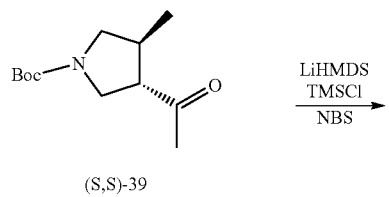

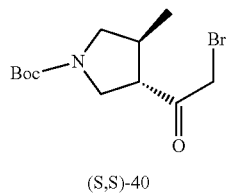

(S,S)-40

A solution of LiHMDS (1M in THF, 21.12 mL, 21.12 mmol) was added dropwise to a solution of (S,S)-39 (3.96 g, 17.4 mmol) in THF (50 mL) under an N₂ atmosphere at −78° C. The reaction mixture was stirred at this temperature for one hour. Then TMSBr (6.43 g, 42 mmol) was added dropwise at −78° C. and the reaction temperature was allowed to warm to 0° C. After one hour NBS (2.76 g, 15.5 mmol) was added in small portions at 0° C. TLC showed that all starting material had been consumed. Water (20 mL) was added dropwise keeping the temperature at RT and the resulting reaction mixture was stirred for 30 mins. The phases were separated and the aq phase was extracted with MTBE (2×15 mL). The combined organic phases were washed with brine, dried and concentrated in vacuo. The residue was redissolved in MTBE (25 mL), washed with water (3×10 mL) and brine (10 mL), and concentrated in vacuo to give the product as an oil which could be purified by flash chromatography (PE/EtOAc=10/1) to afford the desired (S,S)-40 (6.4 g, 20.9 mmol) as an oil.

Synthesis of racemic trans-2,5-dibromo-3-[2-(1-tert-butoxycarbonyl-4-methyl-pyrrolidin-3-yl)-2-oxo-ethyl]-3H-imidazole-4-carboxylic acid methyl ester (41)

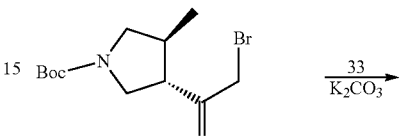

40

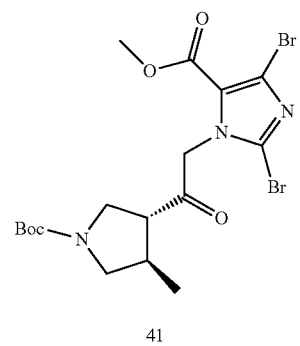

41

To a solution of 33 (4.1 g, 14.7 mmol) in DMF (30 mL) was added K₂CO₃ (5.8 g, 42.5 mmol). After stirring for 15 minutes, compound 40 (4.5 g, 14.7 mmol) was added to the reaction mixture. The reaction was stirred at room temperature for 5 hours. The reaction mixture was diluted with EtOAc (200 mL), washed with brine (200 mL×2). Then the organic phase was dried (Na₂SO₄), filtered and concentrated in vacuo. The residue was purified by column chromatography (PE/EtOAc=10/03/1) to afford racemic trans 41 (3.0 g, 40% yield) as a solid.

¹H NMR (400 MHz, DMSO-d6): δ 5.41 (s, 2H), 3.78 (s, 3H), 3.68-3.66 (m, 1H), 3.48-3.45 (m, 1H), 3.34-3.31 (m, 1H), 3.20-3.25 (m, 1H), 2.92-2.87 (m, 1H), 2.50-2.46 (m, 1H), 1.36 (s, 9H), 1.07 (m, 3H).

Synthesis of (S,S)-trans-2,5-dibromo-3-[2-(1-tert-butoxycarbonyl-4-methyl-pyrrolidin-3-yl)-2-oxo-ethyl]-3H-imidazole-4-carboxylic acid methyl ester (S,S)-(41)

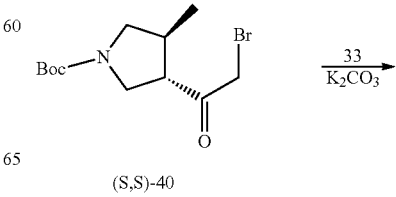

(S,S)-40

-continued

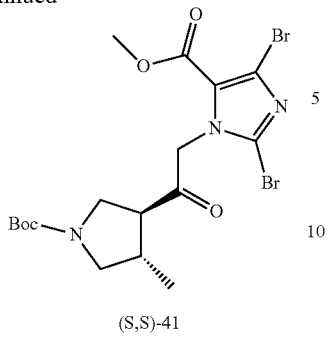

(S,S)-41

To a solution of 33 (2.78 g, 9.79 mmol) in NMP (30 mL) was added Na₂CO₃ (3.11 g, 26.2 mmol). After stirring for 15 minutes, compound (S,S)-40 (4.5 g, 14.7 mmol) was added to the reaction mixture. The reaction was stirred at room temperature for 5 hours. The reaction mixture was diluted with EtOAc (200 mL), washed with brine (200 mL×2). Then the organic phase was dried (Na₂SO₄), filtered and concentrated in vacuo. The residue was purified by column chromatography (PE/EtOAc=10/0~3/1) to give the product as a crude solid which was recrystallized from 2-propanol/n-heptane to give (S,S)-41 (3.03 g, 40% yield) as a solid. The ee of the material at this stage was determined to be above 99%. All spectral data were identical to those of rac-41.

Synthesis of racemic trans-3-(1,3-dibromo-8-oxo-7,8-dihydro-imidazo[1,5-a]pyrazin-6-yl)-4-methyl-pyrrolidine-1-carboxylic acid tert-butyl ester (42)

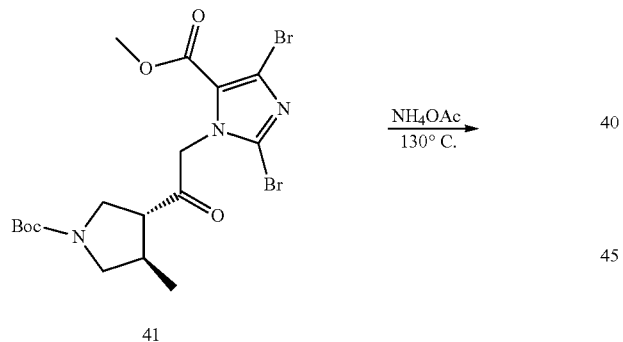

41

To a solution of 41 (3.0 g, 5.89 mmol) in MeOH (150 mL) was added NH₄OAc (9.07 g, 117.8 mmol). The reaction mixture was heated to 130° C. in a pressure vessel for 15 hours. The reaction mixture was filtered and concentrated to get the crude product. The residue was purified by column chromatography (DCM/MeOH=100/1~10/1) to afford racemic trans 42 (2.2 g, 80% yield) as a solid.

¹H NMR (400 MHz, DMSO-d6): δ 10.98 (br. s, 1H), 7.10 (s, 1H), 3.63-3.54 (m, 2H), 3.39-3.34 (m, 1H), 2.84-2.77 (m, 2H), 2.50 (m, 1H), 1.41 (s, 9H), 0.96 (m, 3H).

Synthesis of (S,S)-trans-3-(1,3-dibromo-8-oxo-7,8-dihydro-imidazo[1,5-a]pyrazin-6-yl)-4-methyl-pyrrolidine-1-carboxylic acid tert-butyl ester (S,S)-(42)

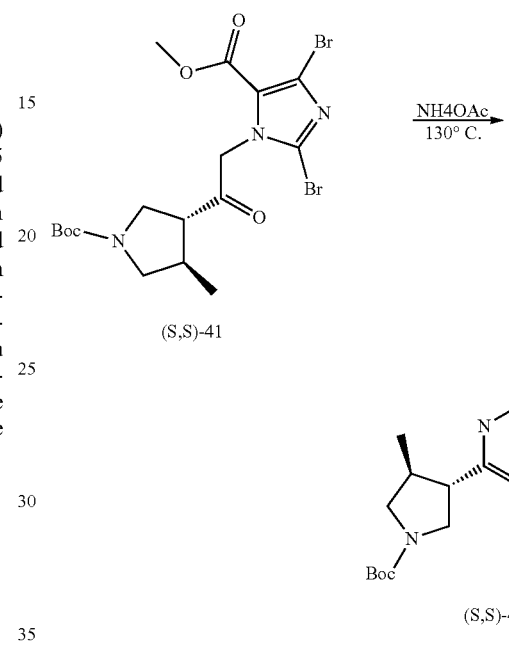

To a solution of (S,S)-41 (3.03 g, 5.9 mmol) in 2-propanol (20 mL) was added NH₄OAc (9.18 g, 118 mmol). The reaction mixture was heated at 105-110° C. for 12 hrs after which it was poured into water (60 mL) with stirring and left for two hrs. The reaction mixture was filtered and concentrated to get the crude product. The residue was purified by column chromatography (DCM/MeOH=100/1~10/1) and evaporated to afford (S,S)-42 (2.1 g, 4.4 mmol) as a solid. The material was determined to have 99.3% ee and similar spectral properties to those of rac-42.

Synthesis of racemic trans-3-[1-bromo-3-(3,6-dihydro-2H-pyran-4-yl)-8-oxo-7,8-dihydro-imidazo[1,5-a]pyrazin-6-yl]-4-methyl-pyrrolidine-1-carboxylic acid tert-butyl ester (43)

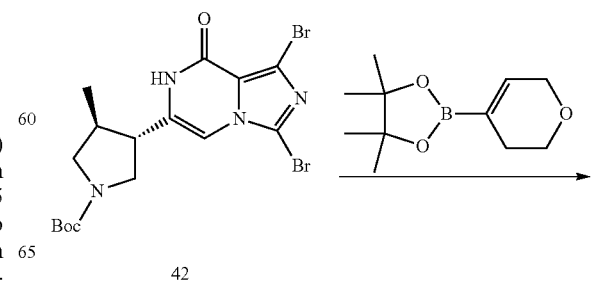

42

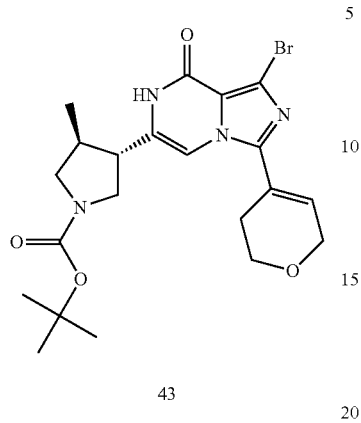

43

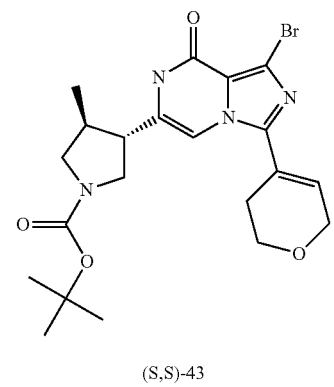

(S,S)-43

To a mixture of compound 42 (2.2 g, 4.62 mmol) and 4-(4,4,5,5-tetramethyl-[1,3,2]dioxaborolan-2-yl)-3,6-dihydro-2H-pyran (1.1 g, 5.08 mmol) in THF (200 mL) was added potassium phosphate (2.7 g, 13.86 mmol). The reaction mixture was degassed by purging with $N_2$ for 5 min, before $Pd_2(dba)_3$ (0.8 g, 0.92 mmol) and Xanthphos (1.0 g, 1.84 mmol) were added to the mixture. The resulting suspension was degassed with $N_2$ for 10 minutes. Then the mixture reaction was heated to 80° C. under an $N_2$ atmosphere for 15 hours. After cooling to room temperature, the reaction mixture was diluted with EtOAc (250 mL) and the precipitate was filtered off. The filtrate was concentrated. The crude residue was purified by column chromatography on silica gel (eluting with EtOAc) to afford 43 (1.3 g, 60% yield) as a solid.

$^1$H NMR (400 MHz, DMSO-$d_6$): δ 10.80 (m, 1H), 7.34 (s, 1H), 6.42 (s, 1H), 4.30-4.29 (m, 2H), 3.92-3.80 (m, 2H), 3.63-3.33 (m, 4H), 2.87-2.71 (m, 2H), 2.50 (m, 1H), 1.41 (s, 9H), 0.95 (m, 3H).

Synthesis of (S,S)-trans-3-[1-bromo-3-(3,6-dihydro-2H-pyran-4-yl)-8-oxo-7,8-dihydro-imidazo[1,5-a]pyrazin-6-yl]-4-methyl-pyrrolidine-1-carboxylic acid tert-butyl ester (S,S)-(43)

To a mixture of compound (S,S)-42 (2.11 g, 4.42 mmol) and 4-(4,4,5,5-tetramethyl-[1,3,2]dioxaborolan-2-yl)-3,6-dihydro-2H-pyran (0.975 g, 4.64 mmol) in 1,4-Dioxane (40 mL) and water (10 mL) was added potassium phosphate (2.57 g, 12.2 mmol). The reaction mixture was degassed by purging with $N_2$ for 5 min, before $Pd_2(dba)_3$ (0.8 g, 0.9 mmol) and Xanthphos (1.0 g, 1.8 mmol) were added to the mixture. The resulting suspension was degassed with $N_2$ for 10 minutes. Then the mixture reaction was heated to 80° C. under an N2 atmosphere for 15 hours. After cooling to room temperature, the reaction mixture was diluted with EtOAc (250 mL) and the solid was removed by filtration through Celite. The filtrate was concentrated. The crude residue was purified by column chromatography on silica gel (eluting with EtOAc) to afford 43 (1.4 g, 2.92 mmol) as a solid. The material has an ee above 99% at this stage.

Synthesis of racemic trans-3-methyl-4-[8-oxo-3-(tetrahydro-pyran-4-yl)-7,8-dihydro-imidazo[1,5-a]pyrazin-6-yl]-pyrrolidine-1-carboxylic acid tert-butyl ester (44)

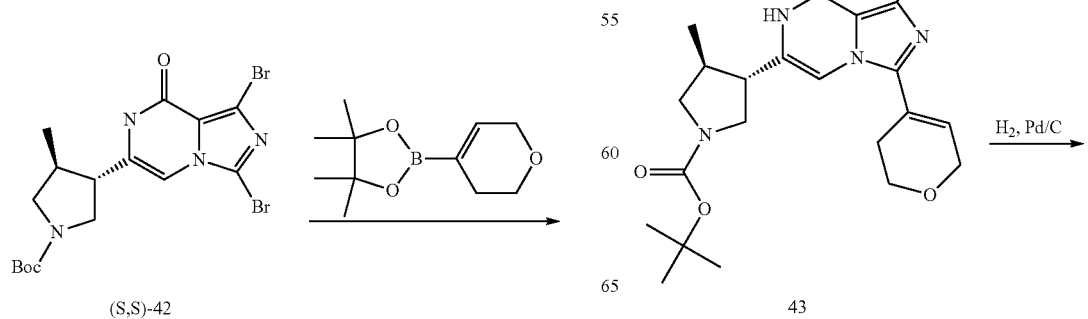

-continued

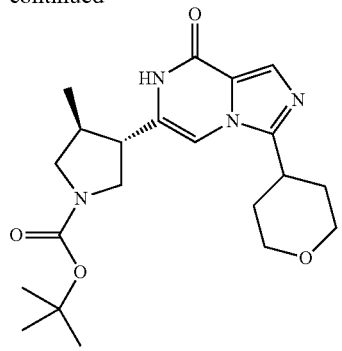

44

To a solution of 43 (1.3 g, 2.73 mmol) in DMF (100 mL) and methanol (30 mL) was added 10% Pd/C (0.8 g). The flask was charged with hydrogen (50 psi) and the mixture was stirred at 50° C. overnight. After cooling down, the reaction mixture was filtered through Celite. The filtrate was concentrated under reduced pressure. The crude product was purified by column chromatography on silica gel (eluting with DCM/CH$_3$OH=100/1-20/1) to afford compound 44 (0.99 g, 90% yield) as a solid.

$^1$HNMR (400 MHz, CDCl$_3$): δ 10.80 (br d, 1H), 7.86 (s, 1H), 6.79 (s, 1H), 4.13-4.10 (m, 2H), 3.83-3.79 (m, 3H), 3.63-3.49 (m, 2H), 3.13-3.03 (m, 2H), 2.77-2.75 (m, 2H), 2.54-2.53 (m, 1H), 2.11-2.06 (m, 2H), 1.80-1.85 (m, 2H), 1.48 (m, 9H), 1.12 (d, J=6.4 Hz, 3H).

Synthesis of (S,S)-trans-3-methyl-4-[8-oxo-3-(tetrahydro-pyran-4-yl)-7,8-dihydro-imidazo[1,5-a]pyrazin-6-yl]-pyrrolidine-1-carboxylic acid tert-butyl ester (S,S)-(44)

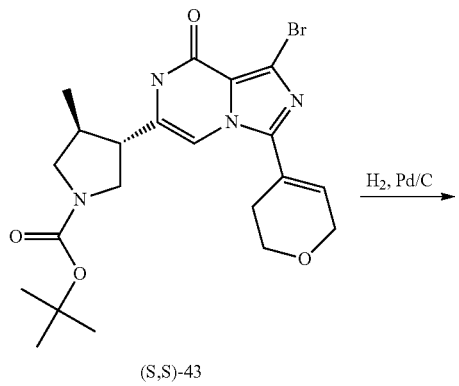

A solution of (S,S)-43 (1.15 g, 2.41 mmol) in methanol (50 mL) was placed in an autoclave under N$_2$-protective atmosphere and 10% Pd/C (0.8 g) was added under a nitrogen atmosphere. The reaction mixture was hydrogenated with stirring at 45-50° C. at 10-15 Bar H$_2$ pressure until no more hydrogen was absorbed (24 hrs). After cooling down, the reaction mixture was filtered through Celite. The filtrate was concentrated under reduced pressure. The crude product was purified by column chromatography on silica gel (eluting with DCM/CH$_3$OH=100/1-20/1) to afford compound 44 (0.97 g, 2.41 mmol) as a solid. The ee was determined to be above 99%.

Synthesis of racemic trans-6-(4-methyl-pyrrolidin-3-yl)-3-(tetrahydro-pyran-4-yl)-7H-imidazo[1,5-a]pyrazin-8-one (45)

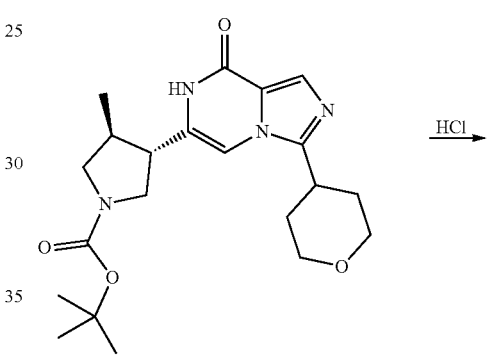

44

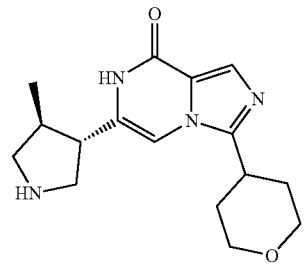

45

To a solution of compound 44 (0.99 g, 2.49 mmol) in CH$_2$Cl$_2$ (20 mL) was added HCl/Et$_2$O solution (20 mL). The resulting mixture was stirred at room temperature for 2 hours. The reaction was concentrated in vacuo to afford racemic trans 45 hydrochloride (0.75 g, 100% yield) as a solid.

$^1$H NMR (400 MHz, DMSO-d$_6$): δ 11.47 (s, 1H), 9.93 (s, 2H), 8.41 (s, 1H), 7.92 (s, 1H), 3.98-3.95 (m, 2H), 3.85-3.80 (m, 1H), 3.58-3.44 (m, 3H), 2.97-2.88 (m, 2H), 2.60-2.50 (m, 3H), 1.98-1.78 (m, 4H), 1.08 (m, 3H).

Synthesis of (S,S)-trans-6-(4-methyl-pyrrolidin-3-yl)-3-(tetrahydro-pyran-4-yl)-7H-imidazo[1,5-a]pyrazin-8-one (S,S)-(45)

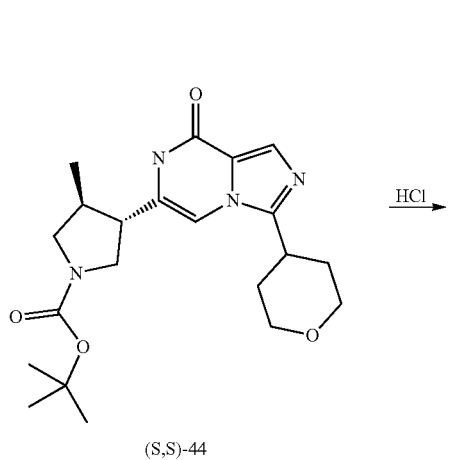

To a solution of compound (S,S)-44 (800 mg, 2.0 mmol) was added to a cold (0° C.) solution of HCl in MeOH (1.5 M, 10 mL) and the resulting reaction mixture was stirred while being allowed to reach room temperature. After stirring for 2 hrs the reaction was concentrated in vacuo to afford (S,S)-45 hydrochloride (0.60 g, 2.0 mmol) as a solid.

$^1$H NMR (400 MHz, DMSO-d$_6$): δ 11.47 (s, 1H), 9.93 (s, 2H), 8.41 (s, 1H), 7.92 (s, 1H), 3.98-3.95 (m, 2H), 3.85-3.80 (m, 1H), 3.58-3.44 (m, 3H), 2.97-2.88 (m, 2H), 2.60-2.50 (m, 3H), 1.98-1.78 (m, 4H), 1.08 (m, 3H).

Synthesis of racemic trans-6-(4-methyl-1-pyrimidin-2-ylmethyl-pyrrolidin-3-yl)-3-(tetrahydro-pyran-4-yl)-7H-imidazo[1,5-a]pyrazin-8-one (P3)

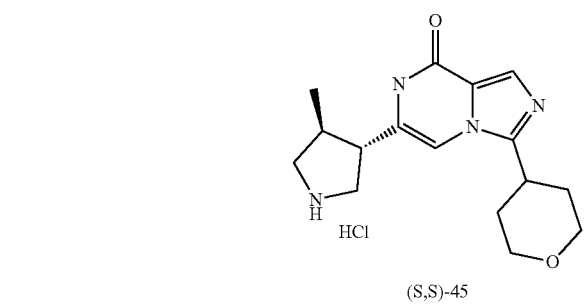

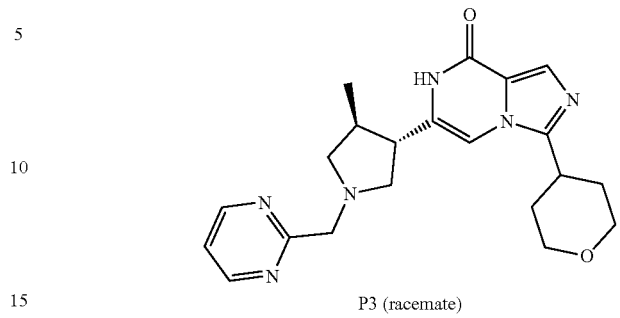

To a solution of compound 45 (0.75 g, 2.49 mmol), 2-chloromethyl-pyrimidine (0.49 g, 2.99 mmol) in DMF (10 mL) and CH$_3$CN (30 mL) was added K$_2$CO$_3$ (1.7 g, 12.5 mmol). The mixture was stirred at 45° C. for 48 hours. The reaction mixture was filtered, concentrated in vacuo. The residue was purified by flash column chromatography (gradient elution from DCM to 15% MeOH in DCM) to afford racemic trans P3 (580 mg, 59% yield) as a solid.

$^1$H NMR (400 MHz, CD$_3$OD): δ 8.85 (d, J=4.8 Hz, 2H), 7.79 (s, 1H), 7.42 (t, J=4.8 Hz, 1H), 7.36 (s, 1H), 4.11-4.04 (m, 3H), 3.93 (d, J=15.2 Hz, 1H), 3.684-3.62 (m, 2H), 3.41-3.32 (m, 2H), 3.16-3.13 (m, 1H), 2.85-2.80 (m, 2H), 2.44-2.40 (m, 1H), 2.28-2.23 (m, 1H), 2.04-1.86 (m, 4H), 1.17 (d, J=6.4 Hz, 3H). MS Calcd.: 394.5; MS Found: 395.8 ([M+H]$^+$).

The racemic mixture of P3 (1.4 g) was separated by Chiral HPLC (Column: Chiralpak IA, 250×4.6 mm×5 um; mobile phase Hex/EtOH/DEA=70:30:0.2) with a flow rate of 1.0 mL/min, to afford P3 enantiomer 1 ((3S,4S)-6-(4-methyl-1-pyrimidin-2-ylmethyl-pyrrolidin-3-yl)-3-(tetrahydro-pyran-4-yl)-7H-imidazo[1,5-a]pyrazin-8-one, or 6-[(3S,4S)-4-methyl-1-(pyrimidin-2-ylmethyl)pyrrolidin-3-yl]-3-tetrahydropyran-4-yl-7H-imidazo[1,5-a]pyrazin-8-one) (0.52 g, RT=9.98 min) and P3 enantiomer 2 ((3R,4R)-6-(4-methyl-1-pyrimidin-2-ylmethyl-pyrrolidin-3-yl)-3-(tetrahydro-pyran-4-yl)-7H-imidazo[1,5-a]pyrazin-8-one opposite of P3 enantiomer 1) (0.49 g, RT=12.6 min).

Synthesis of (S,S)-trans-6-(4-methyl-1-pyrimidin-2-ylmethyl-pyrrolidin-3-yl)-3-(tetrahydro-pyran-4-yl)-7H-imidazo[1,5-a]pyrazin-8-one (S,S)-(P3)

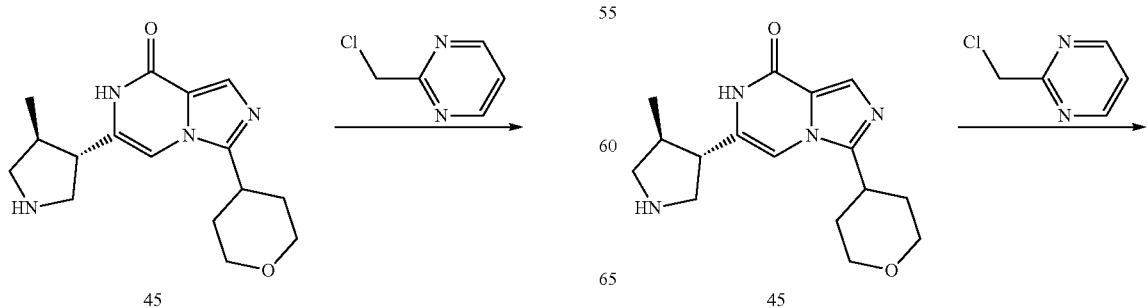

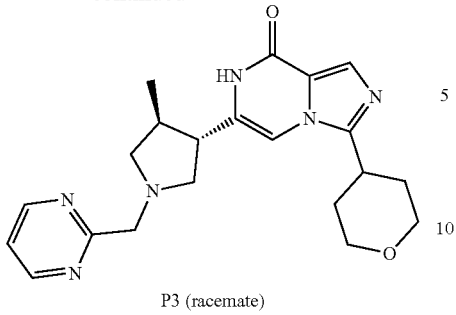

P3 (racemate)

To a solution of compound (S,S)-45 (0.60 g, 2.0 mmol) and 2-chloromethyl-pyrimidine (0.40 g, 2.40 mmol) in DCM (15 mL) was added DIPEA (3.1 g, 24 mmol) and the mixture was stirred at RT for 24 hrs (at this time all the starting material had been converted). The reaction mixture was cooled to 5° C., and deionised water (10 mL) was added. The pH of the aqueous phase was adjusted to pH 6.0 with addition of conc hydrochloric acid (about 1 mL) while keeping the temperature of the mixture <25° C. The phases were allowed to separate and the organic phase was washed with brine (3×5 mL) (these washings were discarded). The aqueous phase was extracted with dichloromethane (10 mL), and the organic phase from this extraction was washed with brine (3×5 mL). The combined organic phases were dried over sodium sulfate (3 g) for 1 hour, filtered and evaporated. The resulting residue was subjected to column chromatography (as described for rac-(P3)) to give (S,S)-P3 (580 mg, 59% yield) as a solid after evaporation. This material has ee above 99% and is identical in all ways to P3 Enantiomer 1 (described above).

Synthesis of (aminooxy) (diphenyl) phosphine oxide (B)

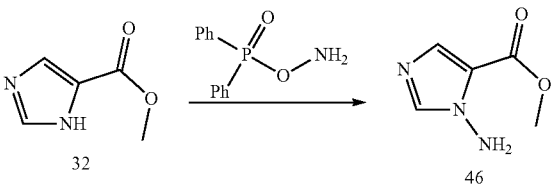

To a suspension of hydroxylamine hydrochloride (73.5 g, 1.05 mol) in dichloromethane (500 mL) was added DIPEA (136 g, 1.05 mol) over 15 minutes at −30° C. under a nitrogen atmosphere. A white precipitate formed upon the addition. After stirring for one hour at that temperature, a solution of diphenylphosphinic chloride A (50 g, 0.2 mol) in dichloromethane (100 mL) was added over 60 minutes. The mixture reaction was warmed to 0° C. over 1 hour with stirring. The reaction was quenched by adding water (200 mL) over 10 minutes. After stirring the mixture for 0.5 hour, the precipitate was collected by filtration and washed with water (100 mL×2). Then the solid was dried under reduced pressure to afford a crude product. The crude product was triturated in EtOH to afford compound B (27 g, 56% yield) as a white solid.

$^1$HNMR (400 MHz, CD$_3$OD): δ77.91-7.79 (m, 5H), 7.62-7.50 (m, 7H).

MS Calcd.: 233; MS Found: 234 ([M+H]$^+$).

Synthesis of 3-amino-3H-imidazole-4-carboxylic acid methyl ester (46)

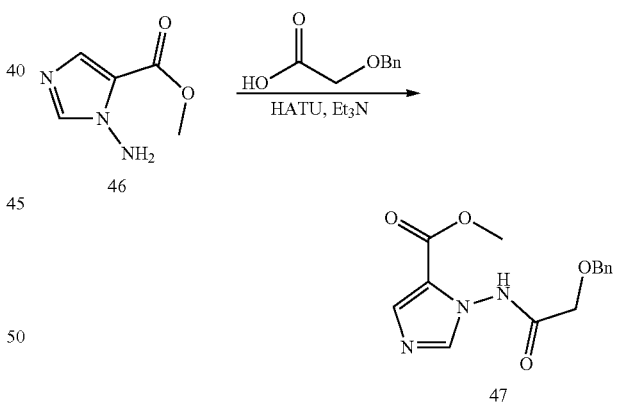

To a solution of compound 3H-Imidazole-4-carboxylic acid methyl ester 32 (30.0 g, 0.24 mol) in THF (1.0 L) was dropwise added LiHMDS (239 mL, 10M in THF, 2.4 mol) over 2 hours at −78° C. Then the reaction mixture was stirred at −78° C. for another two hours and allowed to warm to −10° C. Compound B (60.0 g, 0.26 mol) was added at this temperature. Then the mixture reaction was stirred at ambient temperature overnight. After quenching with water (250 mL), the reaction mixture was concentrated. The crude product was purified by column chromatography on silica gel (DCM/MeOH=20/1) to afford compound 46 (24 g, 73% yield) as a solid.

$^1$HNMR (400 MHz, DMSO-d6): δ 7.82 (s, 1H), 7.51 (s, 1H), 6.20 (s, 2H), 3.79 (s, 3H). MS Calcd.: 382; MS Found: 383 ([M+H]$^+$). MS Calcd.: 141; MS Found: 142 ([M+H]$^+$).

Synthesis of 3-(2-benzyloxy-acetylamino)-3H-imidazole-4-carboxylic acid methyl ester (47)

To a solution of compound 46 (4.9 g, 30 mmol), benzyloxy-acetic acid (5.8 g, 30 mmol) and DIPEA (18.6 ml, 90 mmol) in DMF (100 mL) was added HATU (15.8 g, 36 mmol) whilst cooling on an ice-water bath. The mixture was then stirred at ambient temperature overnight. After removal of the solvent, the residue was purified by chromatography on a silica gel column (eluted with PE/EtOAc=10:1 to 2:1) to afford compound 47 (6.1 g, 61% yield) as an oil.

$^1$HNMR (400 MHz, CDCl$_3$): δ 9.93 (br. s, 1H), 7.74 (s, 1H), 7.67 (s, 1H), 7.39-7.33 (m, 5H), 4.70 (s, 2H), 4.23 (s, 2H), 3.83 (s, 3H). MS Calcd.: 289; MS Found: 300 ([M+H]$^+$).

Synthesis of 3-(2-benzyloxy-acetylamino)-3H-imidazole-4-carboxylic acid amide

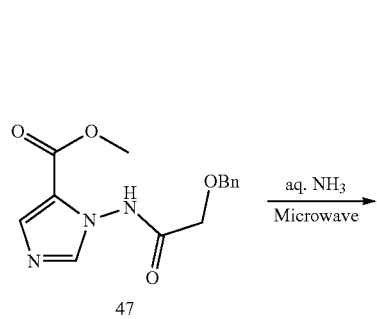

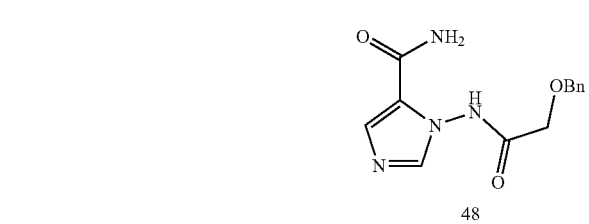

Compound 47 (30.0 g, 100 mmol) and conc aq. ammonia (300 nit) were combined in a sealed tube and heated to 70° C. under microwave radiation for 2 hours. The resulting mixture was concentrated in vacuo to afford compound 48 (26.3 g, 96% yield) as a solid. MS Calcd.: 274; MS Found: 275 ([M+H]⁺).

Synthesis of 2-benzyloxymethyl-3H-imidazo[5,1-f][1,2,4]triazin-4-one (49)

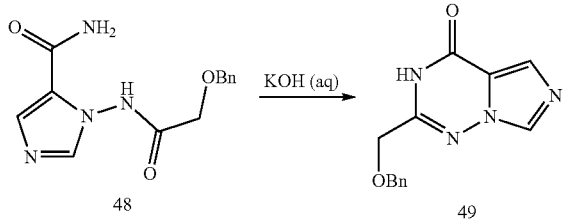 [SMILES: NC(=O)c1cncn1NC(=O)COCc1ccccc1 ; O=c1[nH]c(COCc2ccccc2)nn2cncc12]

To a solution of compound 48 (28.0 g, 100 mmol) in EtOH (240 mL) was dropwise added a solution of KOH (19.8 g, 300 mmol) in water (200 mL). The resulting solution was heated to reflux for 3 hours. After removal of the organic solvent in vacuo, the mixture was poured into ice water and the pH was adjusted to 7.0 with 1M aq HCl solution. The suspension was filtered off and dried to afford compound 49 (11.3 g, 44.1% yield) as a solid.

¹HNMR (400 MHz, DMSO-d6): δ 12.05 (s, 1H), 8.45 (s, 1H), 7.74 (s, 1H), 7.39-7.29 (m, 5H), 4.59 (s, 2H), 4.36 (s, 2H). MS Calcd.: 256; MS Found: 257 ([M+H]⁺).

Synthesis of 2-benzyloxymethyl-7-iodo-3H-imidazo[5,1-f][1,2,4]triazin-4-one (50)

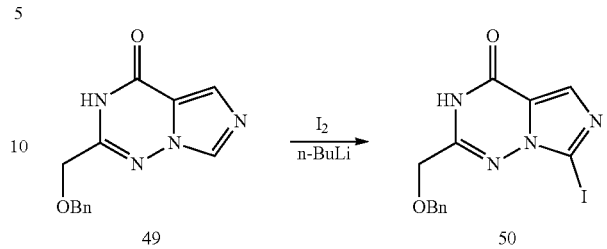

To a solution of compound 49 (10.0 g, 38.2 mmol) in THF (240 mL) was dropwise added n-BuLi (46 mL) at −78° C. and the reaction was stirred below −70° C. for one hour. Iodine (39.3 g, 153 mmol) in THF (120 mL) was added dropwise at this temperature and then the reaction temperature was allowed to warm to room temperature slowly. The reaction was quenched with saturated Na₂SO₃ aqueous solution (120 mL), and then extracted with EtOAc (150 mL×3). The combined organic phases were dried over Na₂SO₄, filtered and concentrated in vacuo to get the crude product. The residue was purified by chromatography on silica gel column (eluted with PE/EtOAc=10:1 to 2:1) to afford compound 50 (4.75 g, 32.5% yield) as a solid, ¹HNMR (400 MHz, DMSO-d6): δ 12.16 (br. s, 1H), 7.84 (s, 1H), 7.42-7.29 (m, 5H), 4.62 (s, 2H), 4.40 (s, 2H). MS Calcd.: 382; MS Found: 383 ([M+H]⁺).

Synthesis of 2-benzyloxymethyl-7-(3,6-dihydro-2H-pyran-4-yl)-3H-imidazo[5,1-f][1,2,4]triazin-4-one (51)

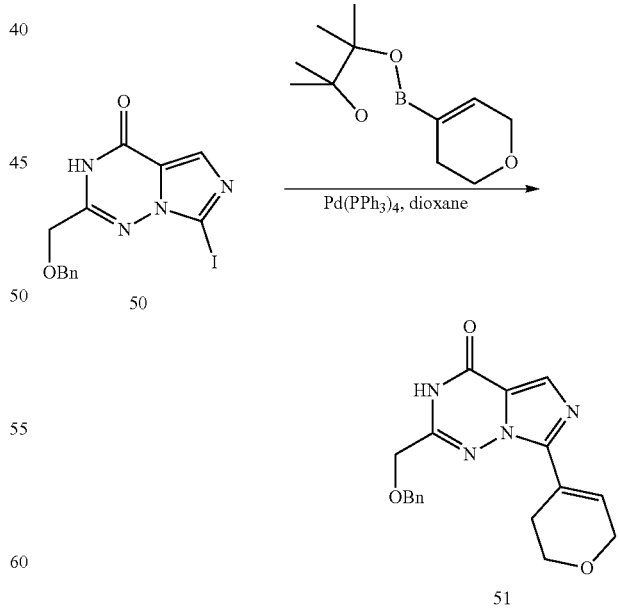

To a solution of compound 50 (4.75 g, 10.0 mmol) in dioxane (80 mL) was dropwise added a solution of Cs₂CO₃ (9.88 g, 30 mmol) in water (12 mL), followed by Pd(PPh₃)₄ (2.36 g, 2.00 mmol) and 4-(4,4,5,5-tetramethyl-[1,3,2]dioxaborolan-2-yl)-3,6-dihydro-2H-pyran (3.86 g, 18.0 mmol). The reaction mixture was degassed by purging with $N_2$ for 15 min. Then the mixture was heated to reflux for 16 hours. After removal of the solvent in vacuo, the residue was purified by chromatography on a silica gel column (eluted with PE/EtOAc=10:1 to 1:5) to afford compound 51 (2.1 mg, 76% yield) as a solid.

$^1$H NMR (400 MHz, DMSO-d6): δ 12.10 (br. s, 1H), 7.78 (s, 1H), 7.39-7.30 (m, 5H), 7.25 (s, 1H), 4.62 (s, 2H), 4.41 (s, 2H), 4.27 (d, J=2.8 Hz, 2H), 3.82 (t, J=5.2 Hz, 2H), 2.63 (m, 2H). MS Calcd.: 338; MS Found: 339 ([M+H]$^+$).

Synthesis of 2-hydroxymethyl-7-(tetrahydro-pyran-4-yl)-3H-imidazo[5,1-f][1,2,4]triazin-4-one (52)

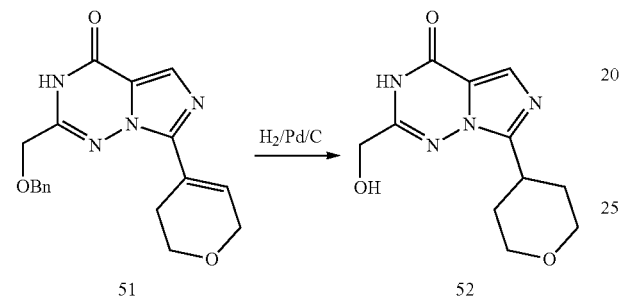

To a solution of compound 51 (1.8 g, 5.0 mmol) in MeOH (70 mL) was added Pd(OH)$_2$ (20% on Carbon (wetted with ca. 50% Water), 400 mg). The reaction flask was charged with hydrogen (50 psi) and the mixture was stirred on an oil bath heated to 70° C. until LC/MS showed that the starting material had been consumed. The suspension was filtered through celite, the filter was washed with MeOH (100 mL×2) and the combined organic phases were concentrated in vacuo to afford compound 52 (1.0 g, 79% yield) as a solid.

$^1$HNMR (400 MHz, DMSO-d6): δ 11.65 (s, 1H), 7.68 (s, 1H), 4.30 (s, 2H), 3.96-3.92 (m, 2H), 3.51-3.17 (m, 3H), 1.88-1.81 (m, 4H). MS Calcd.: 250; MS Found: 251 ([M+H]$^+$).

Synthesis of 2-chloromethyl-7-(tetrahydropyran-4-yl)-3H-imidazo[5,1-f][1,2,4]triazin-4-one (53)

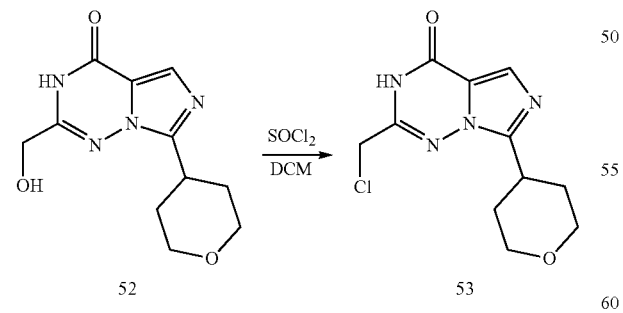

To a solution of compound 52 (1.0 g, 4 mmol) in CH$_2$Cl$_2$ (50 mL) was dropwise added SOCl$_2$ (15 mL) whilst cooling on an ice-water bath. The resulting mixture was then stirred at ambient temperature overnight. The reaction mixture was concentrated in vacuo to afford compound 53 (1.07 g, 100% yield) as a solid.

$^1$H NMR (400 MHz, DMSO-d6): δ 12.50 (br. s, 1H), 8.02 (s, 1H), 4.57 (s, 2H), 3.95 (m, 2H), 3.57-3.48 (m, 3H), 1.91-1.81 (m, 4H). MS Calcd.: 268; MS Found: 269 ([M+H]$^+$).

Synthesis of 3-(4-fluoro-benzyloxy)-azetidine-1-carboxylic acid tert-butyl ester (2)

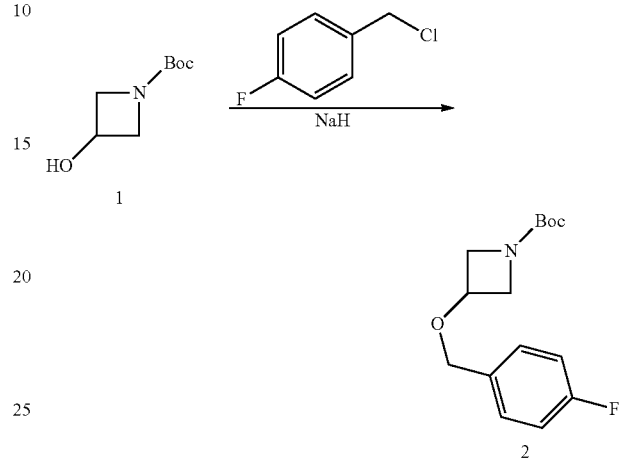

To a solution of compound 3-hydroxy-azetidine-1-carboxylic acid tert-butyl ester 1 (5.30 g, 30 mmol) in DMF (6 mL) was added NaH (1.80 g, 45 mmol) whilst cooling; on an ice-water bath. The suspension was then stirred at this temperature for one hour, followed by the addition of 1-chloromethyl-4-fluoro-benzene (8.94 g, 60 mmol). The resulting mixture was stirred at ambient temperature overnight. The reaction mixture was poured into water (200 mL) and extracted with EtOAc (150 mL×3). The organic combined phases were dried over Na$_2$SO$_4$, filtered and concentrated in vacuo to get the crude product. The residue was purified by chromatography on a silica gel column (eluted with PE/EtOAc=10:1 to 2:1) to afford compound 2 (7.90 g, 94% yield) as an oil.

$^1$H NMR (300 MHz, DMSO-d6): δ 7.41-7.37 (m, 2H), 7.21-7.14 (m, 2H), 4.40 (s, 2H), 4.33-4.29 (m, 1H), 4.02-3.97 (m, 2H), 3.68-3.66 (m, 2H), 1.37 (s, 9H). MS Calcd.: 281; MS Found: 282 ([M+H]$^+$).

Synthesis of 3-(4-fluoro-benzyloxy)-azetidine (3)

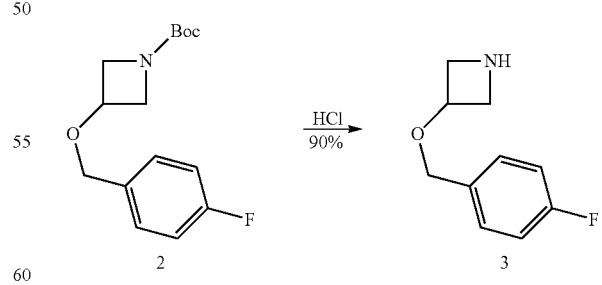

To a solution of compound 2 (2.68 g, 9.30 mmol) in dioxane (30 mL) was added HCl/dioxane (4 M, 9.25 under ice-water bath. The reaction mixture was then stirred at ambient temperature overnight. The reaction solution was concentrated in vacuo to afford compound 3 hydrochloride (1.2 g, 71% yield) as a solid.

$^1$H NMR (300 MHz, DMSO-d6): δ 7.36 (m, 2H), 7.16 (m, 2H), 4.35 (s, 2H), 4.39 (m, 1H), 3.47 (t, J=7.5 Hz, 2H), 3.38 (t, J=7.2 Hz, 2H). MS Calcd.: 181; MS Found: 182 ([M+H]$^+$).

Synthesis of 2-[3-(4-fluoro-phenoxy)-azetidin-1-ylmethyl]-7-(tetrahydro-pyran-4-yl)-3H-imidazo[5,1-f][1,2,4]triazin-4-one (P4)

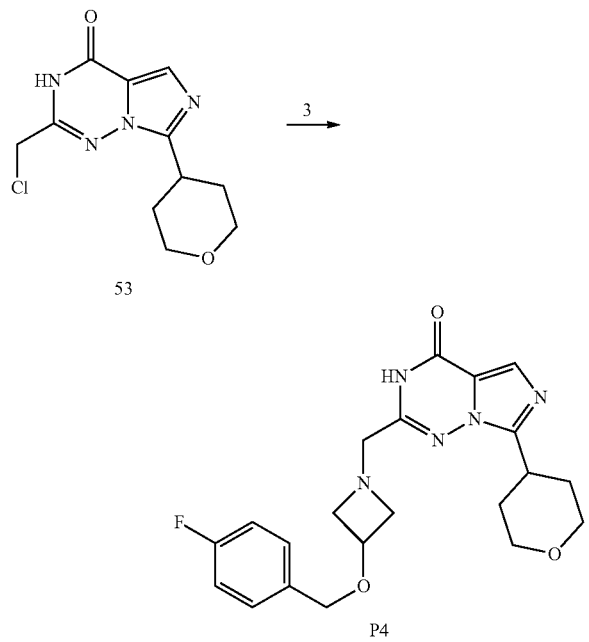

To a solution of compound 53 (1.27 mg, 4.0 mmol) and compound 3 (1.8 g, 8.3 mmol) in CH$_3$CN (20 mL) was added DIPEA (2.61 mL, 20 mmol). The result solution was heated to 70° C. for 2 hours. TLC indicated that the reaction was complete. The reaction was concentrated in vacuum. The residue was purified by column chromatography on silica gel (eluted with DCM/MeOH 100:1 to 30:1) to afford the desired product P4 (1.23 g, 74% yield) as a solid.

$^1$HNMR (400 MHz, DMSO-d6): δ 11.70 (br. s, 1H), 7.67 (s, 1H), 7.37 (m, 2H), 7.16 (m, 2H), 4.38 (s, 2H), 4.17 (m, 1H), 3.95-3.92 (m, 2H), 3.56 (t, J=8.0 Hz, 2H), 3.54-3.46 (m, 4H), 3.37-3.35 (m, 1H), 3.06-3.03 (m, 2H), 1.86-1.80 (m, 4H). MS Calcd.: 413; MS Found: 414 ([M+H]$^+$).

Example 2. X-Ray Crystal Structure of P3 Enantiomer 2

The single crystal X-ray structure of P3 enantiomer 2 has been determined at 100 K in the orthorhombic system, space group P2$_1$2$_1$2$_1$ using a crystal grown. There is one compound molecule and one molecule of water in the asymmetric unit. The final R1 [I>2δ(I)]=3.09%. The absolute stereochemistry of the compound has been FIG. 1.

P3 Enantiomer 2 Monohydrate

Instrument and Methodology Details

Crystallisation experiments were conducted to obtain suitable crystals to determine the structure and absolute configuration of P3 enantiomer 2 by single crystal X-ray diffraction.

X-Ray Powder Diffraction (XRPD)

X-Ray Powder Diffraction patterns were collected on a Bruker D8 diffractometer using Cu Kα radiation (40 kV, 40 mA), θ-2 θ goniometer, and divergence of V4 and receiving slits, a Ge monochromate and a Lynxeye detector. The instrument is performance checked using a certified Corundum standard (NIST 1976). The software used for data collection was Diffrac Plus XRD Commander v2.6.1 and the data were analysed and presented using Diffrac Plus EVA v15.0.0.0.

Samples were run under ambient conditions as flat plate specimens using powder as received. The sample was gently packed into a cavity cut into polished, zero-background (510) silicon wafer. The sample was rotated in its own plane during analysis. The details of the data collection are: Angular range: 2 to 42° 2 θ; Step size: 0.05° 2 θ; Collection time: 0.5 s/step.

Single Crystal X-Ray Diffraction (SCXRD)

Data were collected on an Oxford Diffraction Supernova Dual Source, Cu at Zero, Atlas CCD diffractometer equipped with an Oxford Cryosystems Cobra cooling device. The data were collected using CuKα radiation. Structures were typically solved using either the SHELXS or SHELXD programs and refined with the SHELXL program as part of the Bruker AXS SHELXTL suite (V6.10). Unless otherwise stated, hydrogen atoms attached to carbon were placed geometrically and allowed to refine with a riding isotropic displacement parameter. Hydrogen atoms attached to a heteroatom were located in a difference Fourier synthesis and were allowed to refine freely with an isotropic displacement parameter.

Polarised Light Microscopy (PLM)

Samples were studied on a Nikon SMZ1500 polarized light microscope with a digital video camera connected to a DS Camera control unit DS-L2 for image capture. A small amount of each sample was placed on a glass slide, mounted in immersion oil, the individual particles being separated as well as possible. The sample was viewed with appropriate magnification and partially polarized light, coupled to a λ false-colour filter.

Crystallisation Screen

Dissolution of P3 enantiomer 2 (5 mg) was attempted in selected solvent systems at 50° C. The solutions were placed in the fridge at 4° C. for 48 hours. The suspensions were filtered, and the resulting mother liquors were also placed at 4° C. Any cyrstals obtained were assessed by optical microscopy.

The material was soluble in most of solvent systems assessed, with the exception of isopropyl acetate and cumene. Large prism shaped crystals were obtained at 4° C. from a range of solvents, including acetonitrile, tetrahydrofurane and 1,4-dioxane. The crystal structure of P3 enantiomer 2 was solved using crystals obtained by cooling in acetonitrile.

Single Crystal Structure Determination

A crystalline sample of P3 enantiomer 2 was obtained by dissolving 5 mg of the supplied material in 50 μl of acetonitrile and cooling at 4° C. The crystals as obtained were of prism morphology. A crystal of sufficient size and quality for analysis by single crystal X-ray diffraction was isolated with approximate dimensions 0.25×0.15×0.11 mm. Optical micrographs of the crystals as received and the single crystal used for the data collection are shown in FIG. 1.

Figure 3:
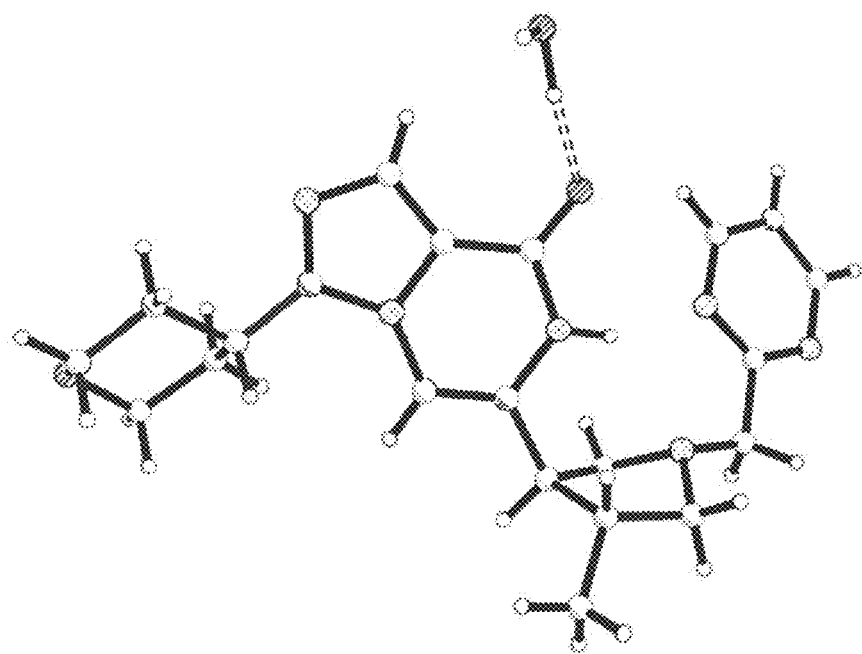
FIG. 3 is a ball and stick diagram of Compound P3 enantiomer 2 monohydrate.

The structure was determined at 100 K in the orthorhombic system, space group P2$_1$2$_1$2$_1$ with the final R1 {I>2δ(I)] =3.09%. The compound was identified as a monohydrate of P3 enantiomer 2 as depicted in FIG. 1 and FIG. 3. The asymmetric unit contains a fully ordered molecule of P3 enantiomer 2 and one molecule of water. Anisotropic atomic displacement ellipsoids for the non-hydrogen atoms are shown at the 50% probability level. Hydrogen atoms are displayed with an arbitrarily small radius.

For the absolute stereochemistry of P3 enantiomer 2 shown in FIG. 1, C12 and C13 (the numbering is not the numbers used in IUPAC names) are in the R configuration, the Flack parameter=−0.03 (4). For the inverted structure with C12 and C13 in the S configuration (P3 enantiomer 1), the Flack parameter=1.03 (4).

Determination of the absolute structure using Bayesian statistics on Bijvoet differences, reveals that the probability of the absolute structure as presented being correct is 1.000, while the probabilities of the absolute structure being a racemic twin or false are both 0.000. The Flack equivalent and its uncertainty are calculated through this program to be −0.02 (4). The calculation was based on 1806 Bijvoet pairs with a coverage of 100%.

Conformational analysis of P3 enantiomer 2 shows the pyrimidine ring is planar, the pyrrolidine ring is an envelope on the nitrogen, and the tetrahydropyran ring is a chair.

As the opposite of P3 enantiomer 2, P3 enantiomer 1 has a structure of:

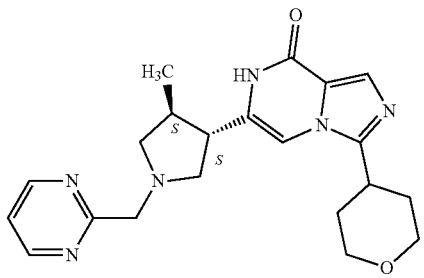

Example 3. In Vitro Testing

PDE9 Inhibition Assay

A PDE9 assay may for example, be performed as follows: The assay is performed in 60 uL samples containing a fixed amount of the relevant PDE enzyme (sufficient to convert 20-25% of the cyclic nucleotide substrate), a buffer (50 mM HEPES7.6; 10 mM $MgCl_2$; 0.02% Tween20), 0.1 mg/ml BSA, 225 pCi of $^3$H-labelled cyclic nucleotide substrate, tritium labeled cAMP to a final concentration of 5 nM and varying amounts of inhibitors. Reactions are initiated by addition of the cyclic nucleotide substrate, and reactions are allowed to proceed for one hr at room temperature before being terminated through mixing with 15 uL 8 mg/mL yttrium silicate SPA beads (Amersham). The beads are allowed to settle for one hr in the dark before the plates are counted in a Wallac 1450 Microbeta counter. The measured signal can be converted to activity relative to an uninhibited control (100%) and $IC_{50}$ values can be calculated using the Xlfit extension to EXCEL.

In the context of the present invention the assay was performed in 60 uL assay buffer (50 mM HEPES pH 7.6; 10 mM $MgCl_2$; 0.02% Tween20) containing enough PDE9 to convert 20-25% of 10 nM $^3$H-cAMP and varying amounts of inhibitors. Following a 1 hour incubation the reactions were terminated by addition of 15 uL 8 mg/mL yttrium silicate SPA beads (Amersham). The beads were allowed to settle for one hr in the dark before the plates were counted in a Wallac 1450 Microbeta counter. $IC_{50}$ values were calculated by nonlinear regression using XLfit (IDBS).

Results of the experiments showed that the tested compounds of the invention inhibit the PDE9 enzyme with $IC_{50}$ values below 100 nM.

PDE1 inhibition assay

PDE1 assays were performed as follows: the assays was performed in 60 µL samples containing a fixed amount of the PDE1 enzym1 (sufficient to convert 20-25% of the cyclic nucleotide substrate), a buffer (50 mM HEPES pH 7.6; 10 mM $MgCl_2$; 0.02% Tween20), 0.1 mg/ml BSA, 15 nM tritium labelled cAMP and varying amounts of inhibitors. Reactions were initiated by addition of the cyclic nucleotide substrate, and reactions were allowed to proceed for 1 h at room temperature before being terminated through mixing with 20 µL (0.2 mg) yttrium silicate SPA beads (PerkinElmer). The beads were allowed to settle for 1 h in the dark before the plates were counted in a Wallac 1450 Microbeta counter.

The measured signals were converted to activity relative to an uninhibited control (100%) and $IC_{50}$ values were calculated using XlFit (model 205, IDBS).

Example 4. In Vivo Testing

Blood Brain Barrier Penetration

Male CD mice (20-24 g) were housed pair-wise with free access to food and water for an acclimatization period of 3-7 days before initiation of experiments. Prior to dosing the animals were fasted overnight. During testing, mice were kept in individual cages. The brain-to-plasma distribution was assessed 30 minutes and 2 hours after subcutaneous administration of the test compound at a dose of 10 mg/kg (n=3 at each time point). The dose volume was 10 ml/kg using appropriate vehicle to solubilize each test compound. At the time of sampling, animals were anesthetized with isoflurane and a systemic blood sample collected by cardiac puncture into vacutainers containing sodium heparin as anti-coagulant. The blood was centrifuged at 3500 rpm for 10 minutes at 4° C. to obtain plasma. Following decapitation, brains were dissected out and transferred to pre-weighed vessels followed by tissue weights determination. Plasma and brains were stored at −80° C. until quantitative bioanalysis by LC-MS/MS. Results are expressed as ng/ml for plasma and ng/g for brain samples.

The invention claimed is:

1. A pharmaceutical composition comprising compound (3S,4S) -6-(4-methyl-1-pyrimidin-2-ylmethyl-pyrrolidin-3-yl)-3-(tetrahydro-pyran-4-yl)-7H -imidazo[1,5-a]pyrazin-8-one and one or more pharmaceutically acceptable carriers, diluents, or excipients, wherein the compounds is present in the composition from 0.01 mg to 1000 mg per dose.

2. The pharmaceutical composition of claim 1, wherein the compound is present in the composition from 0.05 mg to 500 mg per dose.

3. The pharmaceutical composition of claim 1, wherein the compound is present in the composition from 0.05 to 200 mg per dose.

4. A method of treating sickle cell disease in a patient in need thereof, comprising administering to the patient from 0.001 mg/kg to 100 mg/kg body weight per day of a compound (3S,4S)-6-(4-methyl-1-pyrimidin-2-ylmethyl-pyrrolidin-3-yl)-3-(tetrahydro-pyran-4-yl)-7H-imidazo[1,5-a]pyrazin-8-one.

5. The method of claim 4, wherein the compound is administered to the patient from 0.01 mg/kg to 50 mg/kg body weight per day.

6. The method of claim 4, wherein the compound is administered to the patient from 0.05 mg/kg to 10 mg/kg body weight per day.

7. The method of claim 4, wherein the compound is administered to the patient orally.

8. The method of claim 4, wherein the compound is administered to the patient in one to three doses per day.

\* \* \* \* \*